(12) United States Patent
Gosangari et al.

(10) Patent No.: US 10,772,842 B2
(45) Date of Patent: *Sep. 15, 2020

(54) ABUSE-DETERRENT OPIOIDS

(71) Applicant: PATHEON SOFTGELS INC., High Point, NC (US)

(72) Inventors: Saujanya Gosangari, Jamestown, NC (US); Justin Hughey, Asheboro, NC (US); Tatyana Dyakonov, Greensboro, NC (US); George Vamvakas, Greensboro, NC (US); Aqeel A. Fatmi, High Point, NC (US)

(73) Assignee: PATHEON SOFTGELS INC., High Point, NC (US)

( * ) Notice: Subject to any disclaimer, the term of this patent is extended or adjusted under 35 U.S.C. 154(b) by 134 days.

This patent is subject to a terminal disclaimer.

(21) Appl. No.: 14/877,208

(22) Filed: Oct. 7, 2015

(65) Prior Publication Data

US 2016/0199368 A1  Jul. 14, 2016

Related U.S. Application Data

(63) Continuation-in-part of application No. PCT/US2015/024464, filed on Apr. 6, 2015, and a continuation-in-part of application No. 14/679,233, filed on Apr. 6, 2015.

(60) Provisional application No. 62/101,431, filed on Jan. 9, 2015.

(51) Int. Cl.
| | | |
|---|---|---|
| *A61K 9/48* | (2006.01) | |
| *A61K 31/485* | (2006.01) | |
| *A61K 31/137* | (2006.01) | |
| *A61K 31/00* | (2006.01) | |

(52) U.S. Cl.
CPC ............ *A61K 9/4866* (2013.01); *A61K 9/485* (2013.01); *A61K 9/4858* (2013.01); *A61K 9/4875* (2013.01); *A61K 31/00* (2013.01); *A61K 31/137* (2013.01); *A61K 31/485* (2013.01)

(58) Field of Classification Search
None
See application file for complete search history.

(56) References Cited

U.S. PATENT DOCUMENTS

| | | | |
|---|---|---|---|
| 4,795,642 A * | 1/1989 | Cohen | A61K 9/4858 264/4.3 |
| 5,146,730 A | 9/1992 | Sadek et al. | |
| 5,459,983 A | 10/1995 | Sadek et al. | |
| 6,258,042 B1 | 7/2001 | Factor et al. | |
| 6,482,516 B1 | 11/2002 | Sadek et al. | |
| 6,949,256 B2 | 9/2005 | Fonkwe et al. | |
| 7,887,838 B2 | 2/2011 | Archibald et al. | |
| 8,293,270 B2 | 10/2012 | Sukuru | |
| 8,333,989 B2 | 12/2012 | Sukuru | |
| 8,685,445 B2 | 4/2014 | Hassan et al. | |
| 2004/0052839 A1 | 3/2004 | Archibald et al. | |
| 2005/0095285 A1 | 5/2005 | Rao et al. | |
| 2006/0115527 A1 | 6/2006 | Hassan et al. | |
| 2006/0165778 A1 | 7/2006 | Hassan et al. | |
| 2007/0053868 A1 | 3/2007 | Chidambaram et al. | |
| 2007/0122482 A1* | 5/2007 | Holm | A61K 9/1617 424/489 |
| 2007/0196463 A1 | 8/2007 | Podili et al. | |
| 2011/0142943 A1* | 6/2011 | Rariy | A61K 9/1617 424/489 |

FOREIGN PATENT DOCUMENTS

WO   WO02/49637   6/2002

OTHER PUBLICATIONS

International Search Report for PCT/US2015/036539, dated Sep. 25, 2015.

* cited by examiner

*Primary Examiner* — Layla Soroush
(74) *Attorney, Agent, or Firm* — Michael Best & Friedrich LLP

(57) ABSTRACT

Described herein are abuse deterrent controlled release oral pharmaceutical compositions comprising and methods for making the same. In particular, an abuse deterrent controlled release oral pharmaceutical composition comprising a soft capsule and an abuse deterrent controlled release matrix comprising an active pharmaceutical ingredient are described.

17 Claims, 17 Drawing Sheets

ABUSE-DETERRENT OPIOIDS

CROSS REFERENCE TO RELATED APPLICATIONS

This application claims priority to U.S. Provisional Patent Application No. 62/101,431, filed on Jan. 9, 2015; U.S. patent application Ser. No. 14/679,233 and International Patent Application No. PCT/US2015/24464, both filed on Apr. 6, 2015; each of the foregoing applications are incorporated by reference herein in its entirety. This application is related to U.S. patent application Ser. No. 14/679,062 and International Patent Application No. PCT/US2015/24422, both filed on Apr. 6, 2015, and each of which are incorporated by reference herein in its entirety. This application is also related to International Patent Application No. PCT/US2015/54443, filed on Oct. 7, 2015, which is incorporated by reference herein in its entirety.

TECHNICAL FIELD

Described herein are abuse deterrent controlled release oral pharmaceutical compositions and methods for making the same. In particular, an abuse deterrent controlled release oral pharmaceutical composition comprising a soft capsule and an abuse deterrent controlled release matrix comprising an active pharmaceutical ingredient are described.

BACKGROUND

Increased attention has been drawn to the recreational use and abuse of prescription pharmaceutical compositions. The abuse, or non-medicinal use, of prescription pharmaceutical compositions is an increasing problem. Accordingly, preventing the abuse of prescription pharmaceuticals through the development of abuse deterrent pharmaceutical compositions has become a high public health priority for the U.S. Food and Drug Administration (FDA). Prescription pharmaceutical compositions that are typically misused or abused fall, primarily, into three groups: (1) opioids prescribed for pain; (2) Central Nervous System (CNS) depressants prescribed for anxiety or sleep problems; and (3) stimulants, prescribed, for example, for attention deficit hyperactivity, narcolepsy, or obesity.

Methods for abusing prescription pharmaceutical compositions are varied and can include, for example, extraction, boiling, melting, volatilization, physical tampering (e.g., grinding, grating, crushing, etc.), or direct administration. For purposes of abuse, methods of administering active drug substances obtained from prescription pharmaceutical compositions or of the pharmaceutical compositions themselves are similarly diverse and include, for example, injection, smoking, snorting, swallowing, sublingual or buccal administration, chewing, or administration as an anal or vaginal suppository. Alcohol-induced "dose dumping," i.e., the rapid release of active pharmaceutical ingredients in the presence of a solvent such as ethanol, is also an abuse concern and safety issue. Other methods include rapid extraction under aqueous boiling conditions.

There are a number of strategies for preventing the abuse of pharmaceuticals. Physical and chemical barriers can prevent the extraction of the drug or change the form of the drug making it less likely to be abused. Combinations of agonists and antagonists can be used, wherein the antagonist is only released upon product manipulation or tampering. Another strategy is to use aversive compounds that produce an unpleasant effect when the dosage form is tampered with. In addition, prodrugs can be used, which are only changed into the active form of the drug in the gastrointestinal tract. The pharmaceutical industry is utilizing these strategies to develop abuse-deterrent pharmaceutical compositions in order to reduce the potential for misuse of prescription pharmaceutical compositions.

Accordingly, there is a need for abuse deterrent pharmaceutical compositions that have controlled release properties. In particular, there is a need for formulations that are resistant to active pharmaceutical ingredient extraction under boiling conditions.

SUMMARY

Described herein are pharmaceutical compositions comprising abuse deterrent controlled release matrices comprising active pharmaceutical ingredients. The matrix is structured to prevent extraction of the active pharmaceutical ingredients. The matrix formulations described herein minimize the likelihood of tampering, "dose dumping," or the extraction of active pharmaceutical ingredients from the composition.

One embodiment described herein is an abuse deterrent oral pharmaceutical composition comprising a tamper resistant controlled release matrix, wherein the tamper resistant controlled release matrix comprises a means for preventing the crushing, grating, grinding, cutting, solvating, or dissolving of the tamper resistant controlled release matrix comprising one or more active pharmaceutical ingredients.

Another embodiment described herein is an abuse deterrent oral pharmaceutical composition comprising a tamper resistant controlled release matrix comprising: (a) at least one lipid or lipophilic vehicle; (b) at least one organogelator; (c) at least one hydrophilic polymer; (d) at least one hydrophilic vehicle; and (e) at least one active pharmaceutical ingredient; wherein the matrix is resistant to tampering and is encapsulated in a soft capsule shell. In one aspect described herein, the tamper resistant controlled release matrix further comprises at least one antioxidant. In another aspect described herein, wherein the tamper resistant controlled release matrix further comprises at least one disintegrant. In another aspect described herein, the lipid or lipophilic vehicle comprises about 30% to about 85% of the total matrix mass. In another aspect described herein, the at least one organogelator comprises from about 0.5% to about 25% of the total matrix mass. In another aspect described herein, the at least one hydrophilic polymer comprises about 1% to about 30% of the total matrix mass. In another aspect described herein, the at least one hydrophilic vehicle comprises about 2% to about 40% of the total matrix mass. In another aspect described herein, the at least one active pharmaceutical ingredient comprises about 1% to about 35% of the total matrix mass. In another aspect described herein, the at least one anti-oxidant comprises about 0.05% to about 0.5% of the total matrix mass. In another aspect described herein, the at least one disintegrant comprises about 0.01% to about 5% of the total matrix mass. In another aspect described herein, the ratio of the active pharmaceutical ingredient percent mass to the matrix percent mass is about 1:100 to about 1:3. In another aspect described herein, the lipid or lipophilic vehicle comprises at least one liquid lipid or lipophilic vehicle and at least one semisolid lipid or lipophilic vehicle. In another aspect described herein, the lipid or lipophilic vehicle comprises at least one liquid lipid or lipophilic vehicle and not a semisolid lipid or lipophilic vehicle. In another aspect described herein, the liquid lipid or lipophilic vehicle comprises: olive oil, sunflower oil, canola oil, palmitoleic acid, oleic acid, myristoleic acid, linoleic acid, arachidonic acid, paraffin oil, or mineral oil. In another aspect described herein, the lipid or lipophilic vehicle comprises olive oil or soybean oil. In another aspect described herein, the semisolid lipid or lipophilic vehicle comprises one or more of: polyethylene glycol glyceride ester, paraffin wax, carnauba wax, or bee's wax. In another aspect described herein, the semisolid lipid or lipophilic vehicle comprises a combination of carnauba wax and bee's wax. In another aspect described herein, the lipid or lipophilic vehicle comprises soybean oil and carnauba wax, soybean oil and bee's wax, or soybean oil and a combination of carnauba wax and bee's wax. In another aspect described herein, the organogelator forms a gel at a temperature of about 90° C. to about 120° C. In another aspect described herein, the organogelator comprises one or more of: a mixture of simple alkanes and hexadecane, 12-hydroxyoctadecanoic acid, 1, 3:2,4-di-O-benzylidene-D-sorbitol, 2,3-bis-n-decyloxyanthracene, alkyl perfluoroalkanamides, sorbitan monostearate, or ethyl cellulose, or a combination thereof. In another aspect described herein, the organogelator comprises ethyl cellulose. In another aspect described herein, the ethyl cellulose comprises a viscosity value of about 3 cP to about 350 cP. In another aspect described herein, the ethyl cellulose comprises a viscosity value of about 4 cP to about 100 cP. In another aspect described herein, the ethyl cellulose comprises a viscosity value of about 3 cP to about 20 cP. In another aspect described herein, the hydrophilic polymer comprises methylcellulose, hydroxypropylmethyl cellulose, a mixture of hydroxypropylmethyl cellulose and methylcellulose, polymethylmethacrylate, polyvinyl pyrrolidone, or a combination thereof. In another aspect described herein, the hydrophilic polymer comprises methylcellulose. In another aspect described herein, the hydrophilic polymer comprises hydroxypropylmethyl cellulose. In another aspect described herein, methylcellulose has a viscosity value of about 50 to about 4,000 cP. In another aspect described herein, hydroxypropylmethyl cellulose has a viscosity value of about 50 to about 100,000 cP. In another aspect described herein, the anti-oxidant comprises alpha-tocopherol, beta-tocopherol, gamma-tocopherol, delta-tocopherol, butylated hydroxytoluene (BHT), butylated hydroxyanisole (BHA), citric acid, ascorbic acid, carnosic acid, carnosol, rosmanol, epirosmanol, isorosmanol, methyl carnosate, rosmarinic acid, eugenol, eugenyl acetate, clove bud extract, methanolic extract, epigallocatechin gallate, epicatechin gallate, epigallocatechin, epicatechin, or a combination thereof. In another aspect described herein, the disintegrant comprises crospovidone, crosslinked sodium carboxymethyl cellulose (croscarmellose sodium) carboxymethyl cellulose calcium, cysteine HCl, sodium starch glycolate, cellulose, calcium silicate, silicon dioxide, alginic acid, sodium alginate, citric acid, microcrystalline cellulose, polyoxy stearate, sodium croscarmellose, sodium lauryl sulfate, or a combination thereof. In another aspect described herein, the active pharmaceutical ingredient comprises at least one of: hydrocodone, morphine, morphine analogues, or morphine antagonists, tapentadol, codeine, morphine, methadone, fentanyl and analogs, hydrocodone hydrochloride, hydrocodone bitartrate, hydromorphone, oxymorphone, oxycodone, meperidine, propoxyphene, flunitrazepam, barbiturates, amytal, nembutal, seconal, phenobarbital; benzodiazepines, zolpidem, zaleplon, eszopiclone, amphetamines, methylphenidate, or a combination thereof. In another aspect described herein, the active pharmaceutical ingredient comprises hydrocodone or oxycodone. In another aspect described herein, the active pharmaceutical ingredient comprises hydrocodone or oxycodone and a second active pharmaceutical ingredient that reduces the symptoms of or onset of or prophylaxis of a bowel dysfunction due to acute or chronic opioid use. In another aspect described herein, the second active pharmaceutical ingredient comprises a laxative comprising lubiprostone, linaclotide, lactulose, a heavy molecular weight poly ethylene glycol (e.g., PEG 3350; Miralax®; GlycoLax), sorbitol, calcium carbonate, potassium phosphate, magnesium hydroxide, psyllium, glycerin, polycarbophil, or docusate, a natural therapeutic or nutraceutical comprising barberry, cascara sagrada, flax, or senna, a peripherally acting mu-opioid receptor antagonist comprising methylnaltrexone, naltrexone, naloxone, naloxegol, alvimopan, or a combination thereof. In another aspect described herein, the peripherally acting mu-opioid receptor antagonist comprises methylnaltrexone, naltrexone, naloxone, naloxegol, alvimopan, or a combination thereof. In another aspect described herein, the peripherally acting mu-opioid receptor antagonist comprises naloxone, methyl naltrexone, or naltrexone. In another aspect described herein, the active pharmaceutical ingredient comprises naloxone and hydrocodone or naloxone and oxycodone. In another aspect described herein, the at least one active pharmaceutical ingredient comprises naltrexone and hydrocodone or naltrexone and oxycodone.

In another embodiment described herein, the tamper resistant controlled release matrix comprises: (a) soybean oil; (b) ethyl cellulose; (c) carnauba wax; (d) bee's wax; (e) methylcellulose; (f) polyethylene glycol; (g) hydrocodone or oxycodone; and optionally: (h) microcrystalline cellulose; (i) BHT; and (j) BHA. In one aspect, the tamper resistant controlled release matrix comprises: (a) about 30% to about 70% soybean oil; (b) about 1% to about 7% Ethocel™ 20 cP; (c) comprises about 0% to about 10% bee's wax; (d) about 0% to about 10% carnauba wax; (e) about 1% to about 8% Methocel™ A4M; (f) about 2% to about 40% polyethylene glycol 400; (g) about 10.5% of hydrocodone or oxycodone; and optionally: (h) about 0.25% BHT; and (i) about 0.1% BHA. In another aspect described herein, the tamper resistant controlled release matrix further comprises a peripherally acting mu-opioid receptor antagonist comprising naloxone, methyl naltrexone, or naltrexone. In another aspect described herein, the weight percentage ratio of naloxone methyl naltrexone or naltrexone to hydrocodone or oxycodone is about 15:1 to about 1:18. In another aspect described herein, the weight percentage ratio of naloxone to hydrocodone or oxycodone is about 1:2.

In another embodiment described herein, the tamper resistant controlled release matrix comprises: (a) soybean oil; (b) ethyl cellulose; (e) hydroxypropylmethyl cellulose; (f) polyethylene glycol; (g) hydrocodone or oxycodone; and optionally (h) BHT; and (i) BHA. In one aspect, the tamper resistant controlled release matrix comprises: (a) about 30% to about 70% soybean oil; (b) about 1% to about 7% Ethocel™ 20 cP; (c) comprises about 0% to about 10% bee's wax; (d) about 0% to about 10% carnauba wax; (e) about 1% to about 30% Methocel™ K100M; (f) about 2% to about 40% polyethylene glycol 400; (g) about 10.5% of hydrocodone or oxycodone; and optionally (h) about 0.25% BHT; and (i) about 0.1% BHA. In another aspect described herein, the tamper resistant controlled release matrix further comprises a peripherally acting mu-opioid receptor antagonist comprising naloxone, methyl naltrexone, or naltrexone. In another aspect described herein, the weight percentage ratio of naloxone methyl naltrexone or naltrexone to hydrocodone or oxycodone is about 15:1 to about 1:18. In another aspect described herein, the weight percentage ratio of naloxone to hydrocodone or oxycodone is about 1:2.

In another embodiment described herein, the soft capsule shell comprises a film forming polymer, a plasticizer, a solvent, optionally, an opacifying agent, a coloring agent, or a pharmaceutical excipient. In another aspect described herein, the soft capsule shell comprises: (a) about 25% to about 50% of at least one film-forming polymer; (b) about 15% to about 25% of at least one plasticizer; (c) about 20% to about 40% of a solvent; (d) optionally, an opacifying agent, a coloring agent, a pharmaceutical excipient, or combination thereof. In another aspect described herein, the soft capsule shell comprises: (a) about 42% of at least one film-forming polymer; (b) about 20% of at least one plasticizer; (c) about 38% of a solvent; (d) optionally, about 0.7% of an opacifying agent; and (e) optionally, about 0.1% at least one coloring agent. In another aspect described herein, the soft capsule shell comprises gelatin, glycerol, water, and optionally, titanium oxide, and a coloring agent. In another aspect described herein, the soft capsule shell comprises gelatin, glycerol, water, and optionally, titanium oxide, and a coloring agent.

Another embodiment described herein is a method for making a tamper resistant controlled release matrix dosage form comprising the steps of: (a) heating one or more liquid lipophilic vehicles to about 60° C. and adding one or more organogelators until completely dissolved to form a first clear gel mixture; (b) hydrating one or more hydrophilic polymers (e.g., hydroxypropyl methyl cellulose) with one or more hydrophilic vehicles (e.g., polyethylene glycol); (c) mixing one or more active pharmaceutical ingredients with the mixture of step (b) to form a second uniform mixture; and (d) adding the second uniform mixture of step (c) to the first clear gel mixture of step (a) to form a final uniform matrix composition. In one aspect, the tamper resistant controlled release comprises: (a) soybean oil; (b) ethyl cellulose; (e) hydroxypropylmethyl cellulose; (f) polyethylene glycol; and (g) hydrocodone or oxycodone. In another aspect described herein, step (a) further comprises adding one or more semi-solid lipid or lipophilic vehicles or one or more disintegrants one or more anti-oxidants or a combination thereof.

Another embodiment described herein is a method for manufacturing a soft capsule shell and a tamper resistant controlled release matrix comprising the steps of: (a) providing a matrix comprising a tamper resistant controlled release matrix as described herein made by the methods described herein; (b) providing a soft capsule gel mass; (c) casting the soft capsule gel mass into films using heat-controlled drums or surfaces; and (d) forming a soft capsule comprising the matrix composition using rotary die encapsulation technology.

Another embodiment described herein is a soft capsule comprising a tamper resistant controlled release matrix produced by the method described herein.

Another embodiment described herein is an enteric soft capsule comprising a tamper resistant controlled release matrix produced by the method described herein.

Another embodiment described herein is a tamper resistant oral pharmaceutical composition comprising a tamper resistant controlled release matrix comprising: (a) about 30% to about 70% soybean oil; (b) about 1% to about 7% Ethocel™ 20 cP; (c) about 0% to about 7% bee's wax; (d) about 0% to about 7% carnauba wax; (e) about 1% to about 8% Methocel™ A4M; (f) about 2% to about 40% polyethylene glycol 400; (g) about 10.5% of hydrocodone or oxycodone; and optionally (h) about 0.25% BHT; and (i) about 0.1% BHA; wherein the matrix is resistant to tampering and has controlled release properties; the matrix being encapsulated in a soft capsule shell comprising: (j) about 25% to about 50% gelatin; (k) about 15% to about 25% glycerol; (l) about 20% to about 40% water; and (m) optionally, an opacifying agent, a coloring agent, a pharmaceutical excipient, or combination thereof. In one aspect, the tamper resistant controlled release matrix further comprises a peripherally acting mu-opioid receptor antagonist comprising naloxone, methyl naltrexone, or naltrexone. In another aspect, the weight percentage ratio of naloxone, methyl naltrexone or naltrexone to hydrocodone or oxycodone is about 15:1 to about 1:18. In another aspect, the weight percentage ratio of naloxone to hydrocodone or oxycodone is about 1:2.

Another embodiment described herein is a tamper resistant oral pharmaceutical composition comprising a tamper resistant controlled release matrix comprising: (a) about 30% to about 70% soybean oil; (b) about 1% to about 7% Ethocel™ 20 cP; (c) comprises about 0% to about 10% bee's wax; (d) about 0% to about 10% carnauba wax; (e) about 1% to about 30% Methocel™ K100M; (f) about 2% to about 40% polyethylene glycol 400; (g) about 10.5% of hydrocodone or oxycodone; and optionally (h) about 0.25% BHT; and (i) about 0.1% BHA; wherein the matrix is resistant to tampering and has controlled release properties; the matrix being encapsulated in a soft capsule shell comprising: (j) about 25% to about 50% gelatin; (k) about 15% to about 25% glycerol; (l) about 20% to about 40% water; and (m) optionally, an opacifying agent, a coloring agent, a pharmaceutical excipient, or combination thereof. In one aspect, the tamper resistant controlled release matrix further comprises a peripherally acting mu-opioid receptor antagonist comprising naloxone, methyl naltrexone, or naltrexone. In another aspect, the weight percentage ratio of naloxone, methyl naltrexone or naltrexone to hydrocodone or oxycodone is about 15:1 to about 1:18. In another aspect, the weight percentage ratio of naloxone to hydrocodone or oxycodone is about 1:2.

Another embodiment described herein is a tamper resistant oral pharmaceutical composition comprising a tamper resistant controlled release matrix comprising: (a) about 30% to about 70% soybean oil; (b) about 1% to about 7% Ethocel™ 20 cP; (c) about 0% to about 7% bee's wax; (d) about 0% to about 7% carnauba wax; (e) about 1% to about 8% Methocel™ A4M; (f) about 2% to about 40% polyethylene glycol 400; (g) about 10.5% of hydrocodone or oxycodone; (h) optionally, about 5.25% of naloxone; and optionally (i) about 0.25% BHT; and (j) about 0.1% BHA; wherein the matrix is resistant to tampering and has controlled release properties; the matrix being encapsulated in a soft capsule shell comprising: (k) about 25% to about 50% gelatin; (l) about 15% to about 25% glycerol; (m) about 20% to about 40% water; and (n) optionally, an opacifying agent, a coloring agent, a pharmaceutical excipient, or combination thereof.

Another embodiment described herein is a tamper resistant oral pharmaceutical composition comprising a tamper resistant controlled release matrix comprising: (a) about 30% to about 70% soybean oil; (b) about 1% to about 7% Ethocel™ 20 cP; (c) about 0% to about 7% bee's wax; (d) about 0% to about 7% carnauba wax; (e) about 1% to about 30% Methocel™ K100M; (f) about 2% to about 40% polyethylene glycol 400; (g) about 10.5% of hydrocodone or oxycodone; (h) optionally, about 5.25% of naloxone; and optionally (i) about 0.25% BHT; and (j) about 0.1% BHA; wherein the matrix is resistant to tampering and has controlled release properties; the matrix being encapsulated in a soft capsule shell comprising: (k) about 25% to about 50% gelatin; (l) about 15% to about 25% glycerol; (m) about 20% to about 40% water; and (n) optionally, an opacifying agent, a coloring agent, a pharmaceutical excipient, or combination thereof.

Another embodiment described herein is a method for treating, reducing the symptoms or onset of, or prophylaxis of pain stemming from diabetic neuropathy, chronic arthritis, osteoarthritis, rheumatoid arthritis, acute tendonitis, bursitis, headaches, migraines, chronic neuropathies, shingles, premenstrual symptoms, sports injuries, malignancy, radiculopathy, sciatica/sciatic pain, sarcoidosis, necrobiosis, lipoidica or granuloma annulare comprising administering to a subject in need thereof a pharmaceutical composition as described herein. In one aspect, the administration is sufficient to achieve a reduction of pain relative to baseline in the subject without substantially inducing one or more of opioid induced bowel disfunction (OIBD) comprising constipation (opioid induced constipation; OIC), anorexia, nausea and vomiting, gastro-oesophageal reflux, delayed digestion, abdominal pain, flatulence, bloating, hard stools, incomplete evacuation, or straining during bowel movements.

Another embodiment described herein is a method for delivering about a 10 mg to about a 80 mg dose of oxycodone or about a 10 mg to about a 80 mg dose of hydrocodone comprising administering to a subject a pharmaceutical composition comprising oxycodone or hydrocodone and other pharmaceutically acceptable excipients in a tamper resistant matrix in a soft gel capsule, the method capable of achieving one or more of the following pharmacokinetic parameters: (a) a mean plasma oxycodone $T_{max}$ of about 1 hours to about 8 hours; (b) a mean plasma oxycodone $C_{max}$ of about 10 ng/mL to about 150 ng/mL; (c) a mean plasma oxycodone $AUC_{0 \to \infty}$ of about 100 h·mg/L to about 1000 h·mg/L; or (d) a mean plasma hydrocodone $T_{max}$ of about 3 hours to about 8 hours; (e) a mean plasma hydrocodone $C_{max}$ of about 10 ng/mL to about 120 ng/mL; (f) a mean plasma hydrocodone $AUC_{0 \to \infty}$ of about 100 h·mg/L to about 1600 h·mg/L. In one aspect, the method further comprises delivering a dose of a peripherally acting mu-opioid receptor antagonist comprising naloxone, methyl naltrexone, or naltrexone. In another aspect, the weight percentage ratio of naloxone methyl naltrexone or naltrexone to hydrocodone or oxycodone is about 15:1 to about 1:18. In another aspect, the weight percentage ratio of naloxone to hydrocodone or oxycodone is about 1:2. In another aspect, the administration is sufficient to achieve a reduction of pain relative to baseline in the subject without substantially inducing one or more of opioid induced bowel disfunction (OIBD) comprising constipation (opioid induced constipation), anorexia, nausea and vomiting, gastro-oesophageal reflux, delayed digestion, abdominal pain, flatulence, bloating, hard stools, incomplete evacuation or straining during bowel movements. In one aspect, the administration provides an improvement of bowel function during pain therapy, comprising an improvement of the mean bowel function score of at least about 5, at least about 8, at least about 10, or at least about 15 after steady state administration to human patients, wherein the mean bowel function score is measured with a numerical analog scale ranging from 0 to 100. In another aspect, the pharmaceutical composition comprises a soft capsule. In another aspect described herein, the pharmaceutical composition exhibits an in vitro dissolution rate at pH 6.8, of about 50% after about 60 minutes to about 480 minutes. In another aspect described herein, the pharmaceutical composition exhibits an in vitro dissolution rate under boiling conditions of less than about 20% to about 80% after about 5 minutes to about 120 minutes. In another aspect described herein, the pharmaceutical composition exhibits an in vitro dissolution rate in an aqueous alcohol solution or distilled water of less than about 50% after about 280 minutes to about 1440 minutes.

Another embodiment described herein is a method for retarding the extraction an active pharmaceutical ingredient from a pharmaceutical composition by means of crushing, grating, grinding, cutting, solvating, or dissolving the matrix comprising: providing a pharmaceutical composition described herein, wherein the composition is resistant to crushing, grating, grinding, cutting, solvation, or dissolution. In one aspect described herein, the pharmaceutical composition comprises a soft capsule as described herein.

Another embodiment described herein is a kit for dispensing the abuse deterrent oral pharmaceutical composition described herein comprising: (a) at least one soft capsule comprising an abuse deterrent controlled release matrix comprising an active pharmaceutical ingredient; (b) at least one receptacle comprising a tamper evident, moisture proof packaging that reduces the ability of removing the oral pharmaceutical composition comprising blister or strip packs, aluminum blister, transparent or opaque polymer blister with pouch, polypropylene tubes, colored blister materials, tubes, bottles, and bottles optionally containing a child-resistant feature, optionally comprising a desiccant, such as a molecular sieve or silica gel; (c) optionally, an insert comprising instructions or prescribing information for the active pharmaceutical ingredient.

DETAILED DESCRIPTION

Figure 1:
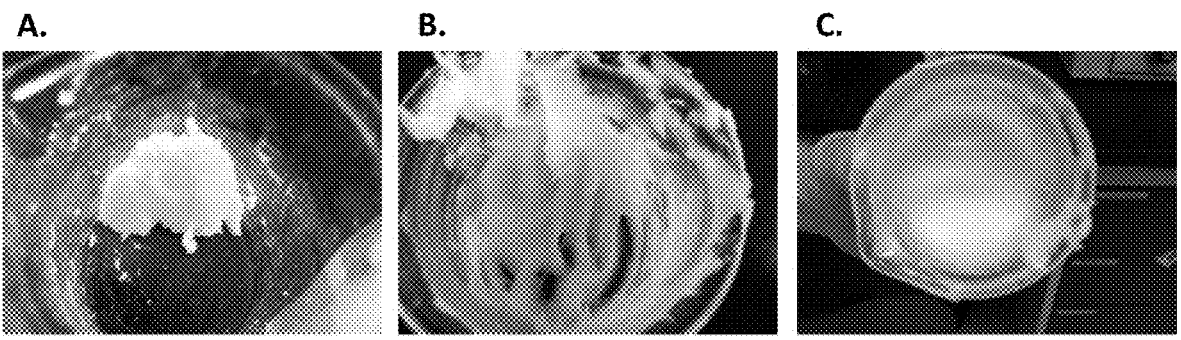
FIG. 1. Representative images of abuse deterrent matrices; (A) is the hydrophilic phase, (B) is the gelled phase, and (C) is the final mixture prior to encapsulation.

Described herein are abuse deterrent controlled release pharmaceutical compositions. The pharmaceutical compositions described herein provide abuse deterrent matrices and methods for preparation thereof. Also described herein are compositions and methods for manufacturing soft capsules comprising abuse deterrent controlled release pharmaceutical matrices. In some embodiments described herein, the soft capsule is an enteric soft capsule.

The term "abuse deterrent," or "tamper resistant" as used herein, refers to a pharmaceutical composition that is resistant to tampering or accessing the active pharmaceutical ingredient for recreational drug use or drug abuse.

The phrase "recreational drug use," as used herein, refers to the voluntary use of an active pharmaceutical agent or drug for a non-medical purpose to induce an effect, such as pleasure, satisfaction, euphoria, dissociation, or to enhance an experience.

The term "drug abuse," as use herein, refers to the habitual, compulsive, or recurrent use of an active pharmaceutical agent or drug, often despite negative consequences.

The term "tampering," as used herein, refers to any kind of actual or attempted physical manipulation or interference that may result in particle size reduction of a pharmaceutical composition. Tampering, as used herein also includes any actual or attempted dissolution or extraction of active pharmaceutical ingredients using solvents. Compositions that are resistant to physical tampering are formulated in such a way that the composition cannot readily reduced to a form that is suitable for abuse, such as, for example, injection or snorting, because the tablet cannot easily be ground, grated, dissolved, extracted, and the like at any temperature. Examples of physical tampering include, but are not limited to, crushing, grinding, grating, cutting, crisping, and other methods of particle size reduction. Dissolution tampering includes actual or attempted actions to dissolve or extract active pharmaceutical ingredients using aqueous or organic solvents such as water, ethanol, isopropanol, ethyl acetate, acetone, ether, or the like, at any temperature including boiling. Tampering, as used herein, includes "dose dumping."

The term "dose dumping" or "dumping" as used herein refers to the rapid release of the entire amount or a significant fraction of an active pharmaceutical ingredient or drug. Drug abusers often intentionally pursue dumping of a drug from the dosage form.

The terms "drug", "active ingredient," "active pharmaceutical ingredient," or "active pharmaceutical agent" as used herein refer to an agent, active ingredient, compound, or substance, compositions, or mixtures thereof, that provide a pharmacological, often beneficial, effect. Reference to a specific active ingredient includes, where appropriate, the active ingredient and any of its pharmaceutically acceptable salts or esters.

The terms "dosage" or "dose" denote any form of the active ingredient formulation that contains an amount sufficient to produce a therapeutic effect with a single administration. The dosage form used herein is for oral administration. The preferred oral dosage forms are soft capsules or enteric soft capsules.

The terms "active pharmaceutical ingredient load" or "drug load" as used herein refers to the quantity (mass) of the active pharmaceutical ingredient comprised in a single soft capsule fill.

The term "formulation" or "composition" as used herein refers to the active pharmaceutical ingredient or drug in combination with pharmaceutically acceptable excipients. This includes orally administrable formulations as well as formulations administrable by other means.

The term "titration" as used herein refers to the incremental increase in drug dosage to a level that provides the optimal therapeutic effect.

The term "controlled release" as used herein refers to a composition that does not immediately releases an active ingredient. "Controlled release" as used herein encompasses the terms "modified release," "sustained release," "extended release," and "delayed release."

The term "delayed release" as used herein refers to a composition that releases an active ingredient according to a desired profile over an extended period under physiological conditions or in an in vitro test. By "extended period" it is meant a continuous period of time of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours about 24 hours; or even longer.

The term "modified release" as used herein refers to a composition that releases an active ingredient at a slower rate than does an immediate release formulation under physiological conditions or in an in vitro test.

The term "sustained" release as used herein refers to a composition that releases an active ingredient over an extended period of time, for example minutes, hours, or days, such that less than all the active ingredient is released initially. A sustained release rate may provide, for example, a release of a certain specified amount of a drug or active ingredient from a dosage form, over a certain period, under physiological conditions or in an in vitro test.

The term "extended release" as used herein refers to a composition that releases an active ingredient over an extended period, such as of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours about 24 hours; or even longer; specifically over a period of at least 18 hours under physiological conditions or in an in vitro assay.

As used herein, the phrase "abuse deterrent controlled release" refers to a pharmaceutical composition comprising components or a formulation that prevents liberation of the active pharmaceutical ingredient(s) from the composition for potential abuse or dose dumping and the composition provides controlled release delivery of the active pharmaceutical ingredient upon ingestion of the composition by a subject.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs, and is expressed in units of hours (h) or minutes (min), as applicable.

The term "$AUC_{0 \to \tau}$" as used herein refers to area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0 \to 12}$ as used herein refers to the area under the concentration versus time curve from 0 to 12 hours.

The term "$AUC_{0 \to \infty}$" as used herein refers to the area under the blood (plasma, serum, or whole blood) concentration versus time curve from time 0 hours to infinity, and is expressed in units of h·mg/L or h·ng/mL, as applicable.

The term "$AUC_{overall}$" as used herein refers to the combined area under the blood (plasma, serum, or whole blood) concentration versus time curve, and is expressed in units of h·mg/L (or h·ng/mL) for at least one or more doses of the pharmaceutical compositions described herein. In one aspect, the "$AUC_{overall}$" refers to the combined area under the blood concentration versus time curve for at least two doses of the pharmaceutical compositions described herein.

The term "treating" refers to administering a therapy in an amount, manner, or mode effective to improve a condition, symptom, or parameter associated with a disorder.

The term "prophylaxis" refers to preventing or reducing the progression of a disorder, either to a statistically significant degree or to a degree detectable to one skilled in the art.

The term "substantially" as used herein means to a great or significant extent, but not completely.

The term "about" as used herein refers to any values, including both integers and fractional components that are within a variation of up to ±10% of the value modified by the term "about." For example, the phrase "about 50%" is equivalent to any value ≈50±10%, e.g., 44.6%, 45%, 46%, 47%, 48%, 49%, 49.5%, 50%, 50.3%, 51%, 52%, 53%, 54%, 55%, inter alia.

As used herein, "a" or "an" means one or more unless otherwise specified.

Terms such as "include," "including," "contain," "containing," "has," or "having," and the like, mean "comprising."

The term "or" can be conjunctive or disjunctive.

Described herein are pharmaceutical compositions comprising abuse deterrent controlled release matrices comprising active pharmaceutical ingredients. The matrix is structured to prevent extraction of the active pharmaceutical ingredients.

In one embodiment, the pharmaceutical composition described herein comprises a soft capsule comprising an abuse deterrent controlled release matrix comprising an active pharmaceutical ingredient. In one embodiment, the active pharmaceutical ingredient is an analgesic. In another embodiment, the active pharmaceutical ingredient is an opioid analgesic.

In another embodiment, the soft capsule comprising a matrix can provide controlled release properties. Such controlled release matrix fills are described in International Patent Application Publication No. WO 2005/009409 and WO 2006/096580, U.S. Patent Application Publication Nos. US 2006/0115527 and US 2007/0053868, and U.S. Pat. Nos. 8,293,270 and 8,333,989, each of which are incorporated by reference herein for such teachings. In one aspect, the soft capsule and matrix can be configured to provide controlled release, extended release, sustained release, delayed release, or combinations thereof.

In other embodiments, the pharmaceutical composition described herein comprises abuse deterrent properties. These abuse deterrent properties reduce the likelihood that the active pharmaceutical ingredient can be extracted from the composition through mechanisms, including but not limited to crushing, grating, grinding, or cutting of the capsule to expose the matrix thereby facilitating solvation or extraction of the active pharmaceutical ingredient. In addition, the abuse deterrent properties reduce the likelihood that the active pharmaceutical ingredient can be extracted from the composition by dissolving or extracting in ethanol solutions of about 1% to about 50%, dissolving in solutions having pH values from about 1 to about 12, or dissolving in household chemical compositions, including water, coffee, vinegar, cola, milk, ethanol, isopropanol, acetone, ethyl acetate, or other common solvents. In addition, the abuse deterrent properties further reduce the likelihood that the active pharmaceutical ingredient can be extracted by boiling in water or ethanol solutions.

In other embodiments described herein, the matrix comprises a lipid or lipophilic vehicle that provides a suspension or a solution of the active pharmaceutical ingredient. In one aspect, a soft capsule comprising an active pharmaceutical ingredient provides controlled release of the active pharmaceutical ingredient.

In other embodiments described herein, the pharmaceutical composition provides matrix fills for the active pharmaceutical ingredient, or derivatives thereof, based on lipids or lipophilic materials. The matrices described herein have a hydrophobic (lipophilic) surface in contact with a hydrophilic soft capsule shell to minimize any potential shell-fill interactions, such as when the soft capsules are filled with hydrophilic materials. In one embodiment described herein are methods for manufacturing matrix fills comprising an abuse deterrent controlled release matrix comprising an active pharmaceutical ingredient in a soft capsule in the form of a suspension, where part or all of the active pharmaceutical ingredient is suspended within the matrix. In one embodiment described herein is a soft capsule having a shell and an abuse deterrent controlled release matrix fill, wherein the matrix includes an active pharmaceutical ingredient suspended as solid particles within the lipophilic vehicle.

In one embodiment described herein, an exemplary abuse deterrent controlled release matrix has the composition of Table 1, including all possible iterations of the specified ranges that provide 100% for the total weight percentage, including or excluding the optional colorings, flavorings, or pharmaceutically acceptable excipients.

TABLE 1

Exemplary Abuse Deterrent Controlled Release Matrix Composition

| Component | Exemplary Components | Composition Range (%) |
| --- | --- | --- |
| Liquid lipophilic vehicle(s) | Soybean oil | 35-75 |
| Semisolid lipid vehicle | Bee's wax, carnauba wax | 0-7 |
| Organogelator | Ethyl cellulose | 2-25 |
| Hydrophilic Polymer | Methyl cellulose, hydroxypropyl methylcellulose, poly(ethylene) oxide | 2-25 |
| Hydrophilic vehicle | Polyethylene glycol | 2-20 |
| Disintegrant | Microcrystalline cellulose | 0-5 |
| Anti-oxidant | BHT, BHA | 0-0.5 |
| Active pharmaceutical ingredient(s) | Oxycodone, hydrocodone, tapentadol | 1-35 |

In another embodiment, the lipid or lipophilic vehicle can be a liquid lipophilic vehicle, a semisolid lipophilic vehicle, or combinations thereof. Suitable lipid or lipophilic vehicles include mineral oil; light mineral oil; natural oils (e.g., vegetable, corn, canola, sunflower, soybean, olive, coconut, cocoa, peanut, almond, cottonseed, persic, sesame, squalane, castor, cod liver, etc) hydrogenated vegetable oil; partially hydrogenated oils; bee's wax (beeswax); polyethoxylated bee's wax; paraffin; normal waxes; medium chain medium chain monoglycerides, diglycerides and triglycerides; higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol mono-oleate esters; glycerol mono-caprate; glyceryl monocaprylate; propylene glycol dicaprylate; propylene glycol monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyl dodecanol; myristyl alcohol; isopropyl myristate, isopropyl palmitate, stearic acid, stearyl alcohol, and others known in the art.

In one embodiment, the lipid or lipophilic vehicle comprises both a liquid lipophilic vehicle and a semisolid lipophilic vehicle. In one embodiment, the liquid lipid or lipophilic vehicle can be olive oil, soybean oil, sunflower oil, canola oil, palmitoleic acid, oleic acid, myristoleic acid, linoleic acid, arachidonic acid, paraffin oil, or mineral oil. In another embodiment, the semi-solid lipophilic vehicle can be a polyethylene glycol glyceride ester, paraffin wax, carnauba wax, or bee's wax. In another embodiment, the semi-solid lipophilic vehicle can be Gelucire® 33/01, Gelucire® 37/02, Gelucire® 39/01, Gelucire® 43/01, Gelucire® 44/14, Gelucire® 50/02, Gelucire® 50/13, Gelucire® 53/10, or Gelucire® 62/02. In another embodiment, the Gelucire® semisolid lipid vehicle has a HLB value of about 1 and a melting point of about 43. In one aspect, the liquid lipid or lipophilic vehicle is soybean oil. In another aspect, the semisolid lipid or lipophilic vehicle comprises a wax. In another aspect, the semisolid lipid or lipophilic vehicle comprises bee's wax. In another aspect, the semisolid lipid or lipophilic vehicle comprises carnauba wax. In another aspect, the semisolid lipid or lipophilic vehicle comprises a mixture of bee's wax and carnauba wax.

In one embodiment, the matrix comprises a surfactant. The surfactant can have a hydrophilic/lipophilic balance (HLB) value between about 1 and about 25 and a melting point between about 25° C. and about 70° C. The HLB characteristic of surfactants can be determined in accordance with "Physical Pharmacy: Physical Chemical Principles in the Pharmaceutical Sciences," Fourth Edition, pp. 371-373, A. Martin, Ed., Lippincott Williams & Wilkins, Philadelphia (1993). Suitable surfactants include: glyceryl monocaprylate (e.g., Capmul® MCM), Pluronic® 10R5, Pluronic® 17R2, Pluronic® 17R4, Pluronic® 25R2, Pluronic® 25R4, Pluronic® 31R1, Pluronic® F 108, Pluronic® F. 108 NF, Pluronic® F. 108, Pluronic® F. 108NF, Poloxamer 338, Pluronic® F 127, Pluronic® F. 127 NF, Pluronic® F. 127 NF 500 BHT Prill, Pluronic® F. 127 NF Prill, Poloxamer 407, Pluronic® F. 38, Pluronic® F. 38 Pastille, Pluronic® F. 68, Pluronic® F 68 LF Pastille, Pluronic® F 68 NF, Pluronic® F 68 NF Prill, Poloxamer 188, Pluronic® F. 68 Pastille, Pluronic® F. 77, Pluronic® F 77 Micropastille, Pluronic® F. 87, Pluronic® F. 87 NF, Pluronic® F 87 NF Prill, Poloxamer 237, Pluronic® F 88, Pluronic® F. 88 Pastille, Pluronic® F. 98, Pluronic® L 10, Pluronic® L 101, Pluronic® L 121, Pluronic® L 31, Pluronic® L 35, Pluronic® L 43, Pluronic® L 61, Pluronic® L 62, Pluronic® L 62 LF, Pluronic® L 62D, Pluronic® L 64, Pluronic® L 81, Pluronic® L 92, Pluronic® N 3, Pluronic® P 103, Pluronic® P 104, Pluronic® P 105, Pluronic® P 123 Surfactant, Pluronic® P 65, Pluronic® P 84, Pluronic® P 85, Adogen® 464, Alkanol® 6112, Brij® 52, Brij® 93, Brij® S2, Brij® S, Brij® 58, Brij® C10, Brij® L4, Brij® O10, Brij® O10, BRIJ® O20, Brij® S10, Brij® S20, ethylenediamine tetrakis(ethoxylate-block-propoxylate) tetrol, ethylenediamine tetrakis(ethoxylate-block-propoxylate) tetrol, ethylenediamine tetrakis(propoxylate-block-ethoxylate) tetrol, IGEPAL® CA-210, IGEPAL® CA-520, IGEPAL® CA-720, IGEPAL® CO-520, IGEPAL® CO-630, IGEPAL® CO-720, IGEPAL® CO-890, IGEPAL® DM-970, MERPOL® DA, MERPOL® HCS, MERPOL® OJ, MERPOL® SE, MERPOL® SH, MERPOL® A, Poly(ethylene glycol) sorbitan tetraoleate, poly(ethylene glycol) sorbitol hexaoleate, poly(ethylene glycol) (12), poly(ethylene glycol) (18), polyethylene-block-poly(ethylene glycol), sorbitan monopalmitate, 2,4,7,9-tetramethyl-5-decyne-4,7-diol ethoxylate, Nonidet™ P-40, Triton™ N-101, Triton™ X-100, Triton™ X-114, Triton™ X-405, TWEEN® 20, TWEEN® 40, TWEEN® 60, TWEEN® 85, Zonyl® FS-300, or Zonyl® FSN. In one embodiment, the surfactant comprises Pluronic® F127, Tween® 80, Span® 80, IGEPAL®, Triton™ X-100, or Capmul® MCM.

In another embodiment, the abuse deterrent matrix comprises one or more organogelator controlled release polymers. An organogel is a cross-linked fibrous three-dimensional network. These types of gels are formed in a liquid organic phase via the covalent polymerization of monomers through reactive groups or aggregation and self-assembly of monomers. The assembly of these monomers occurs through extensive van der Waals forces, hydrogen bonding, or dipole-dipole interactions, among others. At or near the gel-point, the network is strong enough that the liquid solution is gel-like with physical rheological properties. In general, organogelators relying on hydrogen bonding are amino acids, amides, urea moieties, and carbohydrates or carbohydrate derivatives. Covalent or chemical-type organogelators typically are anthracene, anthraquinone, or steroid-based molecules.

Potential suitable organogelators for the abuse deterrent matrices described herein include but are not limited to the simplest n-alkanes ($C_{24-36}$), which function to gel other short alkanes, such as hexadecane; substituted fatty acids (e.g., 12-hydroxyoctadecanoic acid or 1, 3:2,4-di-O-benzylidene-D-sorbitol (D-DBS), steroids and derivatives; anthryl derivatives (e.g., 2,3-bis-n-decyloxyanthracene); macrocyclic gelators (e.g., calixarenes); aromatic linked steroidal groups; cyclodipeptides; bisurea compounds; bisamides; bolaform amides; alkyl perfluoroalkanamides; carbohydrate derivatives, cellulose derivatives, such as ethyl cellulose; perfluoroalkanes and carbon dioxide; methyl 2,6,-diisocyanatohexanoate and alkylamines; primary alkyl amines; any light-responsive gelator; oxadiazole-based benzene; 1,3,5-tricarboxamide; cobalt (II) triazole complexes; and fatty acid derivatives of L-alanine; sorbitan monostearate based organogelators; metha methacrylate based organogels (e.g., mixtures of Eudragit® and polyhydric alcohols); gelatin microemulsions; lecithin based organogels; poloxamer and lecithin; or mixtures or combinations thereof. Additional organogelators are described by Murdan, *Expert. Opin. Drug Deliv.* 2(3): 489-505 (2005), which is incorporated by reference herein for its specific teachings thereof.

Gelation of organogels occurs at a certain temperature depending on the polymer. Typically, the solution is heated, which allows for the dissolution of the gelator polymer into an organic liquid and subsequent gelation as temperature drops. The gel-point temperature can be modified by the addition of different solvents or surfactants.

A common method for extracting abuse prone drugs is by boiling the composition. Thus, in some embodiments, the abuse deterrent matrices described herein reduce the percentage of released active pharmaceutical ingredient released during boiling conditions. Without being bound by any theory, it is thought that the extensive three dimensional network formed by the organogelator polymers in the abuse deterrent controlled release matrices described herein slows the release of active pharmaceutical ingredients under boiling conditions. Thus, in some embodiments described herein, suitable organogelator molecules for the controlled release matrices described herein gel in boiling temperatures from about 95° C. to about 120° C.

Most organogelators, including the principally used low molecular weight organogelators, are thermoreversible and lose their rheological properties upon extensive heat. Other organogelators react with active pharmaceutical ingredients and prevent the formation of a strong gel network or are water-soluble. Thus, it was uniquely found that the ethyl ether derivative of cellulose, ethyl cellulose, is water insoluble and forms an excellent organogel at a boiling temperature of about 100° C. in a soft gelatin capsule comprising an active pharmaceutical ingredient. Further, it was found that the gel strength and gel-point temperature could be further customized by the level of ethoxylation or with the addition of surfactants or different molecular weight ethyl cellulose. Ethyl cellulose is available in a variety of molecular weights denoted as a centipoise viscosity value (cP), and useful ethyl cellulose polymers have a cP value of about 3 cP to about 350 cP.

Thus, in another embodiment described herein, the abuse deterrent matrix comprises one or more organogelators including but not limited to ethylcellulose (e.g., Ethocel™; Dow Chemical). In one aspect, ethyl cellulose has viscosity of about 2 to about 100 cP. In another aspect, ethyl cellulose has a viscosity of about 4 cP, about 8 cP, about 12 cP, about 16 cP, about 20 cP, about 24 cP, about 28 cP, about 32 cP, about 36 cP, about 40 cP, about 48 cP, about 52 cP, about 56 cP, about 60 cP, about 64 cP, about 68 cP, about 72 cP, about 76 cP, about 80 cP, about 84 cP, about 88 cP, about 92 cP, about 96 cP, or about 100 cP. In another aspect, ethyl cellulose has a cP of about 4. In another aspect, ethyl cellulose has a viscosity of about 20 cP.

In another embodiment, the abuse deterrent matrix comprises a disintegrant excipient. Disintegrants, useful in the abuse deterrent matrices described herein, include any polymer, which expands in aqueous solution, which causes a tablet or capsule to burst and facilitate dissolution. Exemplary, non-limiting disintegrants comprise crosslinked polyvinylpyrrolidone (e.g., crospovidone), crosslinked sodium carboxymethyl cellulose (croscarmellose sodium) carboxymethyl cellulose calcium, cysteine HCl, modified starches (e.g., sodium starch glycolate), cellulose, calcium silicate, silicon dioxide, alginic acid, sodium alginate, citric acid, microcrystalline cellulose, polyoxy stearate, sodium croscarmellose, sodium lauryl sulfate, or a mixture or combination thereof. In one aspect, the disintegrant comprises microcrystalline cellulose.

In another embodiment, the abuse deterrent matrix comprises one or more hydrophilic vehicles. Suitable, non-limiting hydrophilic vehicles comprise hydro-alcohols including propylene glycol, or polyethylene glycols of a molecular weight ranging from about 200 to about 8,000 ($M_N$, number average molecular weight) or a mixture or combination thereof. In one aspect, the hydrophilic vehicle comprises polyethylene glycol. In another aspect, the hydrophilic vehicle comprises polyethylene glycol 400.

In another embodiment, the abuse deterrent matrix comprises one or more hydrophilic polymers. Suitable, non-limiting hydrophilic polymers comprise methylcellulose, hydroxypropylmethyl cellulose, hydroxypropyl cellulose, hydroxypropyl methylcellulose, hydroxyethyl cellulose, hydroxymethyl cellulose, polymethylmethacrylate, polyhydroxyethylmethacrylate, polyvinyl pyrrolidone, polyvinylpyrrolidone, copovidone, polyethylene oxide such as POLYOX™ 100,000-8,000,000 MW, polyvinyl alcohol, a copolymer of polyvinylpyrrolidone and polyvinyl acetate, or combinations thereof. In one aspect, the hydrophilic polymers comprises one or more of Methocel™ K100 Premium LV CR, K4M Premium CR, K15M Premium CR, K100 Premium CR, E4M Premium CR, E10M Premium CR, or E4M Premium (Dow Chemical Co.); POLYOX™, CELLOSIZE™, or WALOCEL™ CRT. Without being bound by any theory, it is thought that water coming into contact with the hydrophilic polymer, such as methylcellulose or hydroxypropylmethylcellulose, causes it to expand or swell and further impede the release of active pharmaceutical ingredients from the matrix. In one aspect, the hydrophilic polymer comprises methylcellulose. In one aspect, the hydrophilic polymer comprises hydroxypropylmethylcellulose. In another aspect, the hydrophilic polymer comprises a viscosity of about 50 cP to about 100,000 cP. In another aspect, hydrophilic polymer comprises a viscosity of about 50 cP, about 100 cP, about 200 cP, about 300 cP, about 400 cP, about 500 cP, about 750 cP, about 1,000 cP, about 1,500 cP, about 2,000 cP, about 2,500 cP, about 3,000 cP, about 3,500 cP, about 4,000 cP, about 4,500 cP, about 5,000 cP, about 6,000 cP, about 7,000 cP, about 8,000 cP, about 9,000 cP, or about 10,000 cP, about 15,000 cP, about 20,000 cP, about 30,000 cP, about 40,000 cP, about 50,000 cP, about 60,000 cP, about 70,000 cP, about 80,000 cP, about 90,000 cP, about 100,000 cP, greater than 100,000 cP, or even greater. In one aspect, methylcellulose has a viscosity of about 4,000 cP (e.g., Methocel™ A4M). In another aspect, hydroxypropylmethylcellulose has a viscosity of about 100,000 cP (e.g., Methocel™ K100M).

In another embodiment, the hydrophilic polymer may comprise a high molecular weight polyethylene oxide. As described herein, high molecular weight polyethylene oxide polymers have an approximate molecular weight of at least about 100,000 to about 10,000,000 or greater. In one aspect, the hydrophilic polymer may comprise a high molecular weight polyethylene oxide having a molecular weight of about 600,000 to about 10,000,000, including each integer within the specified range. In another aspect, the hydrophilic polymer may comprise a high molecular weight polyethylene oxide having a molecular weight of about 5,000,000 to about 10,000,000, including each integer within the specified range. In another aspect, the hydrophilic polymer may comprise a high molecular weight polyethylene oxide having a molecular weight of about 4,000,000 to about 7,000,000, including each integer within the specified range. In another aspect, the hydrophilic polymer may comprise a high molecular weight polyethylene oxide having a molecular weight of about 600,000, about 700,000, about 800,000, about 900,000, about 1,000,000, about 2,000,000, about 3,000,000, about 4,000,000, about 5,000,000, about 6,000,000, about 7,000,000, about 8,000,000, about 9,000,000 or about 10,000,000. In another aspect, the hydrophilic polymer may comprise a high molecular weight polyethylene oxide having a molecular weight of about 4,000,000. In another aspect, the hydrophilic polymer may comprise a high molecular weight polyethylene oxide having a molecular weight of about 5,000,000. In another aspect, the hydrophilic polymer may comprise a high molecular weight polyethylene oxide having a molecular weight of about 7,000,000.

The molecular weight measurements of hydrophilic polymers may be approximated using rheological measurements using a viscometer. For example, a hydrophilic polymer is considered to have an approximate molecular weight of 600,000 when a 5% (by wt) aqueous solution of polyethylene oxide using a Brookfield viscometer Model RVF, spindle No. 2, at 2 rpm, at 25° C. shows a viscosity range of 30 to 50 mPa s (cP). A hydrophilic polymer is considered to have an approximate molecular weight of 1,000,000 when a 2% (by wt) aqueous solution of A hydrophilic polymer using a Brookfield viscometer Model RVF, spindle No. 1, at 10 rpm, at 25° C. shows a viscosity range of 400 to 800 mPa s (cP). A hydrophilic polymer is considered to have an approximate molecular weight of 2,000,000 when a 2% (by wt) aqueous solution of A hydrophilic polymer using a Brookfield viscometer Model RVF, spindle No. 3, at 10 rpm, at 25° C. shows a viscosity range of 2000 to 4000 mPa s (cP). A hydrophilic polymer is considered to have an approximate molecular weight of 4,000,000 when a 1% (by wt) aqueous solution of A hydrophilic polymer using a Brookfield viscometer Model RVF, spindle No. 2, at 2 rpm, at 25° C. shows a viscosity range of 1650 to 5500 mPa s (cP). A hydrophilic polymer is considered to have an approximate molecular weight of 5,000,000 when a 1% (by wt) aqueous solution of A hydrophilic polymer using a Brookfield viscometer Model RVF, spindle No. 2, at 2 rpm, at 25° C. shows a viscosity range of 5500 to 7500 mPa s (cP). A hydrophilic polymer is considered to have an approximate molecular weight of 7,000,000 when a 1% (by wt) aqueous solution of A hydrophilic polymer using a Brookfield viscometer Model RVF, spindle No. 2, at 2 rpm, at 25° C. shows a viscosity range of 7500 to 10,000 mPa s (cP). A hydrophilic polymer is considered to have an approximate molecular weight of 8,000,000 when a 1% (by wt) aqueous solution of A hydrophilic polymer using a Brookfield viscometer Model RVF, spindle No. 2, at 2 rpm, at 25° C. shows a viscosity range of 10,000 to 15,000 mPa s (cP).

In another embodiment, the one or more hydrophilic polymers comprises from about 1% to about 50% of the matrix fill mass, including all integers within the specified range. In one aspect, the one or more hydrophilic polymer s comprises from about 1% to about 30% of the matrix fill mass, including all integers within the specified range. In another aspect, the one or more hydrophilic polymers comprises from about 25% to about 40% of the matrix fill mass, including all integers within the specified range. In another aspect, the one or more hydrophilic polymers comprises from about 25% to about 35% of the matrix fill mass, including all integers within the specified range. In another aspect, the one or more hydrophilic polymers comprises about 20%, about 25%, about 30%, about 35%, about 40%, about 45%, or about 50% of the matrix fill mass.

In another embodiment, the abuse-deterrent matrix comprises one or more antioxidants. Suitable antioxidants comprise tocopherols (e.g., alpha-tocopherol, beta-tocopherol, gamma-tocopherol, or delta-tocopherol), butylated hydroxytoluene (BHT), butylated hydroxyanisole (BHA), citric acid, ascorbic acid, phenolic diterpenes (e.g., carnosic acid, carnosol, rosmanol, epirosmanol, isorosmanol, or methyl carnosate), rosmarinic acid, eugenol, eugenyl acetate, clove bud extract, methanolic extract, tea catechins (e.g., epigallocatechin gallate, epicatechin gallate, epigallocatechin, or epicatechin), or combinations thereof.

In another embodiment, the abuse deterrent matrix can include a hydrophilic internal phase and a lipid or lipophilic external phase (water in oil) or a lipid or lipophilic internal phase and a hydrophilic external phase (oil in water). The internal phase can also be structured. A "structured" phase, as used herein, means a solid, semisolid, or a gel whose shape is relatively stable and does not usually aggregate to form a large globule. One or more structured phases provide controlled drug release and stabilize the physical state of the matrix. Without being bound to any theory, it is believed that a structured matrix impedes solvation and/or diffusion of the active pharmaceutical ingredient out of the matrix after the capsule shell dissolves.

In another embodiment, the active pharmaceutical ingredient can be dispersed in the internal phase as a suspension form. A suspension as used herein means the API does not dissolve in one of the phases and remains as a solid. In one embodiment, the active pharmaceutical ingredient is dispersed or suspended in the internal phase as a solid form.

In one embodiment described herein, the abuse deterrent matrix may comprise one or more liquid lipophilic vehicles, one or more semisolid lipid vehicles, one or more organogelators, one or more hydrophilic polymers, one or more hydrophilic vehicles, one or more anti-oxidants, one or more active pharmaceutical ingredients, optionally one or more disintegrants, and optionally one or more pharmaceutically acceptable excipients.

In one aspect, the combination of matrix fill components prevents or reduces the likelihood of extraction of an active pharmaceutical ingredient in aqueous or boiling conditions. Without being bound by any theory, it is believed that the presence of the components of the abuse deterrent matrix compositions described herein function to inhibit drug release from the pharmaceutical compositions described herein. In one aspect, a semi solid lipid vehicle (e.g., bee's wax or carnauba wax) forms a highly viscous structure and inhibits the release of active pharmaceutical ingredients from the matrix fill in aqueous conditions. In another aspect, the semi-solid lipid vehicle prevents release in an aqueous solvent (e.g., pure water or a mixture of ethanol and water) at low to middle ranges of temperatures (e.g., from about 20° C. to about 85° C.). In one aspect, the presence of a hydrophilic polymer (e.g., methylcellulose) is soluble in water demonstrating controlled release swelling properties but is insoluble in ethanol, which further helps reduce the release of an active pharmaceutical ingredient in aqueous solutions of ethanol. In one aspect, the organogelator prevents the release of active pharmaceutical ingredients at boiling or near-boiling temperatures by forming a three dimensional network, which prevents drug release at high temperatures. In one aspect, the hydrophilic vehicle enhances the release of active pharmaceutical ingredients in the stomach and gastro intestinal tract. In one aspect, the one or more optional disintegrants functions to swell and de-structure the matrix and increase the release rate of the active pharmaceutical ingredient in the stomach and gastrointestinal tract. Thus, the matrix compositions described herein permit abuse deterrence by preventing liberation of the active ingredient for injection or insufflation and prevent solvation, dissolution, or extraction of the active pharmaceutical ingredient by use of aqueous or organic solutions. Furthermore, the matrix compositions also provide controlled release delivery of the active pharmaceutical ingredient after ingestion by a subject.

In another embodiment described herein, the abuse deterrent matrix described herein prevents extraction of an active pharmaceutical ingredient through the additional means of crushing, grating, grinding, or cutting dosage forms comprising the pharmaceutical compositions described herein.

In one aspect, increasing the weight percentage of semisolid lipid vehicle, organogelator, and hydrophilic polymer in the matrix fill increases the overall viscosity of the matrix fill solution and decreases the release rate of an active pharmaceutical ingredient in aqueous solvents and aqueous solvents in boiling conditions. Conversely, in another aspect, decreasing the weight percentage of semisolid lipid vehicle, organogelator, and hydrophilic polymer decreases the overall viscosity of the matrix fill solution and decreases the release rate of an active pharmaceutical ingredient in aqueous solvents and aqueous solvents in boiling conditions. Thus, the abuse deterrent matrices described herein are compatible with a broad range of active pharmaceutical ingredients and demonstrate abuse deterrent properties.

In another embodiment, the lipid or lipophilic vehicle comprises a liquid lipid or lipophilic vehicle, a semisolid lipid or lipophilic vehicle, or combinations thereof. In one embodiment, the total lipid or lipophilic vehicle comprises one or more liquid lipid vehicles and one or more semi-solid lipid vehicles. In one embodiment, the total lipid or lipophilic vehicle comprises about 25% to about 85% of the total matrix mass, including all integers within the specified range. In some aspects, the total lipid or lipophilic vehicle comprises about 25%, about 30%, about 35%, about 40%, about 45%, about 50%, about 55%, about 60%, about 65%, about 70%, about 75%, about 80%, or about 85% of the total matrix mass.

In another embodiment, the total weight percentage of lipid or lipophilic vehicle comprises about 45% to about 55% of the total matrix mass, including all integers within the specified range. In another embodiment, the total weight percentage of lipid or lipophilic vehicle comprises about 50% to about 65% of the total matrix mass, including all integers within the specified range. In another embodiment, the total weight percentage of lipid or lipophilic vehicle comprises about 60% to about 70% of the total matrix mass, including all integers within the specified range. In one aspect, the total weight percentage of lipid or lipophilic vehicle comprises about 46% of the total matrix mass. In another aspect, the total weight percentage of lipid or lipophilic vehicle comprises about 50% of the total matrix mass. In one aspect, the total weight percentage of lipid or lipophilic vehicle comprises about 60% of the total matrix mass. In one aspect, the total weight percentage of lipid or lipophilic vehicle comprises about 65% of the total matrix mass. In another aspect, the total weight percentage of lipid or lipophilic vehicle comprises about 68% of the total matrix mass. In another aspect, the total lipid or lipophilic vehicle comprises about 70% of the total matrix mass.

In another embodiment, total weight percentage of the liquid lipid or lipophilic vehicles comprises about 20% to about 85% of the total matrix mass, including all integers within the specified range. In some aspects, total weight percentage of liquid lipid or lipophilic vehicles comprises about 20%, about 25%, about 30%, about 35%, about 40%, about 45%, about 50%, about 55%, about 60%, about 65%, about 70%, about 75%, or about 80% of the total matrix mass. In one embodiment, the total weight percentage of liquid lipid or lipophilic vehicle comprises from about 45% to about 55% of the total matrix mass, including all integers within the specified range. In one embodiment, the total weight percentage of liquid lipid or lipophilic vehicle comprises from about 55% to about 60% of the total matrix mass, including all integers within the specified range. In one embodiment, the total weight percentage of liquid lipid or lipophilic vehicle comprises from about 60% to about 65% of the total matrix mass, including all integers within the specified range. In one embodiment, the total weight percentage of liquid lipid or lipophilic vehicle comprises from about 60% to about 72% of the total matrix mass, including all integers within the specified range. In one aspect, the total weight percentage of liquid lipid or lipophilic vehicle comprises about 45% of the total matrix mass. In another aspect, the total weight percentage of liquid lipid or lipophilic vehicle comprises about 50% of the total matrix mass. In another aspect, the total weight percentage of liquid lipid or lipophilic vehicle comprises about 58% of the total matrix mass. In another aspect, the total weight percentage of liquid lipid or lipophilic vehicle comprises about 65% of the total matrix mass. In another aspect, the total weight percentage of liquid lipid or lipophilic vehicle comprises about 70% of the total matrix mass.

In another embodiment, the total weight percentage of the one or more semisolid lipid or lipophilic vehicles comprises from about 0% to about 10% of the total matrix mass, including all integers within the specified range. In another embodiment, the total weight percentage of the one or more semisolid lipid or lipophilic vehicles comprise from about 1.5% to about 5% of the total matrix mass, including all integers within the specified range. The total weight percentage of the one or more semisolid lipid or lipophilic vehicles comprise about 1%, about 2%, about 3%, about 4%, about 5%, about 6%, about 7%, about 8%, about 9%, or about 10% of the total matrix mass. In one aspect, the total weight percentage of semisolid lipid or lipophilic vehicle comprises about 1% of the total matrix mass. In one aspect, the total weight percentage of semisolid lipid or lipophilic vehicle comprises about 2% of the total matrix mass. In one aspect, the total weight percentage of semisolid lipid or lipophilic vehicle comprises about 3.5% of the total matrix mass. In one aspect, the total weight percentage of semisolid lipid or lipophilic vehicle comprises about 4.5% of the total matrix mass. In one aspect, the total weight percentage of semisolid lipid or lipophilic vehicle comprises about 6% of the total matrix mass. In one aspect, the total weight percentage of semisolid lipid or lipophilic vehicle comprises about 7% of the total matrix mass. In one aspect, no (0%) semisolid lipid or lipophilic vehicle is present in the composition.

In another embodiment, the total weight percentage of the one or more organogelators comprises from about 2% to about 25% of the total matrix mass, including all integers within the specified range. In another embodiment, the one or more organogelators comprise from about 3% to about 10% of the total matrix mass, including all integers within the specified range. In another embodiment, the one or more organogelators comprises from about 10% to about 18% of the total matrix mass, including all integers within the specified range. In one aspect, the one or more organogelators comprise about 3.5% of the total matrix mass. In one aspect, the one or more organogelators comprise about 5% of the total matrix mass. In another aspect, the one or more organogelators comprise about 7% of the total matrix mass. In another aspect, the one or more organogelators comprise about 9% of the total matrix mass. In another aspect, the one or more organogelators comprise about 11% of the total matrix mass. In another aspect, the one or more organogelators comprise about 13% of the total matrix mass. In another aspect, the one or more organogelators comprise about 25% of the total matrix mass. In one aspect, the organogelators is a hydrophobic organogelator controlled release polymer.

In another embodiment, the total weight percentage of the one or more hydrophilic polymers comprises from about 1% to about 30% of the total matrix mass, including all integers within the specified range. In another embodiment, the one or more hydrophilic polymers comprises from about 2% to about 20% of the total matrix mass, including all integers within the specified range. In another embodiment, the one or more hydrophilic polymers comprises from about 10% to about 15% of the total matrix mass, including all integers within the specified range. In one aspect, the one or more hydrophilic polymers comprise about 2.5% of the total matrix mass. In another aspect, the one or more hydrophilic polymers comprise about 5% of the total matrix mass. In another aspect, the one or more hydrophilic polymers comprise about 7% of the total matrix mass. In another aspect, the one or more hydrophilic polymers comprise about 9% of the total matrix mass. In another aspect, the one or more hydrophilic polymers comprise about 10.5% of the total matrix mass. In another aspect, the one or more hydrophilic polymers comprise about 12% of the total matrix mass. In another aspect, the one or more hydrophilic polymers comprise about 14% of the total matrix mass. In another aspect, the one or more hydrophilic polymers comprise about 15% of the total matrix mass. In another aspect, the one or more hydrophilic polymers comprise about 20% of the total matrix mass. In another aspect, the one or more hydrophilic polymers comprise about 25% of the total matrix mass.

In another embodiment, the one or more hydrophilic vehicles comprise from about 2% to about 60% of the total matrix mass, including all integers within the specified range. In another embodiment, the one or more hydrophilic vehicles comprise from about 4% to about 11% of the total matrix mass, including all integers within the specified range. In another embodiment, the one or more hydrophilic vehicles comprise from about 12% to about 20% of the total matrix mass, including all integers within the specified range. In one aspect, the one or more hydrophilic vehicles comprise about 4% of the total matrix mass. In another aspect, the one or more hydrophilic vehicles comprise about 6% of the total matrix mass. In another aspect, the one or more hydrophilic vehicles comprise about 10% of the total matrix mass. In another aspect, the one or more hydrophilic vehicles comprise about 18% of the total matrix mass. In another aspect, the one or more hydrophilic vehicles comprise about 20% of the total matrix mass. In another aspect, the one or more hydrophilic vehicles comprise about 22% of the total matrix mass. In another aspect, the one or more hydrophilic vehicles comprise about 24% of the total matrix mass. In another aspect, the one or more hydrophilic vehicles comprise about 28% of the total matrix mass. In another aspect, the one or more hydrophilic vehicles comprise about 36% of the total matrix mass.

In another embodiment, the one or more disintegrant excipients comprises from about 1% to about 5% of the total matrix mass, including all integers within the specified range. In one aspect, the one or more disintegrant excipients comprise about 1% of the total matrix mass. In another aspect, the one or more disintegrant excipients comprise about 1.5% of the total matrix mass. In another aspect, the one or more disintegrant excipients comprise about 2.5% of the total matrix mass.

In another embodiment, the matrix comprises one or more surfactants. In another embodiment, the one or more surfactants comprise from about 10% to about 20% of the total matrix mass, including all integers within the specified range. In another embodiment, the one or more surfactants comprise from about 2.5% to about 10% of the total matrix mass, including all integers within the specified range. In one aspect, the one or more surfactants comprise about 5% of the total matrix mass. In another aspect, the one or more surfactants comprise about 6.5% of the total matrix mass. In another aspect, the one or more surfactants comprise about 8.5% of the total matrix mass. In one aspect, the one or more surfactants comprise about 10% of the total matrix mass. In another aspect, the one or more surfactants comprise about 15% of the total matrix mass. In another aspect, the one or more surfactants comprise about 10% of the total matrix mass. In another aspect, the one or more surfactants comprise about 20% of the total matrix mass.

In another embodiment, one or more antioxidants comprises from about 0.1% to about 0.5% of the matrix mass, including all integers within the specified range. In one aspect, the one or more antioxidants comprise about 0.3% of the matrix mass. In another aspect, the one or more antioxidants comprise about 0.4% of the matrix mass.

In another embodiment, the total hydrophobic matrix (e.g., lipophilic vehicle and hydrophobic organogelator) comprises from about 40% to about 85% of the total matrix mass, including all integers within the specified range. In one aspect, the total hydrophobic matrix comprises about 40% of the total matrix mass. In one aspect, the total hydrophobic matrix comprises about 45% of the total matrix mass. In one aspect, the total hydrophobic matrix comprises about 50% of the total matrix mass. In one aspect, the total hydrophobic matrix comprises about 55% of the total matrix mass. In one aspect, the total hydrophobic matrix comprises about 60% of the total matrix mass. In another aspect, the total hydrophobic matrix comprises about 65% of the total matrix mass. In another aspect, the total hydrophobic matrix comprises about 70% of the total matrix mass. In another aspect, the total hydrophobic matrix comprises about 75% of the total matrix mass. In another aspect, the total hydrophobic matrix comprises about 80% of the total matrix mass.

In another embodiment, the total hydrophilic matrix (e.g., hydrophilic polymer and hydrophilic vehicle) comprises from about 15% to about 50% of the total matrix mass, including all integers within the specified range. In one aspect, the total hydrophilic matrix comprises about 15% of the total matrix mass. In another aspect, the total hydrophilic matrix comprises about 20% of the total matrix mass. In another aspect, the total hydrophilic matrix comprises about 25% of the total matrix mass. In another aspect, the total hydrophilic matrix comprises about 30% of the total matrix mass. In another aspect, the total hydrophilic matrix comprises about 35% of the total matrix mass. In another aspect, the total hydrophilic matrix comprises about 40% of the total matrix mass. In another aspect, the total hydrophilic matrix comprises about 45% of the total matrix mass. In another aspect, the total hydrophilic matrix comprises about 50% of the total matrix mass.

In another embodiment, the total polymer weight percentage (e.g., hydrophilic polymer and organogelator) comprises from about 8% to about 50% of the total matrix mass, including all integers within the specified range. In one aspect, the total polymer comprises about 8% of the total matrix mass. In another aspect, the total polymer comprises about 10% of the total matrix mass. In another aspect, the total polymer comprises about 12% of the total matrix mass. In another aspect, the total polymer comprises about 15% of the total matrix mass. In another aspect, the total polymer comprises about 18% of the total matrix mass. In another aspect, the total polymer comprises about 20% of the total matrix mass. In another aspect, the total polymer comprises about 25% of the total matrix mass. In another aspect, the total polymer comprises about 30% of the total matrix mass. In another aspect, the total polymer comprises about 35% of the total matrix mass. In another aspect, the total polymer comprises about 40% of the total matrix mass. In another aspect, the total polymer comprises about 50% of the total matrix mass.

In one embodiment, the total lipid or lipophilic vehicle comprises about 25% to about 85% of the total matrix mass, including all integers within the specified range. In some aspects, the total lipid or lipophilic vehicle comprises about 25%, about 30%, about 35%, about 40%, about 45%, about 50%, about 51%, about 52%, about 53%, about 54%, about 55%, about 60%, about 65%, about 70%, about 75%, about 80%, or about 85% of the total matrix mass.

In another embodiment, the total lipid or lipophilic vehicle comprises about 35% to about 55% of the total matrix mass, including all integers within the specified range. In another embodiment, the total lipid or lipophilic vehicle comprises about 50% to about 65% of the total matrix mass, including all integers within the specified range. In another embodiment, the total lipid or lipophilic vehicle comprises about 60% to about 70% of the total matrix mass, including all integers within the specified range. In one aspect, the total lipid or lipophilic vehicle comprises about 35% of the total matrix mass. In one aspect, the total lipid or lipophilic vehicle comprises about 46% of the total matrix mass. In another aspect, the total lipid or lipophilic vehicle comprises about 50% of the total matrix mass. In one aspect, the total lipid or lipophilic vehicle comprises about 60% of the total matrix mass. In one aspect, the total lipid or lipophilic vehicle comprises about 65% of the total matrix mass. In another aspect, the total lipid or lipophilic vehicle comprises about 68% of the total matrix mass. In another aspect, the total lipid or lipophilic vehicle comprises about 70% of the total matrix mass.

In another embodiment, the total polymers (e.g., organogelator and hydrophilic polymer) comprise about 8% to about 50% of the total matrix mass, including all integers within the specified range. In another embodiment, the total polymers comprise about 8% to about 25% of the total matrix mass, including all integers within the specified range. In another embodiment, the total polymers comprise about 25% to about 35% of the total matrix mass, including all integers within the specified range. In another embodiment, the total polymers comprise about 35% to about 50% of the total matrix mass, including all integers within the specified range. In one aspect, the total polymers comprise about 8.5% of the total matrix mass. In another aspect, the total polymers comprise about 12% of the total matrix mass. In another aspect, the total polymers comprise about 14% of the total matrix mass. In another aspect, the total polymers comprise about 18% of the total matrix mass. In another aspect, the total controlled release polymer comprises about 22% of the total matrix mass. In another aspect, the total polymers comprise about 30% of the total matrix mass. In another aspect, the total polymers comprise about 50% of the total matrix mass.

In another embodiment, the ratio of the liquid lipid vehicle to semisolid lipid ranges from about 1.5:1 to about 40:1, including all iterations of ratios within the specified range. In one embodiment, the ratio of the lipid liquid to semisolid liquid ranges from about 1.5:1 to about 10:1, including all iterations of ratios within the specified range. In one embodiment, the ratio of the lipid liquid to semisolid liquid ranges from about 10:1 to about 20:1, including all iterations of ratios within the specified range. In one embodiment, the ratio of the lipid liquid to semisolid liquid ranges from about 20:1 to about 40:1, including all iterations of ratios within the specified range. In one aspect, the ratio of the lipid liquid to semisolid liquid is about 2:1. In one aspect, the ratio of the lipid liquid to semisolid liquid is about 5:1. In one aspect, the ratio of the lipid liquid to semisolid liquid is about 8.5:1. In one aspect, the ratio of the lipid liquid to semisolid liquid is about 15:1. In one aspect, the ratio of the lipid liquid to semisolid liquid is about 12:1. In one aspect, the ratio of the lipid liquid to semisolid liquid is about 18:1. In one aspect, the ratio of the lipid liquid to semisolid liquid is about 20:1. In one aspect, the ratio of the lipid liquid to semisolid liquid is about 35:1.

In another embodiment, the ratio of total hydrophobic matrix (e.g., liquid lipophilic vehicle and organogelator or liquid lipophilic vehicle, organogelator, and semi-solid lipophilic vehicle) to the hydrophilic matrix (e.g., hydrophilic polymer, hydrophilic vehicle) ranges from about 0.7:1 to about 10:1, including all iterations of ratios within the specified range. In one aspect, the ratio of total hydrophobic matrix to hydrophilic matrix is about 0.7:1. In one aspect, the ratio of total hydrophobic matrix to hydrophilic matrix is about 1.5:1. In one aspect, the ratio of total hydrophobic matrix to hydrophilic matrix is about 1.6:1. In one aspect, the ratio of total hydrophobic matrix to hydrophilic matrix is about 1.8:1. In one aspect, the ratio of total hydrophobic matrix to hydrophilic matrix is about 2:1. In one aspect, the ratio of total hydrophobic matrix to hydrophilic matrix is about 3.5:1. In one aspect, the ratio of total hydrophobic matrix to hydrophilic matrix is about 4.5:1. In one aspect, the ratio of total hydrophobic matrix to hydrophilic matrix is about 6.5:1. In one aspect, the ratio of total hydrophobic matrix to hydrophilic matrix is about 9:1.

In another embodiment, the ratio of total lipophilic vehicle to the total polymer ranges from about 0.5:1 to about 10:1, including all iterations of ratios within the specified range. In one aspect, the ratio of total lipophilic vehicle to total polymer is about 1.5:1. In another aspect, the ratio of total lipophilic vehicle to total polymer is about 2:1. In another aspect, the ratio of total lipophilic vehicle to total polymer is about 3:1. In another aspect, the ratio of total lipophilic vehicle to total polymer is about 4:1. In another aspect, the ratio of total lipophilic vehicle to total polymer is about 5:1. In another aspect, the ratio of total lipophilic vehicle to total polymer is about 6.5:1. In another aspect, the ratio of total lipophilic vehicle to total polymer is about 7.5:1.

In another embodiment, the ratio of organogelator to hydrophilic polymer ranges from about 0.05:1 to about 5:1, including all iterations of ratios within the specified range. In one aspect, the ratio of organogelator to hydrophilic polymer is about 0.07:1. In another embodiment, the ratio of organogelator to hydrophilic polymer ranges from about 0.2:1 to about 1:1, including all iterations of ratios within the specified range. In one aspect, the ratio of organogelator to hydrophilic polymer is about 0.5:1. In another aspect, the ratio of organogelator to hydrophilic polymer is about 0.7:1. In another aspect, the ratio of organogelator to hydrophilic polymer is about 1:1. In another aspect, the ratio of organogelator to hydrophilic polymer is about 1.3:1. In another aspect, the ratio of organogelator to hydrophilic polymer is about 1.5:1. In another aspect, the ratio of organogelator to hydrophilic polymer is about 2.0:1. In another aspect, the ratio of organogelator to hydrophilic polymer is about 5:1. In another aspect, the ratio of organogelator to hydrophilic polymer is about 0.2:1.

In one embodiment, the matrix comprises one or more liquid lipid vehicles, one or more semi-solid lipid vehicles, one or more organogelators, one or more hydrophilic polymers, one or more hydrophilic vehicles, one or more disintegrants, one or antioxidants and more active pharmaceutical ingredients. In one embodiment, the matrix comprises any one of the compositions of Tables 7-27.

In another embodiment, the one or more active pharmaceutical ingredient comprises from about 1% to about 50% of the total matrix mass, including all integers within the specified range. In another embodiment, the one or more active pharmaceutical ingredient comprises from about 1% to about 25% of the total matrix mass, including all integers within the specified range. In one aspect, the active pharmaceutical ingredient comprises about 5% of the total matrix mass. In one aspect, the active pharmaceutical ingredient comprises about 7% of the total matrix mass. In one aspect, the active pharmaceutical ingredient comprises about 10.5% of the total matrix mass. In one aspect, the active pharmaceutical ingredient comprises about 20% of the total matrix mass. In one aspect, the active pharmaceutical ingredient comprises about 25% of the total matrix mass.

In another embodiment, the ratio of active pharmaceutical ingredient to total hydrophobic matrix ranges from about 1:100 to about 1:2, including all iterations of ratios within the specified range. In another embodiment, the ratio of active pharmaceutical ingredient to total hydrophobic matrix ranges from about 1:15 to about 1:2, including all iterations of ratios within the specified range. In one aspect, the ratio of active pharmaceutical ingredient to total hydrophobic matrix is about 1:100. In another aspect, the ratio of active pharmaceutical ingredient to total hydrophobic matrix is about 1:10. In another aspect, the ratio of active pharmaceutical ingredient to total hydrophobic matrix is about 1:7.5. In another aspect, the ratio of active pharmaceutical ingredient to total hydrophobic matrix is about 1:5.5. In another aspect, the ratio of active pharmaceutical ingredient to total hydrophobic matrix is about 1:5. In another aspect, the ratio of active pharmaceutical ingredient to total hydrophobic matrix is about 1:3. In another aspect, the ratio of active pharmaceutical ingredient to total hydrophobic matrix is about 1:2.

In another embodiment, the ratio of active pharmaceutical ingredient to total hydrophilic matrix ranges from about 1:50 to about 1:5:1, including all iterations of ratios within the specified range. In another embodiment, the ratio of active pharmaceutical ingredient to total hydrophilic matrix ranges from about 1:10 to about 1.5:1, including all iterations of ratios within the specified range. In one aspect, the ratio of active pharmaceutical ingredient to total hydrophilic matrix is about 1:20. In another aspect, the ratio of active pharmaceutical ingredient to total hydrophilic matrix is about 1:10. In another aspect, the ratio of active pharmaceutical ingredient to total hydrophilic matrix is about 1:7.5. In another aspect, the ratio of active pharmaceutical ingredient to total hydrophilic matrix is about 1:6.5. In another aspect, the ratio of active pharmaceutical ingredient to total hydrophilic matrix is about 1:5.5. In another aspect, the ratio of active pharmaceutical ingredient to total hydrophilic matrix is about 1:4.5. In another aspect, the ratio of active pharmaceutical ingredient to total hydrophilic matrix is about 1:4. In another aspect, the ratio of active pharmaceutical ingredient to total hydrophilic matrix is about 1:3.5. In another aspect, the ratio of active pharmaceutical ingredient to total hydrophilic matrix is about 1:2. In another aspect, the ratio of active pharmaceutical ingredient to total hydrophilic matrix is about 1:1.5. In another aspect, the ratio of active pharmaceutical ingredient to total hydrophilic matrix is about 1.5:1.

In another embodiment, the ratio of active pharmaceutical ingredient to the total matrix ranges from about 1:100 to about 1:2, including all iterations of ratios within the specified range. In another embodiment, the ratio of active pharmaceutical ingredient to the total matrix ranges from about 1:15 to about 1:2, including all iterations of ratios within the specified range. In one aspect, the ratio of active pharmaceutical ingredient to the total matrix is about 1:100. In another aspect, the ratio of active pharmaceutical ingredient to the total matrix is about 1:10. In another aspect, the ratio of active pharmaceutical ingredient to the total matrix is about 1:7.5. In another aspect, the ratio of active pharmaceutical ingredient to the total matrix is about 1:5. In another aspect, the ratio of active pharmaceutical ingredient to the total matrix is about 1:3. In another aspect, the ratio of active pharmaceutical ingredient to the total matrix is about 1:2.

Another embodiment described herein is a method of manufacturing an abuse deterrent pharmaceutical composition described herein comprising one or more liquid lipophilic vehicles, one or more organogelators, one or more hydrophilic polymers, one or more hydrophilic vehicles, one or more anti-oxidants, one or more active pharmaceutical ingredients, optionally one or more semisolid lipid vehicles, optionally one or more disintegrants, and optionally one or more pharmaceutically acceptable excipients. The method comprises the steps of (a) heating a specified amount of one or more liquid lipophilic vehicles to about 60° C. and adding one or more organogelators (e.g., ethyl cellulose) until completely dissolved to form a first clear gel mixture; (b) hydrating one or more hydrophilic polymers (e.g., hydroxypropyl methyl cellulose) with one or more hydrophilic vehicles (e.g., polyethylene glycol); (c) mixing one or more active pharmaceutical ingredients with the mixture of step (b) to form a second uniform mixture; and (d) adding the second uniform mixture of step (c) to the first clear gel mixture of step (a) to form a final uniform matrix composition. The matrix compositions generated by the method described above may then be encapsulated in a soft capsule shell using standard rotary die encapsulation methods known in the art. Other suitable non-limiting capsule shells for the abuse deterrent matrices described herein comprise an enteric soft capsule shell, a hard capsule shell, and an enteric hard capsule shell.

In some embodiments, further annealing processing steps may be needed for matrix compositions comprising one or more semi-solid vehicles (e.g., a wax). As described herein, annealing may be carried out by heating a pharmaceutical composition comprising a soft capsule shell encapsulating a matrix fill described herein following encapsulation to form an annealed dosage form. In some aspects, the pharmaceutical compositions may be annealed at a temperature from about 50° C. to about 90° C. for about 0.25 hours to about 5 hours, including all integers within the specified ranges of temperature and time. In one aspect, pharmaceutical compositions comprising a soft capsule shell encapsulating a matrix fill as described herein may be annealed at a temperature of about 70° C. for about 1 hour.

In one embodiment, the matrix contains an active pharmaceutical ingredient in a suspended, form, soluble form, insoluble form, or combinations thereof. In another embodiment, the matrix contains an active pharmaceutical ingredient useful for the treatment of pain. In one embodiment, the active pharmaceutical ingredient includes tapentadol, oxycodone, morphine, morphine analogues, or morphine antagonists, codeine, morphine, methadone, fentanyl and analogs, opioid pain relievers: oxycodone hydrochloride, hydrocodone bitartrate hydromorphone, oxymorphone, meperidine, propoxyphene, flunitrazepam, barbiturates, amytal, nembutal, seconal, phenobarbital; benzodiazepines, zolpidem, zaleplon, eszopiclone, amphetamines, or methylphenidate.

In one embodiment, the matrix comprises one or more active pharmaceutical ingredients (API). In one aspect, the active pharmaceutical ingredient is useful in treating pain. In one aspect, the active pharmaceutical ingredient is tapentadol, oxycodone, hydrocodone, or codeine. In one aspect, the active pharmaceutical ingredient is oxycodone or hydrocodone.

Examples of specific active drug substances suitable for use in the pharmaceutical compositions provided herein include: anti-inflammatory and antirheumatic active drug substances, such as, for example: butylpyrazolidine, phenylbutazone, mofebutazone, oxyphenbutazone, clofezone, kebuzone, acetic acid derivatives and related substances, indometacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, oxicam, piroxicam, tenoxicam, droxicam, lornoxicam, meloxicam, methotrexate, propionic acid derivatives, ibuprofen, naproxen, ketoprofen, fenoprofen, fenbufen, benoxaprofen, suprofen, pirprofen, flurbiprofen, indoprofen, tiaprofenic acid, oxaprozin, ibuproxam, dexibuprofen, flunoxaprofen, alminoprofen, dexketoprofen, fenamates, mefenamic acid, tolfenamic acid, flufenamic acid, meclofenamic acid, coxibs, celecoxib, rofecoxib, valdecoxib, parecoxib, etoricoxib, lumiracoxib, nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate, feprazone, dipyrocetyl, acetylsalicylic acid, quinolines, oxycinchophen, gold preparations, sodium aurothiomalate, sodium aurotiosulfate, auranofin, aurothioglucose, aurotioprol, penicillamine or bucillamine.

In another embodiment, suitable active pharmaceutical ingredients can comprise analgesics, such as, for example: opioids, natural opium alkaloids, morphine, opium, hydromorphone, nicomorphine, oxycodone, dihydrocodone, diamorphine, tapentadol, papaveretum, papaveretum, codeine, phenylpiperidine derivatives, ketobemidone, pethidine, fentanyl, diphenylpropylamine derivatives, dextromoramide, piritramide, dextropropoxyphene, bezitramide, methadone, benzomorphan derivatives, pentazocine, phenazocine, oripavine derivatives, buprenorphine, morphinan derivatives, butorphanol, nalbuphine, tilidine, tramadol, dezocine, salicylic acid and derivatives, acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, pyrazolones, phenazone, metamizole sodium, aminophenazone, propyphenazone, nifenazone, anilides, paracetamol, phenacetin, bucetin, propacetamol, other analgesics and antipyretics, such as, for example: rimazolium, glafenine, floctafenine, viminol, nefopam, flupirtine, or ziconotide.

In another embodiment, suitable active pharmaceutical ingredients can comprise anaesthetics, such as, for example: ethers, diethyl ether, vinyl ether, halogenated hydrocarbons, halothane, chloroform, methoxyflurane, enflurane, trichloroethylene, isoflurane, desflurane, sevoflurane, barbiturates, methohexital, hexobarbital, thiopental, narcobarbital, opioid anaesthetics, fentanyl, alfentanil, sufentanil, phenoperidine, anileridine, remifentanil, other general anaesthetics, such as, for example: droperidol, ketamine, propanidid, alfaxalone, etomidate, propofol, hydroxybutyric acid, nitrous oxide, esketamine, xenon, esters of aminobenzoic acid, metabutethamine, procaine, tetracaine, chloroprocaine, benzocaine, amides, bupivacaine, lidocaine, mepivacaine, prilocaine, butanilicaine, cinchocaine, etidocaine, articaine, ropivacaine, levobupivacaine, esters of benzoic acid, cocaine, other local anaesthetics, such as, for example: ethyl chloride, dyclonine, phenol, or capsaicin.

In another embodiment, suitable active pharmaceutical ingredients can comprise antimigraine active drug substances, such as, for example: ergot alkaloids, dihydroergotamine, ergotamine, methysergide, lisuride, corticosteroid derivatives, flumedroxone, selective serotonin ($5HT^1$) agonists, sumatriptan, naratriptan, zolmitriptan, rizatriptan, almotriptan, eletriptan, frovatriptan, other antimigraine preparations, pizotifen, clonidine, iprazochrome, dimetotiazine, or oxetorone.

In another embodiment, suitable active pharmaceutical ingredients can comprise antiepileptic active drug substances, such as, for example: barbiturates and derivatives, methylphenobarbital, phenobarbital, primidone, barbexaclone, metharbital, hydantoin derivatives, ethotoin, phenytoin, amino(diphenylhydantoin) valeric acid, mephenytoin, fosphenytoin, oxazolidine derivatives, paramethadione, trimethadione, ethadione, succinimide derivatives, ethosuximide, phensuximide, mesuximide, benzodiazepine derivatives, clonazepam, carboxamide derivatives, carbamazepine, oxcarbazepine, rufinamide, fatty acid derivatives, valproic acid, valpromide, aminobutyric acid, vigabatrin, progabide, tiagabine, other antiepileptics, such as, for example: sultiame, phenacemide, lamotrigine, felbamate, topiramate, gabapentin, pheneturide, levetiracetam, zonisamide, pregabalin, stiripentol, lacosamide, or beclamide.

In another embodiment, suitable active pharmaceutical ingredients can comprise anticholinergic active drug substances, such as, for example: tertiary amines, trihexyphenidyl, biperiden, metixene, procyclidine, profenamine, dexetimide, phenglutarimide, mazaticol, bornaprine, tropatepine, ethers chemically close to antihistamines, etanautine, orphenadrine (chloride), ethers of tropine or tropine derivatives, benzatropine, or etybenzatropine.

In another embodiment, suitable active pharmaceutical ingredients can comprise dopaminergic active drug substances, such as, for example: dopa and dopa derivatives, levodopa, melevodopa, etilevodopa, adamantane derivatives, amantadine, dopamine agonists, bromocriptine, pergolide, dihydroergocryptine mesylate, ropinirole, pramipexole, cabergoline, apomorphine, piribedil, rotigotine, monoamine, oxidase B inhibitors, selegiline, rasagiline, other dopaminergic agents, such as, for example: tolcapone, entacapone, or budipine.

In another embodiment, suitable active pharmaceutical ingredients can comprise antipsychotic active drug substances, such as, for example: phenothiazines with aliphatic side-chain, chlorpromazine, levomepromazine, promazine, acepromazine, triflupromazine, cyamemazine, chlorproethazine, phenothiazines with piperazine structure, dixyrazine, fluphenazine, perphenazine, prochlorperazine, thiopropazate, trifluoperazine, acetophenazine, thioproperazine, butaperazine, perazine, phenothiazines with piperidine structure, periciazine, thioridazine, mesoridazine, pipotiazine, butyrophenone derivatives, haloperidol, trifluperidol, melperone, moperone, pipamperone, bromperidol, benperidol, droperidol, fluanisone, indole derivatives, oxypertine, molindone, sertindole, ziprasidone, thioxanthene derivatives, flupentixol, clopenthixol, chlorprothixene, tiotixene, zuclopenthixol, diphenylbutylpiperidine derivatives, fluspirilene, pimozide, penfluridol, diazepines, oxazepines, thiazepines, loxapine, clozapine, olanzapine, quetiapine, neuroleptics, tetrabenazine, benzamides, sulpiride, sultopride, tiapride, remoxipride, amisulpride, veralipride, levosulpiride, lithium, other antipsychotics, such as, for example prothipendyl, risperidone, clotiapine, mosapramine, zotepine, aripiprazole, or paliperidone.

In another embodiment, suitable active pharmaceutical ingredients can comprise anxiolytic active drug substances, such as, for example: benzodiazepine derivatives, diazepam, chlordiazepoxide, medazepam, oxazepam, potassium clorazepate, lorazepam, adinazolam, bromazepam, clobazam, ketazolam, prazepam, alprazolam, halazepam, pinazepam, camazepam, nordazepam, fludiazepam, ethyl loflazepate, etizolam, clotiazepam, cloxazolam, tofisopam, diphenylmethane derivatives, hydroxyzine, captodiame, carbamates, meprobamate, emylcamate, mebutamate, dibenzo-bicyclooctadiene derivatives, benzoctamine, azaspirodecanedione derivatives, buspirone, other anxiolytics, such as, for example: mephenoxalone, gedocarnil, or etifoxine.

In another embodiment, suitable active pharmaceutical ingredients can comprise hypnotic and sedative active drug substances, such as, for example: barbiturates, pentobarbital, amobarbital, butobarbital, barbital, aprobarbital, secobarbital, talbutal, vinylbital, vinbarbital, cyclobarbital, heptabarbital, reposal, methohexital, hexobarbital, thiopental, ethallobarbital, allobarbital, proxibarbal, aldehydes and derivatives, chloral hydrate, chloralodol, acetylglycinamide chloral hydrate, dichloralphenazone, paraldehyde, benzodiazepine emepronium derivatives, flurazepam, nitrazepam, flunitrazepam, estazolam, triazolam, lormetazepam, temazepam, midazolam, brotizolam, quazepam, loprazolam, doxefazepam, cinolazepam, piperidinedione derivatives, glutethimide, methyprylon, pyrithyldione, benzodiazepine related drugs, zopiclone, zolpidem, zaleplon, ramelteon, other hypnotics and sedatives, such as, for example: methaqualone, clomethiazole, bromisoval, carbromal, scopolamine, propiomazine, triclofos, ethchlorvynol, valerian, hexapropymate, bromides, apronal, valnoctamide, methylpentynol, niaprazine, melatonin, dexmedetomidine, or dipiperonylaminoethanol.

In another embodiment, suitable active pharmaceutical ingredients can comprise antidepressant active drug substances, such as, for example: non-selective monoamine reuptake inhibitors, desipramine, imipramine, imipramine oxide, clomipramine, opipramol, trimipramine, lofepramine, dibenzepin, amitriptyline, nortriptyline, protriptyline, doxepin, iprindole, melitracen, butriptyline, dosulepin, amoxapine, dimetacrine, amineptine, maprotiline, quinupramine, selective serotonin reuptake inhibitors, zimeldine, fluoxetine, citalopram, paroxetine, sertraline, alaproclate, fluvoxamine, etoperidone, escitalopram, monoamine oxidase inhibitors, isocarboxazid, nialamide, phenelzine, tranylcypromine, iproniazide, iproclozide, monoamine oxidase A inhibitors, moclobemide, toloxatone, other antidepressants, such as, for example: oxitriptan, tryptophan, mianserin, nomifensine, trazodone, nefazodone, minaprine, bifemelane, viloxazine, oxaflozane, mirtazapine, medifoxamine, tianeptine, pivagabine, venlafaxine, milnacipran, reboxetine, gepirone, duloxetine, agomelatine, desvenlafaxine, centrally acting sympathomimetics, such as, for example: amfetamine, dexamfetamine, lisdexamfetamine, metamfetamine, methylphenidate, dexmethylphenidate, pemoline, fencamfamin, modafinil, fenozolone, atomoxetine, fenetylline, xanthine derivatives, caffeine, propentofylline, other psychostimulants and nootropics, such as, for example meclofenoxate, pyritinol, piracetam, deanol, fipexide, citicoline, oxiracetam, pirisudanol, linopirdine, nizofenone, aniracetam, acetylcarnitine, idebenone, prolintane, pipradrol, pramiracetam, adrafinil, or vinpocetine.

In another embodiment, suitable active pharmaceutical ingredients can comprise anti-dementia active drug substances, such as, for example: anticholinesterases, tacrine, donepezil, rivastigmine, galantamine, other anti-dementia drugs, memantine, or *Ginkgo biloba*.

In another embodiment, suitable active pharmaceutical ingredients can comprise other nervous system active drug substances, such as, for example: parasympathomimetics, anticholinesterases, neostigmine, pyridostigmine, distigmine, ambenonium, choline esters, carbachol, bethanechol, and other parasympathomimetics, such as, for example, pilocarpine, or choline alfoscerate.

Active drug substances used in addictive disorders, such as, for example: nicotine, bupropion, varenicline, disulfiram, calcium carbimide, acamprosate, naltrexone, buprenorphine, methadone, levacetylmethadol, lofexidine, betahistine, cinnarizine, flunarizine, acetylleucine, gangliosides and ganglioside derivatives, tirilazad, riluzole, xaliproden, hydroxybutyric acid, or amifampridine.

In another embodiment, suitable active pharmaceutical ingredients can comprise opium alkaloids and derivatives, such as, for example: ethylmorphine, hydrocodone, codeine, opium alkaloids with morphine, normethadone, noscapine, pholcodine, dextromethorphan, thebacon, dimemorfan, acetyldihydrocodone, benzonatate, benproperine, clobutinol, isoaminile, pentoxyverine, oxolamine, oxeladin, clofedanol, pipazetate, bibenzonium bromide, butamirate, fedrilate, zipeprol, dibunate, droxypropine, prenoxdiazine, dropropizine, cloperastine, meprotixol, piperidione, tipepidine, morclofone, nepinalone, levodropropizine, or dimethoxanate.

In another embodiment, the active pharmaceutical ingredient may be a substance with abuse potential that presents a safety risk. Such active drug substance may include: 1-(1-phenylcyclohexyl)pyrrolidine, 1-(2-phenylethyl)-4-phenyl-4-acetoxypiperidine, 1-[1-(2-thienyl)-cyclohexylpiperidine, 1-[1-(2-thienyl)cyclohexyl]pyrrolidine, 1-methyl-4-phenyl-4-propionoxy-piperidine, 1-phenylcyclohexylamine, 1-piperidinocyclohexanecarbonitrile, 2,5-dimethoxy-4-ethylamphetamine, 2,5-dimethoxyamphetamine, 2C-B-(4-bromo-2,5-dimethoxypenethylamine), 2C-D (2,5-dimethoxy-4-methylphenethylamine), 2C-I (4-iodo-2,5-dimethoxy-phenethylamine), 2C-T-2 (2,5-dimethoxy-4-ethylthiophenethylamine), 2C-T-4 (2,5-dimethoxy-4-isopropyl thiophenethylamine), 2C-T-7 (2,5-dimethoxy-4-(n)-propylthiophenethylamine), 3,4-methylenedioxymethamphetamine, 3,4,5-trimethoxyamphetamine, 3,4-methylenedioxyamphetamine, 3,4-methylenedioxy-N-ethylamphetamine, 3-methylfentanyl, 3-methylthiofentanyl, 4-brorno-2,5-dimethoxyamphetamine, 4-bromo-2,5-dimethoxyphenethylamine, 4-methoxyamphetamine, 4-methyl-2,5-dimethoxyamphetamine, 4-methylaminorex (cis isomer), 5-MeO-DIPT (5-methoxy-N,N-diisopropyltryptamine), 5-MeO-DMT (5-methoxy-N,N-dimethyltryptamine), 5-methoxy-3,4-methylenedioxyamphetamine, acetorphine, acetorphine, acetyl-alpha-methylfentanyl, acetyl-alpha-methylfentanyl, acetyldihydrocodone, acetylmethadol, acetylmethadol, alfentanil, allobarbital, allylprodine, alphacetylmethadol except levo-alphacetylmethadol, alpha-ethyltryptamine, alphameprodine, alphamethadol, alphamethadol, alpha-methylfentanyl, alpha-methylthiofentanyl, alphaprodine, alprazolam, amfepramon, amfetaminil, amineptin, aminorex, amobarbital, amphetamine, dextroamphetamine, amilnitrite (all isomers of the amyl group), anabolic steroids, anileridine, aprobarbital, barbital, barbituric acid derivative, BDB (3,4-methylenedioxyphenyl)-2-butanamine), benzethidin, benzethidine, benzoylecgonine, benzphetamine, benzphetamine, benzylmethylcetone, benzylmorphine, betacetylmethadol, beta-hydroxy-3-methylfentanyl, beta-hydroxyfentanyl, betameprodine, betameprodine, betamethadol, betaprodine, bezitramide, bezitramide, boldenone, brolamfetamine, bromazepam, brotizolam, bufotenine, buprenorphine, butabarbital, butalbital, butobarbital, butorphanol, BZP (A2)(1-benzylpiperazin), camazepam, cannabis, carfentanil, catha edulis, cathine, cathinone, chloral betaine, chloral hydrate, chlordiazepoxide, chlorhexadol, chlorotestosterone (same as clostebol), chlorphentermine, clobazam, clonazepam, clonitazene, clonitazene, clorazepate, clortermine, clostebol, clotiazepam, cloxazolam, coca leaves, cocaine, codeine, codeine and isoquinoline alkaloid, codeine methylbromide, codeine-N-oxide, codoxime, cyclobarbital (hexemal NFN), cyprenorphine, dehydrochlormethyltestosterone, delorazepam, desomorphine, dexamfetamine, dexfenfluramine, dexmethylphenidate, dextromoramide, dextropropoxyphene, diacetylmorphine, diampromide, diazepam, dichloralphenazone, diethylpropion, diethylthiambutene, diethyltryptamine, difenoxin, dihydrocodone, dihydroetorphine, dihydromorphine, dihydrotestosterone, dimenoxadol, dimepheptanol, dimethylthiambutene, dimethyltryptamine, dioxaphetyl butyrate, diphenoxylate, dipipanone, diprenorphine, dronabinol, drostanolone, drotebanol, ecgonine, estazolam, ethchlorvynol, ethinamate, ethyl loflazepate, ethylestrenol, ethylmethylthiambutene, ethylmorphine, ethylmorphine, eticyclidine, etilamfetamine, etonitazene, etorphine, etoxeridine, etryptamine, fencamfamin, fenethylline, fenetylline, fenfluramine, fenproporex, fentanyl, fludiazepam, flunitrazepam, fluoxymesterone, flurazepam, formebolone, fungi and spores of the species psilocybe semilanceata, furethidine, gamma hydroxybutyric acid, glutethimide, halazepam, haloxazolam, heroine, hydrocodone, hydrocodone & isoquinoline alkaloid, hydromorphinol, hydromorphone, hydroxypethidine, ibogaine, isobutyl nitrite, isomethadone, ketamine, ketazolam, ketobemidone, levamfetamine, levo-alphacetylmethadol, levo-methamphetamine, levomethorphan, levomoramide, levophenacylmorphan, levorphanol, lisdexamfetamine, loprazolam, lorazepam, lormetazepam, lysergic acid, lysergic acid amide, lysergic acid diethylamide, marijuana, mazindol, MBDN (N-methyl-1-(3,4-methylenedioxyphenyl)-2-butanamine), mCPP (1-(3-chlorphenyl)piperazine), mebutamate, mecloqualone, medazepam, mefenorex, MeOPP (1-(4-methoxyphenyl)piperazine), meperidine, meperidine intermediate, meprobamate, mescaline, mesocarb, mesterolone, metamfetamine, metazocine, methadone, methadone intermediate, methamphetamine, methandienone, methandrolone, methandriol, methandrostenolone, methaqualone, methcathinone, methenolone, methohexital, methyldesorphine, methyldihydromorphine, methylphenidate, methylphenobarbital (mephobarbital), methyltestosterone, methyprylone, metopone, mibolerone, midazolam, modafinil, moramide-intermediate, morpheridine, morphine, morphine methylbromide, morphine methylsulfonate, morphine-N-oxide, myrophine, N,N-dimethylamphetamine, nabilone, nalorphine, nandrolone, N-ethyl-1-phenylcyclohexylamine, N-ethyl-3-piperidyl benzilate, N-ethylamphetamine, N-hydroxy-3,4-methylenedioxyamphetamine, nicocodeine, nicocodine, nicodicodine, nicomorphine, nimetazepam, nitrazepam, N-methyl-3-piperidyl benzilate, noracymethadol, norcodeine, nordiazepam, norethandrolone, norlevorphanol, normethadone, normorphine, norpipanone, norpipanone, opium, oxandrolone, oxazepam, oxazolam, oxycodone, oxymesterone, oxymetholone, oxymorphone, para-fluorofentanyl, parahexyl, paraldehyde, pemoline, pentazocine, pentobarbital, petrichloral, peyote, phenadoxone, phenampromide, phenazocine, phencyclidine, phendimetrazine, phenmetrazine, phenobarbital, phenomorphan, phenoperidine, phentermine, phenylacetone, pholcodine, piminodine, pinazepam, pipradrole, piritramide, PMMA (paramethyxymethyl amphetamine), prazepam, proheptazine, properidine, propiram, psilocybine, psilocine, pyrovalerone, quazepam, racemethorphane, racemoramide, racemorphane, remifentanil, salvia divinorum, salvinorin A, secobarbital, secobarbital, sibutramine, SPA, stanolone, stanozolol, sufentanil, sulfondiethylmethane, sulfonethylmethane, sulfonmethane, talbutal, temazepam, tenamfetamine, testolactone, testosterone, tetrahydrocannabinols, tetrazepam, TFMPP (1-(3-triflourmethylphenyl)piperazine), thebacon, thebaine, thiamylal, thiofentanyl, thiopental, tiletamine and zolazepam in combination, tilidine, trenbolone, triazolam, trimeperidine, vinbarbital, zaleplon, zipeprol, zolpidem, or zopiclone.

Other suitable examples of active drug substances suitable for use in the pharmaceutical compositions described herein include, for example, alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodone, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, morphine 6-glucuronide, morphine 3-glucuronide, myrophine, nalbuphine, narcine, nicomorphine, norlevorphanol, normethadone, nalorphine, normorphine, norpipanone, opium, oxycodone, oxycodeine, oxymorphone, papaveretum, pentazocine, phenadoxone, phenomorphan, phenazocine, phenoperidine, piminodine, piritramide, propheptazine, promedol, properidine, propiram, propoxyphene, sufentanil, tilidine, tramadol, thebaine, levo-alphacetylmethadol (LAAM), remifentanil, carfentanyl, ohmefentanyl, MPPP, prodine, PEPAP, levomethorphan, etorphine, lefetamine, loperamide, diphenoxylate, or pethidine.

Other examples of active drug substances suitable for use in the pharmaceutical compositions described herein include anabolic steroids, cannabis, cocaine, or diazepam.

In another embodiment, the active drug substance comprises the therapeutic classes including non-steroidal anti-inflammatory substances or antirheumatic active drug substances.

In other embodiments, the active drug substance comprises analgesics, opioids, antipyretics, anaesthetics, antimigraine agents, antiepileptics, anti-parkinson agents, dopaminergic agents, antipsychotics, anxiolytics, sedatives, antidepressants, psychostimulants agents, dopamine, noradrenaline, nicotinic, alfa-adrenergic, serotonin, H3 antagonists used for ADHD or nootropics agents used in addictive disorders.

In other embodiments, the active drug substance comprises therapeutic classes including anaesthetics, centrally acting analgesics, sedative-hypnotics, anxiolytics, appetite suppressants, decongestants, antitussives, antihistamines, antiemetics, antidiarrheals, and drugs used to treat narcolepsy, or attention deficit hyperactivity disorder.

In another embodiment, the active drug substance is associated with abuse syndromes and the active drug substance may, for example, be selected from opioids, CNS depressants, CNS stimulants, cannabinoids, nicotine-like compounds, glutamate antagonists, or N-methyl-D-aspartate (NMDA) antagonists.

In another embodiment, the active drug substance is an analgesic. Examples of analgesics suitable for use in the pharmaceutical compositions described herein include, for example, opioids, natural opium alkaloids, morphine, opium, hydromorphone, nicomorphine, oxycodone, dihydrocodeine, diamorphine, tapentadol, papaveretum, codeine, phenylpiperidine derivatives, ketobemidone, pethidine, fentanyl, diphenylpropylamine derivatives, dextromoramide, piritramide, dextropropoxyphene, bezitramide, methadone, benzomorphan derivatives, pentazocine, phenazocine, oripavine derivatives, buprenorphine, morphinan derivatives, butorphanol, nalbuphine, tilidine, tramadol, dezocine, salicylic acid and derivatives, acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, pyrazolones, phenazone, metamizole sodium, aminophenazone, propyphenazone, nifenazone, anilides, paracetamol, phenacetin, bucetin, propacetamol, other analgesics and antipyretics such as, for example, rimazolium, glafenine, floctafenine, viminol, nefopam, flupirtine, or ziconotide.

In another embodiment, the active drug substance is an opioid. Where an opioid is included as an active drug substance, the opioid may comprise naturally occurring opioids, synthetic opioids, or semisynthetic opioids.

In other embodiment, the active drug substance comprises amfetamine, dexamfetamine, lisdexamfetamine, metamfetamine, methylphenidate, dexmethylphenidate, or combinations thereof.

In another embodiment, the pharmaceutical compositions disclosed herein includes an opioid, the opioid is selected from buprenorphine, codeine, dextromoramide, dihydrocodone, fentanyl, hydrocodone, hydromorphone, morphine, pentazocine, oxycodeine, oxycodone, oxymorphone, norhydrocodone, noroxycodone, morphine-6-glucuronode, tramadol, tapentadol, or dihydromorphine.

Where an opioid is used as an active drug substance, the opioid may be present in any of its crystalline, polymorphous, semi-crystalline, and amorphous or polyamorphous forms. Furthermore, in another embodiment, an opioid used as an active drug substance may be present in one or more forms selected from its crystalline, polymorphous, semi-crystalline, or amorphous or polyamorphous forms.

Some embodiments of the pharmaceutical compositions disclosed herein include an opioid as an active drug substance, the active drug substance is selected from morphine, oxycodone, hydrocodone, hydromorphone, norhydrocodone, oxymorphone, noroxycodone, morphine-6-glucuronode and pharmaceutically acceptable salts thereof, including oxycodone hydrochloride, hydrocodone bitartrate, hydromorphone hydrochloride or morphine sulphate pentahydrate.

In other embodiments, the pharmaceutical compositions as described herein are suitable for use for water soluble as well as slightly soluble or insoluble active drug substances.

In another embodiment, all of the above mentioned active drug substances may also be in the form of pharmaceutically acceptable salts, uncharged or charged molecules, molecular complexes, solvates, or anhydrates thereof, and, if relevant, single isomers, enantiomers, racemic mixtures, or mixtures thereof.

In another embodiment, the pharmaceutical compositions described herein may comprise pharmaceutically acceptable salts of any of the above mentioned active drug substances.

In another embodiment, the active pharmaceutical ingredient is hydrocodone or oxycodone or a pharmaceutically acceptable salt form of either hydrocodone or oxycodone. Pharmaceutically acceptable salts forms are those formed by contacting hydrocodone or oxycodone free base with a suitable acid in a suitable solvent under suitable conditions that will form a form of hydrocodone or oxycodone acid addition salt. Suitable acids include hydrochloric acid, camphorsulfonic acid, hydrobromic acid, sulfuric acid, methanesulfonic acid, formic acid, acetic acid, oxalic acid, succinic acid, tartaric acid, mandelic acid, malic acid, salicylic acid, fumaric acid, lactic acid, citric acid, glutamic acid, and/or aspartic acid.

The term "pharmaceutically acceptable salts" of an active drug substance includes alkali metal salts such as, for example, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid etc. In another embodiment, pharmaceutically acceptable opioid salts can comprise sulphate salts, hydrochloride salts, and bitartrate salts.

In another embodiment, the active pharmaceutical ingredient may be in any of its crystalline, polymorphous, semi-crystalline, amorphous or polyamorphous forms or mixtures thereof.

The concentration of the active drug substance in the pharmaceutical composition for use according to the disclosure depends on the specific active drug substance, the disease to be treated, the condition of the patient, the age, and gender of the patient, etc. The above-mentioned active drug substances may be known active drug substances and a person skilled in the art will be able to find information as to the dosage of each active drug substance and, accordingly, will know how to determine the amount of each active drug substance in the pharmaceutical composition.

The active pharmaceutical ingredient may be a new chemical entity for which the amount of information is limited. In such cases, the dosage has to be evaluated based on available preclinical and/or clinical data.

In one embodiment described herein, the pharmaceutical composition comprises soft capsule shell comprising a matrix comprising an active pharmaceutical ingredient.

In one embodiment described herein, the soft capsule shell has the composition of Table 2, including all possible iterations of the specified ranges that provide 100% for the total weight percentage, including or excluding the optional colorings, flavorings, or excipients.

TABLE 2

Exemplary soft gelatin capsule composition

| Component | Exemplary Component | Weight Percentage (%) |
|---|---|---|
| Film-forming polymer | Gelatin | 20-36 (Gelatin) |
| Plasticizer | Glycerol | 10-30 |
| Solvent | Water | 20-70 |
| Opacifier (optional) | Titanium dioxide | 0.5-1.5 |
| Coloring agent (optional) | Various | 0.05-0.1 |
| TOTAL | | 100% |

Film-former polymers that are useful for creating soft capsules are gelatin, hydroxypropylmethylcellulose (HPMC) or carrageenan (e.g., iota carrageenan and kappa carrageenan). In one aspect of the enteric soft capsule shell described herein, the film-forming polymer is gelatin. In another aspect of the enteric soft capsule shell described herein, the film-forming polymer is carrageenan.

Plasticizers that are useful for creating soft capsules as described herein are glycerol, sorbitol, polyethylene glycols, or combinations thereof. The weight ratio between the film-forming polymer, plasticizer, and solvent is adjusted so that the gel mass is flowable and not too viscous, and can be made into soft capsules using rotary die encapsulation methods.

In one embodiment, the enteric soft capsule shell has the exemplary composition shown in Table 3.

TABLE 3

Exemplary Soft Capsule Shell Composition

| Component | Percent weight (%) |
|---|---|
| Gelatin | 43 |
| Glycerol | 20 |
| Titanium dioxide (optional) | 0.7 |
| Coloring agent (optional) | 0.1 |
| Water | 36.2 |
| TOTAL | 100% |
| Final pH | ~4-7 |
| Ratio total plasticizer to gelatin | 20:43 (0.46:1) |
| Water content in dried soft capsule shell: | 8-15% |

In one embodiment described herein, the soft capsule comprises about 43% of at least one film-forming polymer; about 20% of at least one plasticizer; about 36% water; optionally, about 0.7% titanium dioxide; and optionally, about 0.1% of at least one coloring agent.

In one embodiment described herein, the enteric soft capsule described herein comprises a composition of about 3% to about 10% film forming polymer (e.g., a composition of carrageenan); about 10% to about 30% filler; about 10% to about 30% plasticizer; and about 30% to about 70% solvent.

In one embodiment, the weight percentage range of film-forming polymer of the soft capsule described herein is about 35% to about 45%, including all integers within the specified range. In one aspect, the film-forming polymer weight percentage is about 38%. In another aspect, the film-forming 1 polymer weight percentage is about 42%. In another aspect, the film-forming polymer weight percentage is about 44%.

In one embodiment, the weight percentage range of film-forming polymer of the soft capsule described herein is about 3% to about 15%, including all integers within the specified range. In one aspect, the film-forming polymer weight percentage is about 3%. In one aspect, the film-forming polymer weight percentage is about 5%. In one aspect, the film-forming polymer weight percentage is about 7%. In one aspect, the film-forming polymer weight percentage is about 10%. In one aspect, the film-forming polymer weight percentage is about 12%.

In one embodiment, the weight percentage range of plasticizer is about 15% to about 22%, including all iterations of integers with the specified range. In one aspect, the plasticizer weight percentage is about 17%. In another aspect, the plasticizer weight percentage is about 18.5%. In another aspect, the plasticizer weight percentage is about 20%.

In one embodiment, the weight percentage ratio range of plasticizer to film-forming polymer is about 0.33:1 to about 0.56:1, including all iterations of iterations of ratios with the specified range. In one embodiment, the weight percentage ratio range of plasticizer to film-forming polymer is about 0.38:1. In one embodiment, the weight percentage ratio range of plasticizer to film-forming polymer is about 0.42:1. In one embodiment, the weight percentage ratio range of plasticizer to film-forming polymer is about 0.46:1. In one embodiment, the weight percentage ratio range of plasticizer to film-forming polymer is about 0.52:1.

In one aspect, soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing soft capsules comprising the pharmaceutical composition as described herein. The process includes preparing a gel mass composition comprising a film-forming, water-soluble polymer, an appropriate plasticizer, and solvent; casting the gel mass into films or ribbons using heat-controlled drums or surfaces; and manufacturing a soft capsule comprising a matrix fill using rotary die technology. The thickness of the films or ribbons that form the soft capsule shell is from about 0.010 inches (≈0.254 mm) to about 0.050 inches (≈1.27 mm), including all integers within the specified range. The shell thickness can be about 0.010 inch (≈0.254 mm), about 0.015 inch (≈0.381 mm), about 0.02 in (≈0.508 mm), about 0.03 in (≈0.762 mm), about 0.04 in (≈1.02 mm), or about 0.05 in (≈1.27 mm). In one embodiment, the thickness is about 0.02 inches (≈0.508 mm) to about 0.040 inches (≈1.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm).

In one embodiment described herein, the soft capsule shell described herein, encapsulates a matrix fill as described herein. In another embodiment described herein, the soft capsule shell and encapsulated matrix fill comprises a outer dimension from about 2 oval to about 30 oval including all iterations of capsule size within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the soft capsule shell and encapsulated matrix fill comprises a outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the soft capsule shell and encapsulated matrix fill comprises a outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11 oblong, 12 oblong, 14 oblong, 16 oblong, 20 oblong, or 22 oblong). Dimension specifications of soft capsules and tablets are known to those skilled in the art. See *Remington's Essentials of Pharmaceutics*, Pharmaceutical Press Publishing Company, London, UK, 1$^{st}$ Edition, 2013, which is incorporated by reference herein for such teachings.

In another embodiment described herein, the pharmaceutical composition comprises an enteric soft capsule shell comprising a matrix fill comprising an active pharmaceutical ingredient.

Enteric soft capsules are described in International Patent Application Publication No. WO 2004/030658; U.S. Patent Application Publication No. US 2006/0165778; and U.S. Pat. No. 8,685,445, each of which is incorporated by reference herein for such teachings. The enteric soft capsule shell may comprise one or more film forming polymers, one or more enteric acid-insoluble polymers, one or more plasticizers, one or more alkali-neutralizing agents, one or more solvents, optionally one or more colorants, and optionally one or more flavorings or other conventionally accepted pharmaceutical excipients or additives.

Film-former polymers that are useful for creating enteric soft capsules are gelatin, hydroxypropylmethylcellulose (HPMC) or carrageenan (e.g., iota carrageenan and kappa carrageenan). In one aspect of the enteric soft capsule shell described herein, the film-forming polymer is gelatin. In another aspect of the enteric soft capsule shell described herein, the film-forming polymer is carrageenan.

Examples of enteric, acid-insoluble polymers are acrylic and methacrylate acid copolymers, cellulose acetate phthalate (CAP), cellulose acetate butyrate, hydroxypropylmethylcellulose phthalate (HPMCP), algenic acid salts such as sodium or potassium alginate, or shellac. Poly(methacylic acid-co-methyl methacrylate) anionic copolymers based on methacrylic acid and methyl methacrylate are particularly stable and are preferred in some embodiments. Poly(meth)acrylates (methacrylic acid copolymer), available under the trade name EUDRAGIT® (Evonik Industries AG, Essen, Germany), are provided as powder or aqueous dispersions. In one aspect, the methacrylic acid copolymer can be EUDRAGIT® L 30 D-55; EUDRAGIT® L 100-55; EUDRAGIT® L 100; EUDRAGIT® L 12.5; EUDRAGIT® S 100; EUDRAGIT® S 12.5; EUDRAGIT® FS 30 D; EUDRAGIT® E 100; EUDRAGIT® E 12.5; EUDRAGIT® E PO; EUDRAGIT® RL 100; EUDRAGIT® RL PO; EUDRAGIT® RL 30 D; EUDRAGIT® RL 12.5; EUDRAGIT® RS 100; EUDRAGIT® RS PO; EUDRAGIT® RS 30 D; EUDRAGIT® RS 12.5; EUDRAGIT® NE 30 D; EUDRAGIT® NE 40 D; EUDRAGIT® NM 30 D; or other poly(meth)acrylate polymers. In one aspect, the enteric polymer is EUDRAGIT® L 100, a methacrylic acid copolymer, Type A. Acid-insoluble polymer specifications are detailed in the United States Pharmacopoeia and in various monographs.

Plasticizers that are useful for creating enteric soft capsules as described herein are glycerol, sorbitol, polyethylene glycol, citric acid, citric acid esters, such as tri-ethyl citrate, or combinations thereof. The weight ratio between the film-forming polymer, the enteric acid-insoluble polymer, and plasticizer is adjusted so that the gel mass is flowable and not too viscous, and can be made into soft capsules using rotary die encapsulation methods.

In one embodiment, enteric soft capsule shell compositions can be made by dissolving the enteric acid-insoluble polymer in an aqueous solution of an alkali neutralizing agent such as ammonia, sodium hydroxide, potassium hydroxide, or liquid amines such as tri-ethanol amine or ethylene diamine. The amount of alkali is adjusted to give a final pH value of the gel mass less than or equal to about pH 9.0. In one embodiment, the final pH does not exceed 8.5. The volatile alkali neutralizing agent, ammonia is preferred. The film-forming polymer can then be combined with the plasticizer and solvent and then blended with the acid-insoluble gel to make a final homogeneous mix in a heat-controlled vessel and can be degassed by using vacuum. The fugitive ammonia evaporates during degassing. Using the foregoing process, the alkali concentrations do not require an additional step such as heating or neutralizing with acid in order to neutralize the gel mass.

In another embodiment described herein, an enteric soft capsule shell can be made by using an aqueous dispersion of the acid-insoluble polymer by adding alkaline materials such as ammonium, sodium, or potassium hydroxides, other alkalis, or a combination thereof that will cause the enteric acid-insoluble polymer to dissolve. The plasticizer-wetted, film-forming polymer can then be mixed with the solution of the acid-insoluble polymer. In one embodiment, enteric acid-insoluble polymers in the form of salts of the above-mentioned bases or alkalis can be dissolved directly in water and mixed with the plasticizer-wetted, film-forming polymer.

In one embodiment, an enteric soft capsule shell has the composition of Table 4, including all possible iterations of the specified ranges that provide 100% for the total weight percentage, including or excluding the optional, excipients, opacifiers, colorants, and flavorings.

TABLE 4

Exemplary Enteric Soft Capsule Shell Composition

| Component | Exemplary Component | Composition Range (%) |
|---|---|---|
| Film-forming polymer | Gelatin | 20-36 |
| Enteric, acid insoluble polymer | Methacrylic Acid Copolymer | 8-20 |
| Plasticizer | Glycerol, Triethyl citrate | 15-22 |
| Alkali neutralizing agents | NH$_4$OH (30%), NaOH | 1-5 |
| Solvent | Water | 20-40 |
| Opacifier | Titanium Dioxide | 1-7.5 |
| Colorant (optional) | Various | 0.05-1 |
| Flavoring (optional) | Various | 0.05-2 |
| Excipients (optional) | Various | 1-5 |

In one embodiment, an enteric soft capsule shell comprises a composition of about 30% film forming polymer (e.g., gelatin); about 10% enteric, acid insoluble polymer; about 20% plasticizer; about 1% alkali neutralizing agent; and about 37% solvent.

In one embodiment described herein, the enteric soft capsule described herein comprises a composition of about 3% film forming polymer (e.g., a composition of carrageenan); about 10% enteric, acid insoluble polymer; about 10% filler; about 10% plasticizer; about 1% alkali neutralizing agent; about 2% sealant; and about 60% solvent.

In one embodiment, the weight percentage range of total polymer content (i.e., film forming polymer and enteric acid-insoluble polymer) of the enteric soft capsule described herein is about 30% to about 45%, including all integers within the specified range. In another embodiment, the weight percentage range of total polymer content (i.e., film forming polymer and enteric acid-insoluble polymer) of the enteric soft capsule described herein is about 9% to about 35%, including all integers within the specified range. In one aspect, the total polymer weight percentage is about 40%. In another aspect, the total polymer weight percentage is about 42%. In another aspect, the total polymer weight percentage is about 45%. In another aspect, the total polymer weight percentage is about 38%. In another aspect, the total polymer weight percentage is about 12%. In another aspect, the total polymer weight percentage is about 16%.

In one embodiment, the weight percentage range of total plasticizer is about 15% to about 22%, including all iterations of integers with the specified range. In one aspect, the total plasticizer weight percentage is about 19%. In another aspect, the total plasticizer weight percentage is about 17.7%. In another aspect, the total plasticizer weight percentage is about 18.9%. In another aspect, the total plasticizer weight percentage is about 19.3%.

In one embodiment, the alkali neutralizing-agent is ammonia (ammonium hydroxide; 30% w/v) that is added to comprise a weight percentage of about 1 to about 5% of the total enteric soft capsule composition. In one aspect, 30% w/v ammonia is added to comprise a weight percentage of about 2%. In another aspect, 30% w/v ammonia is added to a weight percentage of about 1.7%. In one aspect, ammonia is added to provide a final pH of about 9 in the enteric soft capsule composition. In another aspect, ammonia is added to provide a final pH of about 8.5 in the enteric soft capsule composition. In another aspect, after the capsules are filled and dried, the ammonia concentration is substantially reduced, owing to the fugitive nature of the volatile alkali. In one aspect, practically all of the ammonia is evaporated except for ammonium ions comprising salts with other moieties in the composition.

In one embodiment, the weight ratio range of film forming polymer to enteric acid insoluble polymer (film forming: enteric) is about 25:75 (≈0.33) to about 40:60 (≈0.67) (i.e., ≈0.33-0.67), including all iterations of ratios within the specified range. In one aspect, the ratio of film forming polymer to enteric acid insoluble polymer is about 30:70 (≈0.43). In another aspect, the ratio of film forming polymer to enteric acid insoluble polymer is about 28:72 (≈0.38).

In another embodiment described herein, the weight ratio range of film forming polymer (i.e., total carrageenan composition) to enteric acid insoluble polymer (film forming: enteric) in the enteric soft gel composition is about 3:9 (≈0.3) to about 4:3 (≈1.3) (i.e., ≈0.3-1.3), including all ratios within the specified range. In some aspects, the ratio of film forming polymer to enteric acid insoluble polymer in the gel mass is about 1:3 (≈0.33), about 1:2.5 (≈0.4), about 1:2 (≈0.5), about 1:1.6 (≈0.6), about 1:1.25 (≈0.8), about 1:1 (≈1), about 1.1:1 (≈1.1), about 1.21 (≈1.2), or about 1.3:1 (≈1.3). In one aspect, the ratio of film forming polymer to enteric acid insoluble polymer in the gel mass is about 1:2.5 (≈0.4). In another aspect, the ratio of film forming polymer to enteric acid insoluble polymer is about 1:3 (≈0.3).

In one embodiment, the weight ratio of total plasticizer to film forming polymer is about 20:40 to 21:30 (i.e., ≈0.5-0.7), including all iterations of ratios within the specified range. In one aspect, the weight ratio of total plasticizer to film forming polymer is about 20:40 (≈0.5). In another aspect, the weight ratio of total plasticizer to film forming polymer is about 21:30 (≈0.7). In another aspect, the weight ratio of total plasticizer to film forming polymer is about 19:29 (≈0.65). In another aspect, the weight ratio of total plasticizer to film forming polymer is about 19.3:29.2 (≈0.66).

In one embodiment, the weight ratio of total plasticizer to enteric acid insoluble polymer is about 1:1 to about 2:1 (≈1-2), including all iterations of ratios within the specified range. In one aspect, the weight ratio of total plasticizer to enteric acid insoluble polymer is about 11:10 (≈1.1). In another aspect, the weight ratio of total plasticizer to enteric acid insoluble polymer is about 14:10 (≈1.4). In another aspect, the weight ratio of total plasticizer to enteric acid insoluble polymer is about 17:10 (≈1.7). In another aspect, the weight ratio of total plasticizer to enteric acid insoluble polymer is about 20:10 (≈2). In another aspect, the weight ratio of total plasticizer to enteric acid insoluble polymer is about 19.3:11.2 (≈1.73).

In one embodiment, the weight ratio range of total plasticizer to total polymer (film forming and enteric acid insoluble polymer) is about 18:45 to about 20:40 (i.e., ≈0.40-0.5), including all iterations of ratios within the specified range. In one aspect, the weight ratio range of total plasticizer to total polymer is about 18:45 (≈0.40). In another aspect, the weight ratio range of total plasticizer to total polymer is about 19:40 (≈0.475). In another aspect, the weight ratio range of total plasticizer to total polymer is about 20:40 (≈0.5). In another aspect, the weight ratio range of total plasticizer to total polymer is about 19.3:40.4 (≈0.477).

In one embodiment, the solvent comprises about 20% to about 40% of the enteric soft capsule composition, including all integers within the specified range. In one embodiment, the solvent is water. The quantity of water in the composition varies depending on the quantities of the other ingredients. For example, the quantity of opacifier, colorant, flavoring, or other excipients can change the percentage of water present the composition. In one embodiment, the weight percentage of water is as much as suffices to bring the total weight percentage to 100% (i.e., quantum sufficiat; q.s.). In another embodiment, the water comprises about 20%, about 25%, about 30%, about 35%, or about 40% of the enteric soft capsule composition. In another embodiment, water comprises about 35% to about 40% of the enteric soft capsule composition. In one embodiment, water comprises about 37% of the composition.

In one embodiment, the final moisture (water) content of the enteric soft capsule is from about 8% to about 15%, including all integers within the specified range. In another embodiment, the moisture content is about 8% to about 12%, including all integers within the specified range. In one aspect, the final moisture content is about 8%. In one aspect, the final moisture content is about 9%. In one aspect, the final moisture content is about 10%. In one aspect, the final moisture content is about 11%. In another aspect, the final moisture content is about 12%.

In one embodiment, the enteric soft capsule shell has the exemplary composition shown in Table 5.

TABLE 5

Exemplary Enteric Soft Capsule Shell Composition

| Component | Percent weight |
|---|---|
| Gelatin | 29.2 |
| Methacrylic Acid Copolymer (EUDRAGIT ® L 100) | 11.2 |
| Glycerol | 18.0 |
| Triethyl citrate | 1.3 |
| Ammonium hydroxide | 1.7 |
| Titanium dioxide | 1.5 |
| Water | 37.1 |
| TOTAL | 100% |
| Final pH | ~4-9 |
| Total polymer % weight (gelatin + enteric) | 40.4% |
| Gelatin % wt of total polymer (gelatin + enteric) | 72.4% |
| Enteric % wt of total polymer (gelatin + enteric) | 27.6% |
| Ratio of Enteric to Gelatin | 11.2:29.2 (0.38) |
| Total plasticizer % weight (glycerol + triethyl citrate) | 19.3% |
| Ratio of total plasticizer to total polymer | 19.3:40.4 (0.48) |
| Ratio total plasticizer to gelatin | 19.3:29.2 (0.66) |
| Ratio total plasticizer to enteric | 19.3:11.2 (1.73) |
| Water content in dried enteric soft capsule: | 8-15% |

In one embodiment, the enteric soft capsule shell comprises about 30% gelatin; about 10% poly(methyl) acrylate copolymer; about 18% glycerol; about 1% triethyl citrate; about 1.5% ammonia; about 37% water; and about 1.5% titanium dioxide.

One embodiment described herein provides an enteric acid-insoluble polymer dispersed within the film-forming polymer gel mass that provides the total soft gel composition with enteric acid-insoluble properties, at relatively low concentrations of the enteric acid-insoluble polymer (e.g., from about 8% to about 20% of the total wet gel mass composition) and without the need of excessive amounts of alkali, thus avoiding denaturation or degradation of the film-forming polymer that can weaken the integrity of the enteric soft capsule shell.

In some embodiments, the enteric soft capsule shell does not dissolve or disintegrate in acids, such as 0.1 N hydrochloric acid or simulated gastric fluid (ca. pH 1.2), despite the fact that the majority of the shell ingredients (i.e., greater than 50%) normally dissolve in, or are miscible with, acids. In some embodiments, the enteric soft capsules made using the compositions described herein remain intact in hydrochloric acid or simulated gastric fluid for at least two hours and the capsules readily release their contents upon shifting the pH of the solution to ca. 6.8, such as that of simulated intestinal fluid. In one aspect, the enteric soft capsule is resistant to dissolution at about pH 1.2 for at least about 2 hours. In another aspect, the enteric soft capsule begins dissolution at pH of about 6.8 within about 10 min.

In another embodiment, the final enteric capsule composition provides films of increased strength without substantially compromising film elasticity. Moreover, films made from the enteric soft capsule compositions as described herein can be sealed at normal temperature range typically used for making traditional soft gel capsules. In one aspect, enteric soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing enteric soft capsules comprising the pharmaceutical composition as described herein. The process includes preparing a gel mass composition comprising a film-forming, water-soluble polymer and an enteric acid-insoluble polymer and mixing with appropriate plasticizers and solvent; casting the gel mass into films or ribbons using heat-controlled drums or surfaces; and manufacturing a soft capsule comprising a matrix fill using rotary die technology. The thickness of the films or ribbons that form the enteric capsule shell is from about 0.010 inches ($\approx$0.254 mm) to about 0.050 inches ($\approx$1.27 mm), including all integers within the specified range. The shell thickness can be about 0.010 inch ($\approx$0.254 mm), about 0.015 inch ($\approx$0.381 mm), about 0.02 in ($\approx$0.508 mm), about 0.03 in ($\approx$0.762 mm), about 0.04 in ($\approx$1.02 mm), or about 0.05 in ($\approx$1.27 mm). In one embodiment, the thickness is about 0.02 inches ($\approx$0.508 mm) to about 0.040 inches ($\approx$1.02 mm). In one embodiment, the shell thickness is about 0.028 inches ($\approx$0.711 mm). In another embodiment, the shell thickness is about 0.033 inches ($\approx$0.838 mm). In another embodiment, the shell thickness is about 0.038 inches ($\approx$0.965 mm).

In one embodiment described herein, the enteric soft capsule shell described herein, encapsulates a matrix fill as described herein. In another embodiment described herein, the enteric soft capsule shell and encapsulated matrix fill comprises a outer dimension from about 2 oval to about 30 oval, including all iterations of capsule size within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the enteric soft capsule shell and encapsulated matrix fill comprises a outer dimension from about 2 round to about 28 round, including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the enteric soft capsule shell and encapsulated matrix fill comprises a outer dimension from about 2 oblong to about 22 oblong, including all iterations of capsule size within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). Dimension specifications of soft capsules and tablets are known to those skilled in the art. See *Remington's Essentials of Pharmaceutics*, Pharmaceutical Press Publishing Company, London, UK, 1$^{st}$ Edition, 2013, which is incorporated by reference herein for such teachings.

In another embodiment, the capsule is a soft capsule comprising a film-forming polymer that is stable at higher temperatures (e.g., about 50° C. to about 80° C.). An exemplary film-forming polymer is carrageenan (e.g., kappa or iota carrageenan). Exemplary, non-limiting soft capsules comprising carrageenan are described in the International Patent Application Publication No. WO 2003/061633; U.S. Patent Application Publication No. US 2004/0052839; and U.S. Pat. Nos. 6,949,256 and 7,887,838, each of which is incorporated by reference herein for such teachings. In one aspect, soft capsules comprising a film-forming polymer stable at high temperatures allow for matrix fills having a higher viscosity to be encapsulated minimizing the use of additional plasticizers. The increased encapsulation temperature, for example, from about 50° C. to about 80° C. allows for a viscous matrix at a lower temperature to exhibit flowability for encapsulation by the methods described herein (e.g., rotary die encapsulation).

In another embodiment, the capsule shell is a hard capsule shell. In one aspect, the hard capsule shell may comprise the abuse deterrent matrices described herein. Any hard capsule shell, for example hard capsule shells comprising gelatin, HPMC, or pullulan, including hard capsule shells exhibiting enteric properties, maybe used with the abuse deterrent matrix fills described herein. Hard capsule shells are known in the art and are described by Kathpalia et al., *J. Adv. Pharm. Edu. & Res.* 4(2): 165-177 (2014), which is incorporated by reference herein for its specific teachings thereof.

The pharmaceutical composition described herein can comprise a soft capsule comprising a matrix fill that is liquid, semi-solid, or solid. Capsules prepared as described herein can contain a hydrophobic solution or suspension, such as vegetable oils or shortening, or waxes, or combinations thereof. The matrix can be formulated to prevent interaction with the capsule shell components and release the pharmaceutical composition at a specified rate.

One embodiment described herein, is a pharmaceutical composition comprising a matrix fill formulation comprising any of the formulations shown in the Tables or Examples described herein. Any of the components of the formulations shown in the Tables or Examples can be increased, decreased, combined, recombined, switched, or removed to provide for a formulation comprising about 100% by weight.

In another embodiment, the abuse deterrent pharmaceutical composition described herein provides a dosage of an active pharmaceutical ingredient described herein for administration to a subject. The dosage form can be administered, for example, to a subject, or a subject in need thereof. In one aspect, the subject is a mammal, or a mammal in need thereof. In one aspect, the subject is a human, or human in need thereof. In one aspect, the human or human in need thereof is a medical patient. In one aspect, the human subject is a child (~0-9 years old) or an adolescent (~10-17 years old). In one aspect, the subject is from 0 to 9 years of age. In another aspect, the human subject is from 10 to 17 years of age. In another aspect, the human subject is over 17 years of age. In another aspect, the human subject is an adult (≥18 years of age).

In one embodiment, the dosage may be administered to a human in need of management of moderate to severe chronic pain and neuropathic pain associated with diabetic peripheral neuropathy (DPN), when a continuous, persistent (around-the-clock) opioid analgesic is needed for an extended period of time.

The dosage form can be administered, for example, 1×, 2×, 3×, 4×, 5×, 6×, or even more times per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition, including but not limited to, pain.

In one embodiment, the pharmaceutical composition described herein is administered in multiple dosages simultaneously. For example, two or more identical dosages are administered at one time. In another embodiment, two or more different dosages are administered at one time. Such dual or different simultaneous doses can be used to provide an effective amount of the pharmaceutical composition to a subject in need thereof.

In one embodiment, the abuse deterrent oral composition described herein, comprises one or more active pharmaceutical ingredients in an amount of about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, or even more.

In another embodiment, the abuse deterrent oral composition described herein, comprises one or more active pharmaceutical ingredients in the range of about 20 mg to about 250 mg, about 30 mg to about 250 mg, about 40 mg to about 250 mg, about 50 mg to about 250 mg, about 60 mg to about 250 mg, about 70 mg to about 250 mg, about 80 mg to about 250 mg, about 90 mg to about 250 mg, about 100 mg to about 250 mg, about 110 mg to about 250 mg, about 120 mg to about 250 mg, about 130 mg to about 250 mg, about 140 mg to about 250 mg, about 150 mg to about 250 mg, about 160 mg to about 250 mg, about 170 mg to about 250 mg, about 180 mg to about 250 mg, about 190 mg to about 250 mg, about 200 mg to about 250 mg, about 210 mg to about 250 mg, about 220 mg to about 250 mg, about 230 mg to about 250 mg, about 240 mg to about 250 mg; about 250 mg to about 500 mg, about 260 mg to about 500 mg, about 270 mg to about 500 mg, about 280 mg to about 500 mg, about 290 mg to about 500 mg, about 300 mg to about 500 mg, about 310 mg to about 500 mg, about 320 mg to about 500 mg, about 330 mg to about 500 mg, about 340 mg to about 500 mg, about 350 mg to about 500 mg, about 360 mg to about 500 mg, about 370 mg to about 500 mg, about 380 mg to about 500 mg, about 390 mg to about 500 mg, about 400 mg to about 500 mg, about 410 mg to about 500 mg, about 420 mg to about 500 mg, about 430 mg to about 500 mg, about 440 mg to about 500 mg, about 450 mg to about 500 mg, about 460 mg to about 500 mg, about 470 mg to about 500 mg, about 480 mg to about 500 mg, or about 490 mg to about 500 mg.

In one embodiment described herein, the abuse deterrent oral composition described herein may comprise an active pharmaceutical ingredient load (e.g., a drug load of one or more active pharmaceutical ingredients) of about 1% to about 90%, including each integer within the specified range. In one embodiment, the drug load can comprise about 1%, about 2%, about 2.5%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or even higher. In one aspect, the drug load is about 5%. In one aspect, the drug load is about 10%. In one aspect, the drug load is about 20%. In one aspect, the drug load is about 25%. In one aspect, the drug load is about 30%. In one aspect, the drug load is about 35%. In one aspect, the drug load is about 40%. In one aspect, the drug load is about 50%. In one aspect, the drug load is about 60%. In one aspect, the drug load is about 28%. In one aspect, the drug load is about 32%. In one aspect, the drug load is about 44%. In one embodiment, the drug load is about 48%.

In one embodiment, the active pharmaceutical ingredient is oxycodone, hydrocodone or codeine, or a salt, ether, ester, variant, or derivative thereof. In one embodiment, the active pharmaceutical ingredient is oxycodone. In another embodiment, the active pharmaceutical ingredient is hydrocodone. See Prescribing Information for OxyContin® ER 04/2014 (Purdue Pharma LP; available at www.purduepharma.com) and Zohydro® ER 01/2015 (Zogenix® Inc.; available at: www.zogenix.com), which are incorporated by reference herein for such teachings.

In another embodiment, the active pharmaceutical ingredient may comprise oxycodone, hydrocodone, or codeine and an additional active pharmaceutical ingredient. In one aspect, the additional active pharmaceutical ingredient prevents opioid abuse when an excess of opioid is used. In another aspect, the additional active pharmaceutical ingredient reduces or prevents opioid induced side effects.

In one embodiment, the abuse deterrent oral composition described herein comprises a dose of hydrocodone. In one aspect, the dose of hydrocodone is about 5 mg. In one aspect, the dose of hydrocodone is about 10 mg. In one aspect, the dose of hydrocodone is about 20 mg. In another aspect, the dose of hydrocodone is about 30 mg. In another aspect, the dose of hydrocodone is about 40 mg. In another aspect, the dose of hydrocodone is about 50 mg. In another aspect, the dose of hydrocodone is about 60 mg. In another aspect, the dose of hydrocodone is about 70 mg. In another aspect, the dose of hydrocodone is about 80 mg. In another aspect, the dose of hydrocodone is about 90 mg. In another aspect, the dose of hydrocodone is about 100 mg. In another aspect, the dose of hydrocodone is about 120 mg. In another aspect, the dose of hydrocodone is about 140 mg. In another aspect, the dose of hydrocodone is about 160 mg. In another aspect, the dose of hydrocodone is about 180 mg. In another aspect, the dose of hydrocodone is about 200 mg.

In one embodiment, the abuse deterrent oral composition described herein comprises a dose of oxycodone. In one aspect, the dose of oxycodone is about 5 mg. In another aspect, the dose of oxycodone is about 10 mg. In another aspect, the dose of oxycodone is about 15 mg. In another aspect, the dose of oxycodone is about 20 mg. In another aspect, the dose of oxycodone is about 30 mg. In another aspect, the dose of oxycodone is about 40 mg. In another aspect, the dose of oxycodone is about 50 mg. In another aspect, the dose of oxycodone is about 60 mg. In another aspect, the dose of oxycodone is about 70 mg. In another aspect, the dose of oxycodone is about 80 mg. In another aspect, the dose of oxycodone is about 100 mg. In another aspect, the dose of oxycodone is about 120 mg. In another aspect, the dose of oxycodone is about 140 mg. In another aspect, the dose of oxycodone is about 160 mg. In another aspect, the dose of oxycodone is about 180 mg. In another aspect, the dose of oxycodone is about 200 mg.

In another embodiment, the total dosage of oxycodone or hydrocodone administered in a 24-hour period is about 20 mg to about 600 mg per 24-hour period. In one aspect, the total dosage of oxycodone or hydrocodone administered in a 24-hour period is about 50 mg to about 250 mg per 24-hour period. The dosage can contain a total amount of oxycodone or hydrocodone effective for treatment, amelioration, prophylaxis, or reducing the onset of or symptoms of pain.

In one embodiment, the recommended dosage is based upon the condition of the subject in need thereof. The subject can comprise a human or mammal in need thereof. In one aspect, the need is defined as a painful condition or perception of pain. In one embodiment, the initial dosage of hydrocodone is 10 mg to about 40 mg. In one aspect, an initial dose of about 10 mg to about 40 mg is suitable for a subject that not tolerant of an opioid. In one aspect, the initial dose is about 10 mg of hydrocodone. In another aspect, the initial dose is about 20 mg of hydrocodone. In another aspect, the initial dose is about 20 mg of hydrocodone. In another aspect, the initial dose is about 30 mg of hydrocodone. In another aspect, the initial dose is about 40 mg of hydrocodone. In another aspect, the dose of hydrocodone may be maintained and given every 8 to 12 hours. In another aspect, the dose of hydrocodone may be increased by about 10 mg to about 20 mg every 8 hrs to 12 hrs until relief of a painful condition or the perception of pain occurs.

In another embodiment, the initial dosage of hydrocodone is 40 mg to about 80 mg. In one aspect, an initial dose of about 40 mg to about 80 mg is suitable for a subject that has an opioid tolerant phenotype. In one aspect, the initial dose is about 40 mg of hydrocodone. In another aspect, the initial dose is about 50 mg of hydrocodone. In another aspect, the initial dose is about 60 mg of hydrocodone. In another aspect, the initial dose is about 70 mg of hydrocodone. In another aspect, the initial dose is about 80 mg of hydrocodone. In another aspect, the dose of hydrocodone may be maintained and given every 8 to 12 hours. In another aspect, the dose of hydrocodone may be increased by about 10 mg to about 20 mg every 8 hrs to 12 hrs until relief of a painful condition or the perception of pain occurs.

In one embodiment, the recommended dosage is based upon the condition of the subject in need thereof. The subject can comprise a human or mammal in need thereof. In one aspect, the need is defined as a painful condition or perception of pain. In one embodiment, the initial dosage of oxycodone is 10 mg to about 40 mg. In one aspect, an initial dose of about 10 mg to about 40 mg is suitable for a subject that not tolerant of an opioid and a dose. In one aspect, the initial dose is about 10 mg of oxycodone. In another aspect, the initial dose is about 20 mg of oxycodone. In another aspect, the initial dose is about 20 mg of oxycodone. In another aspect, the initial dose is about 30 mg of oxycodone. In another aspect, the initial dose is about 40 mg of oxycodone. In another aspect, the dose of oxycodone may be maintained and given every 8 to 12 hours. In another aspect, the dose of oxycodone may be increased by about 10 mg to about 20 mg every 8 hrs to 12 hrs until relief of a painful condition or the perception of pain occurs.

In another embodiment, the initial dosage of oxycodone is 40 mg to about 160 mg. In one aspect, an initial dose of about 40 mg to about 80 mg is suitable for a subject that has an opioid tolerant phenotype. In one aspect, the initial dose is about 40 mg of oxycodone. In another aspect, the initial dose is about 50 mg of oxycodone. In another aspect, the initial dose is about 60 mg of oxycodone. In another aspect, the initial dose is about 70 mg of oxycodone. In another aspect, the initial dose is about 80 mg of oxycodone. In another aspect, the initial dose is about 100 mg of oxycodone. In another aspect, the initial dose is about 120 mg of oxycodone. In another aspect, the initial dose is about 140 mg of oxycodone. In another aspect, the initial dose is about 160 mg of oxycodone. In another aspect, the dose of oxycodone may be maintained and given every 8 to 12 hours. In another aspect, the dose of oxycodone may be increased by about 10 mg to about 20 mg every 8 hrs to 12 hrs until relief of a painful condition or the perception of pain occurs.

Additional pain that the abuse deterrent pharmaceutical composition described herein may be useful for the treatment of pain stemming from including, but not limited to, chronic arthritis, osteoarthritis, rheumatoid arthritis, acute tendonitis, bursitis, headaches, migraines, chronic neuropathies, shingles, premenstrual symptoms, sports injuries, malignancy, radiculopathy, sciatica/sciatic pain, sarcoidosis, necrobiosis, lipoidica, or granuloma annulare.

Another embodiment described herein is an abuse deterrent pharmaceutical composition as described herein for administration to a subject having pain, comprising a therapeutically effective amount of one or more active pharmaceutical ingredients exhibiting an in vitro dissolution rate at pH 6.8 comprising about 20% to about 80% dissolution after about 60 minutes to about 720 minutes including each integer within the specified ranges of dissolution and time. In another aspect, the in vitro dissolution rate at pH 6.8 is about 50% after about 280 minutes to about 720 minutes, including each integer with in the specified time range. In one aspect, the in vitro dissolution rate at pH 6.8 is about 50% after about 60 min, about 50% after about 70 min, about 50% after about 80 min, about 50% after about 90 min, about 50% after about 120 min, about 50% after about 150 min, about 50% after about 180 min, about 50% after about 210 min, about 50% after about 240 min, about 50% after about 300 min, is about 50% after about 330 min, about 50% after about 360 min, is about 50% after about 390 min, about 50% after about 420 min, about 50% after about 480 min, about 50% after about 540 min, about 50% after about 600 min, about 50% after about 660 min, about 50% after about 720 min, about 50% after about 780 min, about 50% after about 840 min, about 50% after about 900 min, about 50% after about 960 min, or about 50% after 1080 min.

In another embodiment, the abuse deterrent pharmaceutical composition comprising an abuse deterrent matrix as described herein reduces the dissolution and extraction of an active pharmaceutical ingredient. Suitable non-limiting examples of extraction methods comprise incubating the abuse deterrent pharmaceutical composition in boiling conditions, in aqueous solutions of alcohol, and in distilled water. These methods may be used in conjunction with additional means of agitating, for example, with paddles, dipping, vigorous shaking, physical manipulations, and the like.

In another embodiment, the abuse deterrent pharmaceutical composition as described herein has an in vitro dissolution rate at pH 6.8 of about 50% after about 240 to about 480 minutes. In another aspect, the in vitro dissolution rate at pH 6.8 is about 50% after about 300 to about 480 minutes. In another aspect, the in vitro dissolution rate at pH 6.8 is about 50% after about 320 to about 420 minutes. In another aspect, the in vitro dissolution rate at pH 6.8 is about 50% after about 300 to about 400 minutes. In another aspect, the in vitro dissolution rate at pH 6.8 is about 50% after about 320 minutes. In another aspect, the in vitro dissolution rate at pH 6.8 is about 50% after about 340 minutes. In another aspect, the in vitro dissolution rate at pH 6.8 is about 50% after about 360 minutes. In another aspect, the in vitro dissolution rate at pH 6.8 is about 50% after about 380 minutes. In another aspect, the in vitro dissolution rate at pH 6.8 is about 50% after about 400 minutes. In another aspect, the in vitro dissolution rate at pH 6.8 is about 50% after about 420 minutes. In another aspect, the in vitro dissolution rate at pH 6.8 is about 50% after about 440 minutes. In another aspect, the in vitro dissolution rate at pH 6.8 is about 50% after about 480 minutes. In another aspect, the in vitro dissolution rate at pH 6.8 is about 50% after about 500 minutes.

In another embodiment, the abuse deterrent pharmaceutical composition as described herein has an in vitro dissolution rate under boiling conditions in an aqueous media (e.g., a temperature of about 90° C. to about 120° C.) less than about 20% to about 80% after about 5 minutes to about 120 minutes including each integer within the specified ranges of dissolution and time. In one aspect, the in vitro dissolution rate of the controlled release pharmaceutical composition under boiling conditions in an aqueous media is less than about 50% after about 5 minutes. In another aspect, the in vitro dissolution rate of the controlled release pharmaceutical composition under boiling conditions in an aqueous media is less than about 50% after about 10 minutes. In another aspect, the in vitro dissolution rate of the controlled release pharmaceutical composition under boiling conditions in an aqueous media is less than about 50% after about 20 minutes. In another aspect, the in vitro dissolution rate of the controlled release pharmaceutical composition under boiling conditions in an aqueous media is less than about 50% after about 30 minutes. In another aspect, the in vitro dissolution rate of the controlled release pharmaceutical composition under boiling conditions in an aqueous media is less than about 50% after about 40 minutes. In another aspect, the in vitro dissolution rate of the controlled release pharmaceutical composition under boiling conditions in an aqueous media is less than about 50% after about 50 minutes. In another aspect, the in vitro dissolution rate of the controlled release pharmaceutical composition under boiling conditions in an aqueous media is less than about 50% after about 60 minutes. In another aspect, the in vitro dissolution rate of the controlled release pharmaceutical composition under boiling conditions in an aqueous media is less than about 50% after about 120 minutes.

In another embodiment, the abuse deterrent controlled release pharmaceutical composition as described herein has an in vitro dissolution rate in an aqueous alcohol solution (e.g., an aqueous solution of ethanol of 10% to 50% at a pH of about 1.2) of less than about 20% to about 50% after about 30 minutes to about 280 minutes including each integer within the specified ranges of dissolution and time. In another embodiment, the abuse deterrent controlled release pharmaceutical composition as described herein has an in vitro dissolution rate in an aqueous alcohol solution of less than about 50% after about 280 minutes to about 1440 minutes including each integer within the specified ranges of dissolution and time. In one aspect, the in vitro dissolution rate of the controlled release pharmaceutical composition in an aqueous alcohol solution is less than about 50% after about 30 minutes. In another aspect, the in vitro dissolution rate of the controlled release pharmaceutical composition in an aqueous alcohol solution is less than about 50% after about 45 minutes. In another aspect, the in vitro dissolution rate of the controlled release pharmaceutical composition in an aqueous alcohol solution is less than about 50% after about 60 minutes. In another aspect, the in vitro dissolution rate of the controlled release pharmaceutical composition in an aqueous alcohol solution is less than about 50% after about 120 minutes. In another aspect, the in vitro dissolution rate of the controlled release pharmaceutical composition in an aqueous alcohol solution is less than about 50% after about 180 minutes. In another aspect, the in vitro dissolution rate of the controlled release pharmaceutical composition in an aqueous alcohol solution is less than about 50% after about 360 minutes. In another aspect, the in vitro dissolution rate of the controlled release pharmaceutical composition in an aqueous alcohol solution is less than about 50% after about 720 minutes. In another aspect, the in vitro dissolution rate of the controlled release pharmaceutical composition in an aqueous alcohol solution is less than about 50% after about 960 minutes. In another aspect, the in vitro dissolution rate of the controlled release pharmaceutical composition in an aqueous alcohol solution is less than about 50% after about 1440 minutes.

In another embodiment, the abuse deterrent controlled release pharmaceutical composition as described herein has an in vitro dissolution rate in distilled water of less than about 20% to about 50% after about 30 minutes to about 280 minutes including each integer within the specified ranges of dissolution and time. In another embodiment, the abuse deterrent controlled release pharmaceutical composition as described herein has an in vitro dissolution rate in distilled water of less than about 50% after about 280 minutes to about 1440 minutes including each integer within the specified ranges of dissolution and time. In one aspect, the in vitro dissolution rate of the controlled release pharmaceutical composition in distilled water is less than about 50% after about 30 minutes. In another aspect, the in vitro dissolution rate of the controlled release pharmaceutical composition in distilled water is less than about 50% after about 45 minutes. In another aspect, the in vitro dissolution rate of the controlled release pharmaceutical composition in distilled water is less than about 50% after about 60 minutes. In another aspect, the in vitro dissolution rate of the controlled release pharmaceutical composition in distilled water is less than about 50% after about 120 minutes. In another aspect, the in vitro dissolution rate of the controlled release pharmaceutical composition in distilled water is less than about 50% after about 180 minutes. In another aspect, the in vitro dissolution rate of the controlled release pharmaceutical composition in distilled water is less than about 50% after about 360 minutes. In another aspect, the in vitro dissolution rate of the controlled release pharmaceutical composition in distilled water is less than about 50% after about 720 minutes. In another aspect, the in vitro dissolution rate of the controlled release pharmaceutical composition in distilled water is less than about 50% after about 960 minutes. In another aspect, the in vitro dissolution rate of the controlled release pharmaceutical composition in distilled water is less than about 50% after about 1440 minutes.

Another embodiment described herein is an abuse deterrent pharmaceutical composition as described herein comprising a therapeutically effective amount of one or more active pharmaceutical ingredients for administration to a subject having pain, exhibiting an in vitro dissolution rate at pH 6.8, of about 50% after about 60 minutes to about 480 minutes, an in vitro dissolution rate under boiling conditions less than about 20% to about 80% after about 5 minutes to about 120 minutes, and an in vitro dissolution rate in an aqueous alcohol solution or distilled water of less than about 50% after about 280 minutes to about 1440 minutes.

Another embodiment described herein is an abuse deterrent pharmaceutical composition as described herein comprising a therapeutically effective amount of one or more active pharmaceutical ingredients for administration to a subject having pain, exhibiting an in vitro dissolution rate as described herein in any one of Drawings 2-17.

Another embodiment described herein is a method for orally administering a dosage form of an abuse deterrent pharmaceutical composition comprising an active pharmaceutical ingredient described herein for the treatment, amelioration, prophylaxis, or reducing the onset of or symptoms of pain.

Another embodiment described herein is a method for treating, retarding the progression of, delaying the onset of, prophylaxis of, amelioration of, or reducing the symptoms of pain, comprising administering to a subject in need thereof an oral pharmaceutical composition as described herein comprising a therapeutically effective amount of one or more active pharmaceutical ingredients for administration to a subject having pain, wherein the pharmaceutical composition exhibits an in vitro dissolution rate at pH 6.8, of about 50% after about 60 minutes to about 480 minutes, an in vitro dissolution rate under boiling conditions less than about 20% to about 80% after about 5 minutes to about 120 minutes, and an in vitro dissolution rate in an aqueous alcohol solution or distilled water of less than about 50% after about 280 minutes to about 1440 minutes.

Another embodiment described herein is a method for treating, retarding the progression of, delaying the onset of, prophylaxis of, amelioration of, or reducing the symptoms of pain, comprising administering to a subject in need thereof an oral pharmaceutical composition as described herein comprising a therapeutically effective amount of one or more active pharmaceutical ingredients for administration to a subject having pain, exhibiting an in vitro dissolution rate as described herein in any one of Drawings 2-15.

Another embodiment described herein is a method for treating an individual having pain, with a pharmaceutical composition described herein comprising an abuse deterrent matrix described herein comprising a dosage of about 10 mg of oxycodone to about 80 mg of oxycodone, wherein subjects administered a single dosage exhibit a mean plasma oxycodone $C_{max}$ of about 10 ng/mL to about 150 ng/mL, including each integer within the specified range. In one aspect, the composition is provided in a dosage form containing a total amount of about 10 mg of oxycodone, wherein subjects administered a single dosage exhibit a mean plasma oxycodone $C_{max}$ of about 10 ng/mL. In another aspect, the composition is provided in a dosage form containing a total amount of about 20 mg of oxycodone, wherein subjects administered a single dosage exhibit a mean plasma oxycodone $C_{max}$ of about 20 ng/mL. In another aspect, the composition is provided in a dosage form containing a total amount of about 40 mg of oxycodone, wherein subjects administered a single dosage exhibit a mean plasma oxycodone $C_{max}$ of about 40 ng/mL. In another aspect, the composition is provided in a dosage form containing a total amount of about 80 mg of oxycodone, wherein subjects administered a single dosage exhibit a mean plasma oxycodone $C_{max}$ of about 100 ng/mL.

Another embodiment described herein is a method for treating an individual having pain, with a pharmaceutical composition described herein comprising an abuse deterrent matrix described herein comprising a dosage of about 10 mg of oxycodone to about 80 mg of oxycodone, wherein subjects administered a single dosage exhibit a mean plasma oxycodone $AUC_{0 \to \infty}$ of about 100 h·mg/L to about 1000 h·mg/L, including each integer within the specified range. In one aspect, the composition is provided in a dosage form containing a total amount of about 10 mg of a oxycodone, wherein subjects administered a single dosage exhibit a mean plasma oxycodone $AUC_{0 \to \infty}$ of about 100 h·mg/L. In another aspect, the composition is provided in a dosage form containing a total amount of about 20 mg of oxycodone, wherein subjects administered a single dosage exhibit a mean plasma oxycodone $AUC_{0 \to \infty}$ of about 200 h·mg/L. In another aspect, the composition is provided in a dosage form containing a total amount of about 40 mg of oxycodone, wherein subjects administered a single dosage exhibit a mean plasma oxycodone $AUC_{0 \to \infty}$ of about 400 h·mg/L. In another aspect, the composition is provided in a dosage form containing a total amount of about 80 mg of oxycodone, wherein subjects administered a single dosage exhibit a mean plasma oxycodone $AUC_{0 \to \infty}$ of about 1000 h·mg/L.

Another embodiment described herein is a method for treating an individual having pain, with a pharmaceutical composition described herein comprising an abuse deterrent matrix described herein comprising a dosage of about 10 mg of oxycodone to about 80 mg of oxycodone, wherein subjects administered a single dosage exhibits a $T_{max}$ of about 1 hr to about 8 hrs, including each integer within the specified range. In one aspect, the composition is provided in a dosage form containing a total amount of about 10 mg to about 80 mg of oxycodone, wherein subjects administered a single dosage exhibit a $T_{max}$ of about 1 hr, about 1.5 hrs, about 2 hrs, about 2.5 hrs, about 3 hrs, about 3.5 hrs, about 4 hrs, 4.5 hrs, 5 hrs, 5.5 hrs, 6 hrs, 6.5 hrs, 7 hrs, 7.5 hrs, or about 8 hrs.

Another embodiment described herein is a method for treating an individual having pain, with a pharmaceutical composition described herein comprising an abuse deterrent matrix described herein comprising a dosage of about 10 mg of hydrocodone to about 80 mg of hydrocodone, wherein subjects administered a single dosage exhibit a mean plasma hydrocodone $C_{max}$ of about 10 ng/mL to about 120 ng/mL, including each integer within the specified range. In one aspect, the composition is provided in a dosage form containing a total amount of about 10 mg of a hydrocodone, wherein subjects administered a single dosage exhibit a mean plasma hydrocodone $C_{max}$ of about 20 ng/mL. In another aspect, the composition is provided in a dosage form containing a total amount of about 20 mg of hydrocodone, wherein subjects administered a single dosage exhibit a mean plasma hydrocodone $C_{max}$ of about 30 ng/mL. In another aspect, the composition is provided in a dosage form containing a total amount of about 30 mg of hydrocodone, wherein subjects administered a single dosage exhibit a mean plasma hydrocodone $C_{max}$ of about 40 ng/mL. In another aspect, the composition is provided in a dosage form containing a total amount of about 40 mg of hydrocodone, wherein subjects administered a single dosage exhibit a mean plasma hydrocodone $C_{max}$ of about 60 ng/mL. In another aspect, the composition is provided in a dosage form containing a total amount of about 80 mg of hydrocodone, wherein subjects administered a single dosage exhibit a mean plasma hydrocodone $C_{max}$ of about 120 ng/mL.

Another embodiment described herein is a method for treating an individual having pain, with a pharmaceutical composition described herein comprising an abuse deterrent matrix described herein comprising a dosage of about 10 mg of hydrocodone to about 80 mg of hydrocodone, wherein subjects administered a single dosage exhibit a mean plasma hydrocodone $AUC_{0 \to \infty}$ of about 100 h·mg/L to about 1600 h·mg/L, including each integer within the specified range. In one aspect, the composition is provided in a dosage form containing a total amount of about 10 mg of a hydrocodone, wherein subjects administered a single dosage exhibit a mean plasma hydrocodone $AUC_{0 \to \infty}$ of about 150 h·mg/L. In another aspect, the composition is provided in a dosage form containing a total amount of about 20 mg of hydrocodone, wherein subjects administered a single dosage exhibit a mean plasma hydrocodone $AUC_{0 \to \infty}$ of about 400 h·mg/L. In another aspect, the composition is provided in a dosage form containing a total amount of about 40 mg of hydrocodone, wherein subjects administered a single dosage exhibit a mean plasma hydrocodone $AUC_{0 \to \infty}$ of about 850 h·mg/L. In another aspect, the composition is provided in a dosage form containing a total amount of about 80 mg of hydrocodone, wherein subjects administered a single dosage exhibit a mean plasma hydrocodone $AUC_{0 \to \infty}$ of about 1600 h·mg/L.

Another embodiment described herein is a method for treating an individual having pain, with a pharmaceutical composition described herein comprising an abuse deterrent matrix described herein comprising a dosage of about 10 mg of hydrocodone to about 80 mg of hydrocodone, wherein subjects administered a single dosage exhibits a $T_{max}$ of about 3 hrs to about 8 hrs, including each integer within the specified range. In one aspect, the composition is provided in a dosage form containing a total amount of about 10 mg to about 80 mg of hydrocodone, wherein subjects administered a single dosage exhibit a $T_{max}$ of about 3 hrs, about 4 hrs, about 5 hrs, about 6 hrs, about 7 hrs, or about 8 hrs.

In another embodiment, the pharmaceutical compositions described herein further comprise one or more active pharmaceutical ingredient(s) suitable for treating, ameliorating, or prophylactically treating a bowel dysfunction due to acute or chronic opioid use, often referred to as opioid induced bowel disfunction (OIBD). Symptoms of OIBD typically comprise constipation (e.g., opioid induced constipation; OIC), anorexia, nausea and vomiting, gastro-oesophageal reflux, delayed digestion, abdominal pain, flatulence, bloating, hard stools, incomplete evacuation or straining during bowel movements. Alternative or additional uses for the one or more active pharmaceutical ingredient(s) described herein may be to treat, reduce, inhibit, or prevent additional effects of acute or chronic opioid use including, e.g., aberrant migration or proliferation of endothelial cells (e.g., vascular endothelial cells), increased angiogenesis, and increase in lethal factor production from opportunistic infectious agents (e.g., *Pseudomonas aeruginosa*). Additional advantageous uses of one or more active pharmaceutical ingredient(s) include treatment of opioid-induced immune suppression, inhibition of angiogenesis, inhibition of vascular proliferation, treatment of pain, treatment of inflammatory conditions such as inflammatory bowel syndrome, treatment of infectious diseases and diseases of the musculoskeletal system such as osteoporosis, arthritis, osteitis, periostitis, myopathies, and treatment of autoimmune diseases, terminally ill patients receiving opioid therapy such as an AIDS patient, a cancer patient, a cardiovascular patient; subjects receiving opioid therapy for maintenance of opioid withdrawal. In one aspect, the subject is a subject using an opioid for chronic pain management. In another aspect, the subject is a subject using an acutely using an opioid for temporary pain management. In another aspect, the subject is a terminally ill patient. In another aspect, the subject is a person receiving opioid withdrawal maintenance therapy.

In another embodiment, suitable active pharmaceutical ingredients for treating a symptom or condition of opioid use may comprise a laxative such as lubiprostone, linaclotide, lactulose, and a heavy molecular weight poly ethylene glycol (e.g., PEG 3350; Miralax®; GlycoLax), sorbitol, calcium carbonate, potassium phosphate, magnesium hydroxide, psyllium, glycerin, polycarbophil, or docusate, or a mixture or combination thereof. In some aspects, other suitable pharmaceutical ingredients may comprise a natural therapeutic or nutraceutical comprising barberry, cascara sagrada, flax, or senna or a mixture or combination thereof. In some further aspects, suitable active pharmaceutical ingredients for the treatment, amelioration, or prophylaxis of OIBD or OIC comprise a peripherally acting mu-opioid receptor antagonist (PAMORA). In some aspects, the PAMORA comprises methylnaltrexone, naltrexone, naloxone, naloxegol, or alvimopan, or a mixture or combination thereof.

It is understood that activation of mu-opiod receptors along the gastro intestinal tract are responsible for decreased bowel function and constipation. Thus, without being bound by any theory, PAMORAs are useful for preventing symptoms of OIBD, and specifically OIC, by inhibiting the action of the mu-opioid receptor peripherally along the gastro-intestinal tract without inhibiting the mu-opiod receptors of the central nervous system (CNS). Therefore, a combination of an opioid agonist (e.g., oxycodone or hydrocodone) activates the CNS receptors and the co-administration of a PAMORA inhibits the peripheral gut mu-opioid receptors, which are believed to be responsible for the incurrence of OIC.

In one embodiment, the pharmaceutical compositions described herein comprise a dose of an opioid (e.g., oxycodone or hydrocodone) and a dose of a PAMORA. In one aspect, the pharmaceutical compositions described herein comprise a dose of an opioid and a dose of a PAMORA comprising naloxone or a pharmaceutically acceptable salt form thereof. In one aspect, the pharmaceutical compositions described herein comprise a dose of an opioid and a dose of a PAMORA comprising naltrexone or a pharmaceutically acceptable salt form thereof. In another aspect, the pharmaceutical compositions described herein comprise a dose of an opioid and a dose of a PAMORA comprising methylnaltrexone or a pharmaceutically acceptable salt form thereof. In another aspect, the pharmaceutical compositions described herein comprise a dose of an opioid and a dose of a PAMORA comprising naloxegol or a pharmaceutically acceptable salt form thereof.

In one embodiment, the pharmaceutical composition described herein comprises a dose of a PAMORA (e.g., naloxegol, naloxone, methylnaltrexone, or naltrexone) and a dose of an opioid (e.g., hydrocodone or oxycodone). In one aspect, the dose of the PAMORA ranges from about 50 mg to about 600 mg and the dose of the opioid is from about 5 mg to about 150 mg, including every integer within the specified ranges. In another aspect, the dose of the PAMORA ranges from about 50 mg to about 550 mg and the dose of the opioid is from about 5 mg to about 150 mg, including every integer within the specified ranges. In another aspect, the dose of the PAMORA ranges from about 5 mg to about 50 mg and the dose of the opioid is from about 5 mg to about 100 mg, including every integer within the specified ranges.

In another embodiment, the weight percentage ratio range of PAMORA (e.g., naloxegol, naloxone, methylnaltrexone, or naltrexone) to opioid (e.g., hydrocodone or oxycodone) in the pharmaceutical composition described herein ranges from about 15:1 to about 1:18, including each ratio within the specified range. In one aspect, the weight percentage ratio range of PAMORA (e.g., naloxegol, naloxone, methylnaltrexone, or naltrexone) to opioid is from about 13:1 to about 1:1, including each ratio within the specified range. In another aspect, the weight percentage ratio range of PAMORA (e.g., naloxegol, naloxone, methylnaltrexone, or naltrexone) to opioid is from about 1:16 to about 1:1, including each ratio within the specified range. In another aspect, the weight percentage ratio range of PAMORA to opioid is about 1:16, about 1:15, about 1:14, about 1:13, about 1:12, about 1:11, about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, about 10:1, about 11:1, about 12:1, about 13:1, about 14:1, or about 15:1.

In one embodiment, the pharmaceutical composition described herein comprises a dose of naloxone and a dose of an opioid comprising hydrocodone or oxycodone as described herein. In one aspect, the dose of the naloxone ranges from about 2.5 mg to about 100 mg, including each integer within the specified range. In another aspect, the dose of naloxone ranges from about 2.5 mg to about 50 mg, including each integer within the specified range. In another aspect, the dose of naloxone ranges from about 10 mg to about 50 mg, including each integer within the specified range. In another aspect, the dose of naloxone ranges from about 20 mg to about 40 mg, including each integer within the specified range. In another aspect, the dose of naloxone is about 2.5 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

In another embodiment, the weight percentage ratio range of naloxone to opioid comprising hydrocodone or oxycodone in the pharmaceutical composition described herein ranges from about 1:10 to about 5:1, including all iterations of ratios within the specified range. In one aspect, the weight percentage ratio range of naloxone to opioid comprising hydrocodone or oxycodone is from about 1:5 to about 1:1, including all iterations of ratios within the specified range. In another aspect, the weight percentage ratio range of naloxone to opioid comprising hydrocodone or oxycodone is from about 1:4 to about 1:2, including all iterations of ratios within the specified range. In another aspect, the weight percentage ratio range of naloxone to opioid comprising hydrocodone or oxycodone is about 1:10, about 1:9, about 1:8, about 1:7, about 1:6, about 1:5, about 1:4, about 1:3, about 1:2, about 1:1, about 2:1, about 3:1, about 4:1, or about 5:1. In another aspect, the weight percentage ratio range of naloxone to opioid comprising hydrocodone or oxycodone is about 1:2.

In another embodiment, the pharmaceutical composition described herein comprises a dose of about 5 mg of naloxone and a dose of about 10 mg of oxycodone. In another embodiment, the pharmaceutical composition described herein comprises a dose of about 10 mg of naloxone and a dose of about 20 mg of oxycodone. In another embodiment, the pharmaceutical composition described herein comprises a dose of about 20 mg of naloxone and a dose of about 40 mg of oxycodone. In another embodiment, the pharmaceutical composition described herein comprises a dose of about 40 mg of naloxone and a dose of about 80 mg of oxycodone. In another embodiment, the pharmaceutical composition described herein comprises a dose of about 80 mg of naloxone and a dose of about 160 mg of oxycodone.

In another embodiment, the pharmaceutical composition described herein comprises a dose of about 5 mg of naloxone and a dose of about 10 mg of hydrocodone. In another embodiment, the pharmaceutical composition described herein comprises a dose of about 10 mg of naloxone and a dose of about 20 mg of hydrocodone. In another embodiment, the pharmaceutical composition described herein comprises a dose of about 20 mg of naloxone and a dose of about 40 mg of hydrocodone. In another embodiment, the pharmaceutical composition described herein comprises a dose of about 40 mg of naloxone and a dose of about 80 mg of hydrocodone. In another embodiment, the pharmaceutical composition described herein comprises a dose of about 80 mg of naloxone and a dose of about 160 mg of hydrocodone.

In another embodiment, the pharmaceutical composition described herein comprises a dose of about 40 mg of oxycodone and a dose of about 20 mg of naloxone. In one aspect, the composition is provided in a dosage form containing a total amount of about 40 mg of a oxycodone and about 20 mg of naloxone, wherein subjects administered a single dosage exhibit a mean plasma oxycodone $AUC_{0\to\infty}$ of about 400 h·mg/L to about 600 h·mg/L and a mean plasma naloxone $AUC_{0\to\infty}$ of about 500 h·mg/L to about 600 h·mg/L. In another aspect, the composition is provided in a dosage form containing a total amount of about 40 mg of oxycodone and about 20 mg of naloxone, wherein subjects administered a single dosage exhibit a mean plasma oxycodone $C_{max}$ of about 30 ng/mL to about 50 ng/mL and a mean plasma naloxone $C_{max}$ of about 50 ng/mL to about 70 ng/mL. In another aspect, the composition is provided in a dosage form containing a total amount of about 40 mg of oxycodone and about 20 mg of naloxone, wherein subjects administered a single dosage exhibit an oxycodone $T_{max}$ of about 1 hr to about 5 hrs and a naloxone $T_{max}$ of about 0.5 hr to about 3 hrs.

In one embodiment, the pharmaceutical composition described herein comprises a dose of methylnaltrexone or naltrexone and a dose of an opioid comprising hydrocodone or oxycodone as described herein. In one aspect, the dose of the methylnaltrexone or naltrexone ranges from about 2.5 mg to about 100 mg, including each integer within the specified range. In another aspect, the dose of methylnaltrexone or naltrexone ranges from about 50 mg to about 600 mg, including each integer within the specified range. In another aspect, the dose of methylnaltrexone or naltrexone ranges from about 100 mg to about 600 mg, including each integer within the specified range. In another aspect, the dose of methylnaltrexone or naltrexone ranges from about 300 mg to about 600 mg, including each integer within the specified range. In another aspect, the dose of methylnaltrexone or naltrexone ranges from about 400 mg to about 600 mg, including each integer within the specified range. In another aspect, the dose of methylnaltrexone or naltrexone is about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, or about 550 mg.

In another embodiment, the weight percentage ratio range of methylnaltrexone or naltrexone to opioid comprising hydrocodone or oxycodone in the pharmaceutical composition described herein ranges from about 13:1 to about 1:1, including all iterations of ratios within the specified range. In one aspect, the weight percentage ratio range of methylnaltrexone or naltrexone to opioid comprising hydrocodone or oxycodone is from about 10:1 to about 1:1, including all iterations of ratios within the specified range. In another aspect, the weight percentage ratio range of methylnaltrexone or naltrexone to opioid comprising hydrocodone or oxycodone is from about 5:1 to about 1:1, including all iterations of ratios within the specified range. In another aspect, the weight percentage ratio range of methylnaltrexone or naltrexone to opioid comprising hydrocodone or oxycodone is about 1:1, about 2:1, about 3:1, about 4:1, about 5:1, about 6:1, about 7:1, about 8:1, about 9:1, about 10:1, about 11:1, about 12:1, or about 13:1.

In one embodiment, the pharmaceutical composition described herein comprises a dose of naloxegol and a dose of an opioid comprising hydrocodone or oxycodone as described herein. In one aspect, the dose of the naloxegol ranges from about 2.5 mg to about 100 mg, including each integer within the specified range. In another aspect, the dose of naloxegol ranges from about 2.5 mg to about 50 mg, including each integer within the specified range. In another aspect, the dose of naloxegol ranges from about 10 mg to about 50 mg, including each integer within the specified range. In another aspect, the dose of naloxegol ranges from about 20 mg to about 40 mg, including each integer within the specified range. In another aspect, the dose of naloxegol is about 2.5 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

In another embodiment, the weight percentage ratio range of naloxegol to opioid comprising hydrocodone or oxycodone in the pharmaceutical composition described herein ranges from about 1:10 to about 5:1, including all iterations of ratios within the specified range. In one aspect, the weight percentage ratio range of naloxegol to opioid comprising hydrocodone or oxycodone is from about 1:5 to about 1:1, including all iterations of ratios within the specified range. In another aspect, the weight percentage ratio range of naloxegol to opioid comprising hydrocodone or oxycodone is from about 1:4 to about 1:2, including all iterations of ratios within the specified range. In another aspect, the weight percentage ratio range of naloxegol to opioid comprising hydrocodone or oxycodone is about 1:10, about 1:9, about 1:8, about 1:7, about 1:6, about 1:5, about 1:4, about 1:3, about 1:2, about 1:1, about 2:1, about 3:1, about 4:1, or about 5:1. In another aspect, the weight percentage ratio range of naloxegol to opioid comprising hydrocodone or oxycodone is about 1:2.

Another embodiment described herein is a method for treating, retarding the progression of, prophylaxis of, delaying the onset of, ameliorating, or reducing the symptoms of pain comprising the administration of a therapeutically effective amount of one or more abuse deterrent pharmaceutical compositions described herein to a subject with pain, wherein the administration is sufficient to achieve a reduction pain relative to baseline in the subject without substantially inducing one or more side effects including, but not limited to, headache, vertigo, somnolence, nausea, constipation, vomiting, xerostomia, fatigue, pruritus, eructation, heartburn, abdominal discomfort, or loss of appetite.

Another embodiment described herein is a method for treating, retarding the progression of, prophylaxis of, delaying the onset of, ameliorating, or reducing the symptoms of pain comprising the administration of a therapeutically effective amount of one or more abuse deterrent pharmaceutical compositions described herein to a subject with pain, wherein the administration is sufficient to achieve a reduction pain relative to baseline in the subject without substantially inducing one or more side effects including, but not limited to, opioid use, such as, for example, opioid induced bowel dysfunction, opioid induced constipation, gastrointestinal dysfunction (e.g., inhibition of intestinal motility, constipation, GI sphincter constriction), nausea, emesis (vomiting), biliary spasm, colic, dysphoria, pruritus, urinary retention, depression of respiration, papillary constriction, cardiovascular effects, chest wall rigidity and cough suppression, depression of stress response, and immune suppression associated with use of narcotic analgesia, etc., or combinations thereof.

Another embodiment described herein is a method for treating, retarding the progression of, prophylaxis of, delaying the onset of, ameliorating, or reducing the symptoms of, irritable bowel syndrome, colitis, post-operative or postpartum ileus, nausea and/or vomiting, decreased gastric motility and emptying, inhibition of the stomach, and small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, idiopathic constipation, post-operative gastrointestinal dysfunction following abdominal surgery (e.g., colectomy (e.g., right hemicolectomy, left hemicolectomy, transverse hemicolectomy, colectomy takedown, low anterior resection)), and delayed absorption of orally administered medications or nutritive substances comprising the administration of a therapeutically effective amount of one or more abuse deterrent pharmaceutical compositions described herein.

Another embodiment described herein is a method for improving the quality of life of subjects receiving opioids, as well as to reduce complications arising from chronic constipation, such as hemorrhoids, appetite suppression, mucosal breakdown, sepsis, colon cancer risk, and myocardial infarction comprising the administration of a therapeutically effective amount of one or more abuse deterrent pharmaceutical compositions described herein.

In another embodiment, a the pharmaceutical composition described herein provides for a dosage form, which comprises an opioid and a PAMORA as described in, which in terms of efficacy, is ranked good or very good by more than 50% of patients, 60%, 70%, 80%, 90% or more of patients. In aspect, the dosage form is provided which comprises an opioid and a PAMORA as described in, which in terms of tolerability, is ranked good or very good by more than 50% of patients, 60%, 70%, 80%, 90% or more of patients.

In another embodiment, a the pharmaceutical composition described herein provides for a dosage form, which comprises an opioid and a PAMORA as described in, which provides a reduction of days with laxative intake by at least 10%, 20%, 30%, 40%, 50%, 60%, 70%, 80%, or even 90%.

In one aspect, the dosage form completely reduces the need for laxative to be taken independently.

In some embodiments, bowel function is assessed by observing parameters that are associated with bowel function. In particular, bowel function may be determined based on parameters selected from ease or difficulty of defecation, feeling of incomplete bowel evacuation, and/or personal judgment of patient regarding constipation. Other parameters which may be observed alternatively or in addition in order to assess the bowel function of a patient include among other things stool frequency, stool consistency, cramping, and painful laxation. Bowel function may be assessed by measuring parameters, which are associated with bowel function using numerical analog scales (NAS) for these parameters because this may provide more accurate results. This approach is particularly advantageous when assessing the bowel function in patients receiving treatment with analgesics, because analgesic efficacy of drugs is usually assessed using a numeric analog scale.

In some embodiments, a pharmaceutical composition is provided comprising an opioid and PAMORA as described herein to provide an improvement of the bowel function characterized by an improvement of the mean bowel function score of at least 5, at least about 8, at least about 10 or at least about 15 after administration at steady state or of a single dose to human patients or healthy human subjects, wherein the mean bowel function score is measured with a numerical analog scale ranging from 0 to 100.

In one embodiment, the bowel function is assessed by the bowel function index (BFI), which is measured in patients. The mean bowel function score may be determined by a method for assessing bowel function in a patient comprising the steps of: providing the patient with a numeric analog scale for at least one parameter, which parameter is associated with bowel function; causing the patient to indicate on the numeric analog scale the amount and/or intensity of the parameter being experienced; and observing the amount and/or intensity of the at least one parameter indicated on the numeric analog scale in order to assess bowel function. In one aspect the patient indicates the amount and/or intensity of parameter being experienced during the last days or weeks, e.g. during the last 1, 2, 3, 4, 5, 6, 7, 10, or 14 days. In another aspect, the numerical analog scale on which the patient indicates his/her subjective experience of the observed parameter may have any size or form and may range from 0 or any other number to any number, such as from 0 to 10 or from 0 to 50 or from 0 to 300 or from 1 to 10.

In another embodiment, if more than one parameter is observed, a mean bowel function may be obtained in form of a numerical value. This numerical value is the mean of the parameters observed, e.g., the three numeric analog scale values for ease or difficulty of defecation, feeling of incomplete bowel evacuation and judgment of constipation. The parameters, which are measures of bowel function or which are associated with bowel function, may comprise opioid induced bowel dysfunctions (OIBD or OIC) as described herein.

In another embodiment, bowel function may be determined based on the following parameters: ease or difficulty of defecation, for example during the last 7 days according to the patient assessment, wherein 0 corresponds to no difficulties and 100 corresponds to severe difficulties; feeling of incomplete bowel evacuation, for example during the last 7 days according to the patient assessment, wherein 0 corresponds to no feeling of incomplete bowel evacuation and 100 corresponds to very strong feeling of incomplete bowel evacuation; personal judgment of patient regarding constipation, for example during the last 7 days, wherein 0 corresponds to no constipation at all and 100 corresponds to very heavy constipation.

In another embodiment, bowel function may be assessed with analogs scales as described in U.S. Pat. No. 6,258,042 and International Patent Application Publication No. WO 2003/073937, which may be adapted to devices or analog scales as described above as would be understood by one of ordinary skill in the art. The disclosures of these two references are hereby incorporated by reference for such teachings.

In another embodiment, the pharmaceutical compositions described herein further comprise one or more active pharmaceutical ingredient(s), which prevent drug abuse by inhibiting the action or effects of an opioid. In one aspect, the pharmaceutical composition comprises an opioid (e.g., hydrocodone or oxycodone) and one or more abuse deterrent aversive agents. The abuse deterrent aversive agent may be any one of the a laxative such as lubiprostone, linaclotide, lactulose, and a heavy molecular weight poly ethylene glycol (e.g., PEG 3350; Miralax®; GlycoLax), sorbitol, calcium carbonate, potassium phosphate, magnesium hydroxide, psyllium, glycerin, polycarbophil, or docusate, or a mixture or combination thereof. Further abuse deterrent aversive agents may comprise methylnaltrexone, naltrexone, naloxone, naloxegol, or alvimopan, or a mixture or combination thereof. The aversive effect of the abuse deterrent aversive agent may include any unpleasant side effect comprising inducing opioid withdrawal symptoms, diarrhea, nausea, reduced euphoria or a mixture or combination thereof.

In another embodiment, the abuse deterrent pharmaceutical composition described herein is contained and dispensed from a tamper evident packaging. The term "tamper evident" or "tamper resistant" refers to a packaging of any kind that readily displays or allows for an individual to observe any physical interference or manipulation of said packaging. The tamper evident packaging provides reasonable evidence to consumers that tampering has occurred. The tamper evident packaging additionally contains appropriate labelling statements describing the features and evidences of the tamper evident packaging. In one aspect, the tamper evident packaging comprises: bottles, film wrappers, blister or strip packs, bubble packs, heat shrink bands or wrappers, foil, paper, or plastic pouches, container mouth inner seals, tape seals, breakable caps, sealed metal tubes or plastic heat-sealed tubes, sealed cartons, aerosol containers, cans including metal and composite materials, or any combination thereof. The packaging may also contain appropriate instructions for prescribing, instructions for use, warnings, or other appropriate information.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The ratios of the mass of any component of any of the formulations disclosed herein to the mass of any other component in the formulation or to the total mass of the other components in the formulation are hereby disclosed as if they were expressly disclosed. All patents and publications cited herein are incorporated by reference herein for the specific teachings thereof.

EXAMPLES

Example 1

Abuse deterrent matrices as described herein were prepared using the composition shown in Tables 7-16. The composition was prepared according to the method of Example 2 and encapsulated in a soft capsule shell. Other suitable non-limiting capsule shells for the abuse deterrent matrices described herein comprise an enteric soft capsule shell, a hard capsule shell, and an enteric hard capsule shell.

TABLE 7

Exemplary Abuse Deterrent Controlled Release Matrix Composition

| Components | Mass (mg/capsule) | Percentage (%) |
|---|---|---|
| Soybean Oil | 111.6 | 58.7 |
| Ethocel ™ (4 cP) | 9 | 4.7 |
| Carnauba Wax | 1.8 | 0.9 |
| Bee's Wax | — | — |
| Methocel ™ A4M | 18 | 9.5 |
| Polyethylene Glycol 400 | 36 | 18.9 |
| Microcrystalline Cellulose | 3.6 | 1.9 |
| BHT | — | — |
| BHA | — | — |
| Hydrocodone | 10 | 5.3 |
| TOTAL | 190 | 100 |

TABLE 8

Exemplary Abuse Deterrent Controlled Release Matrix Composition

| Components | Percentage (%) |
|---|---|
| Soybean Oil | 63.2 |
| Ethocel ™ (4 cP) | 3.4 |
| Carnauba Wax | 3.4 |
| Bee's Wax | — |
| Methocel ™ A4M | 11.5 |
| Polyethylene Glycol 400 | 11.5 |
| Microcrystalline Cellulose | 1.2 |
| BHT | — |
| BHA | — |
| Hydrocodone | 5.6 |
| TOTAL | 100 |

TABLE 9

Exemplary Abuse Deterrent Controlled Release Matrix Composition

| Components | Mass (mg/capsule) | Percentage (%) |
|---|---|---|
| Soybean Oil | 266.6 | 66.6 |
| Ethocel ™ (4 cP) | 14 | 3.5 |
| Carnauba Wax | 4 | 1 |
| Bee's Wax | 10 | 2.5 |
| Methocel ™ A4M | 20 | 5 |

TABLE 9-continued

Exemplary Abuse Deterrent Controlled Release Matrix Composition

| Components | Mass (mg/capsule) | Percentage (%) |
|---|---|---|
| Polyethylene Glycol 400 | 40 | 10 |
| Microcrystalline Cellulose | 4 | 1 |
| BHT | 0.4 | 0.1 |
| BHA | 1 | 0.25 |
| Oxycodone | 40 | 10 |
| TOTAL | 400 | 100 |

TABLE 10

Exemplary Abuse Deterrent Controlled Release Matrix Composition

| Components | Mass (mg/capsule) | Percentage (%) |
|---|---|---|
| Soybean Oil | 244.6 | 60.9 |
| Ethocel ™ (20 cP) | 12 | 3.0 |
| Carnauba Wax | 26 | 5.0 |
| Bee's Wax | 12 | 3.0 |
| Methocel ™ A4M | 36 | 7.5 |
| Polyethylene Glycol 400 | 40 | 10 |
| Microcrystalline Cellulose | — | — |
| BHT | 1 | 0.25 |
| BHA | 0.4 | 0.01 |
| Oxycodone | 42 | 10.4 |
| TOTAL | 402 | 100 |

TABLE 11

Exemplary Abuse Deterrent Controlled Release Matrix Composition

| Components | Mass (mg/capsule) | Percentage (%) |
|---|---|---|
| Soybean Oil | 244.6 | 60.9 |
| Ethocel ™ (20 cP) | 12 | 3.0 |
| Carnauba Wax | 26 | 6.5 |
| Bee's Wax | — | — |
| Methocel ™ A4M | 36 | 9.0 |
| Polyethylene Glycol 400 | 40 | 10 |
| Microcrystalline Cellulose | — | — |
| BHT | 1 | 0.25 |
| BHA | 0.4 | 0.10 |
| Oxycodone | 42 | 10.4 |
| TOTAL | 402 | 100 |

TABLE 12

Exemplary Abuse Deterrent Controlled Release Matrix Composition

| Components | Mass (mg/capsule) | Percentage (%) |
|---|---|---|
| Soybean Oil | 270.28 | 67.57 |
| Ethocel ™ (20 cP) | 8 | 2 |
| Carnauba Wax | — | — |
| Bee's Wax | 16 | 4 |
| Methocel ™ A4M | 20 | 5 |
| Polyethylene Glycol 400 | 40 | 10 |
| Microcrystalline Cellulose | 4 | 1 |

TABLE 12-continued

Exemplary Abuse Deterrent Controlled Release Matrix Composition

| Components | Mass (mg/capsule) | Percentage (%) |
|---|---|---|
| BHT | 0.4 | 0.1 |
| BHA | 1.32 | 0.33 |
| Oxycodone | 40 | 10 |
| TOTAL | 400 | 100 |

TABLE 13

Exemplary Abuse Deterrent Controlled Release Matrix Composition

| Components | Mass (mg/capsule) | Mass (mg/capsule) | Percentage (%) |
|---|---|---|---|
| Soybean Oil | 66.07 | 264.28 | 66.07 |
| Ethocel ™ (20 cP) | 2.5 | 10 | 2.5 |
| Carnauba Wax | — | — | — |
| Bee's Wax | 5 | 20 | 5 |
| Methocel ™ A4M | 5 | 20 | 5 |
| Polyethylene Glycol 400 | 10 | 40 | 10 |
| Microcrystalline Cellulose | 1 | 4 | 1 |
| BHT | 0.1 | 0.4 | 0.1 |
| BHA | 0.33 | 1.32 | 0.33 |
| Oxycodone | 10 | 40 | 10 |
| TOTAL | 100 | 400 | 100 |

TABLE 14

Exemplary Abuse Deterrent Controlled Release Matrix Composition

| Components | Mass (mg/capsule) | Percentage (%) |
|---|---|---|
| Soybean Oil | 244.6 | 60.9 |
| Ethocel ™ (20 cP) | 12 | 3.0 |
| Carnauba Wax | 26 | 6.5 |
| Bee's Wax | — | — |
| Methocel ™ A4M | 36 | 9.0 |
| Polyethylene Glycol 400 | 40 | 10 |
| Microcrystalline Cellulose | — | — |
| BHT | 1 | 0.25 |
| BHA | 0.4 | 0.10 |
| Oxycodone | 42 | 10.4 |
| TOTAL | 402 | 100 |

TABLE 15

Exemplary Abuse Deterrent Controlled Release Matrix Composition

| Components | % Weight | | | | | | |
|---|---|---|---|---|---|---|---|
|  | F1 | F2 | F3 | F4 | F5 | F6 | F7 |
| Soybean Oil | 69.3 | 71.4 | 64.4 | 51.3 | 63.7 | 46.2 | 64.9 |
| Ethocel ™ | 9.9 | 13.0 | 11.7 | 10.3 | 11.5 | 10.3 | 9.1 |
| Methocel ™ | — | 2.6 | 11.5 | 7.7 | 11.3 | 10.2 | 15.3 |
| PEG 400 | — | 6.5 | 5.9 | 10.3 | 5.8 | 5.1 | 4.6 |
| MCC | — | — | — | — | 2.0 | 2.6 | 1.6 |
| PEO | 5.0 | — | — | — | — | — | — |
| Span ® 60 | 1.0 | — | — | — | — | — | — |
| Capmul ® MCM | — | — | — | 15.4 | — | — | — |
| Di water | 9.9 | — | — | — | — | 20.5 | — |
| Hydrocodone | 5.0 | 6.5 | 5.9 | 5.1 | 5.8 | 5.1 | 4.6 |
| Total | 100 | 100 | 100 | 100 | 100 | 100 | 100 |

TABLE 16

Exemplary Abuse Deterrent
Controlled Release Matrix Composition

| Components | % Weight | | | | | |
|---|---|---|---|---|---|---|
| | F8 | F9 | F10 | F11 | F12 | F13 |
| Soybean Oil | 65.4 | 65.4 | 65.4 | 65.4 | 63.2 | 67.1 |
| Ethocel ™ (4cP) | 3.5 | 3.5 | 3.5 | 3.5 | 6.8 | 3.4 |
| Carnauba Wax | 3.5 | 1.8 | — | 1.8 | 3.4 | 3.4 |
| Bee's Wax | — | 1.8 | 3.5 | — | — | — |
| Methocel ™ A4M | 5.2 | 5.2 | 5.2 | 5.2 | 5.1 | 5.0 |
| Polyethylene Glycol 400 | 10.5 | 10.5 | 10.5 | 10.5 | 10.1 | 10 |
| Microcrystalline Cellulose | 1.0 | 1.0 | 1.0 | 1.0 | 0.0 | 1.0 |
| BHT | 0.3 | 0.3 | 0.3 | 0.3 | 0.3 | 0.1 |
| BHA | 0.1 | 0.1 | 0.1 | 0.1 | 0.1 | — |
| Oxycodone | 10.5 | 10.5 | 10.5 | 10.5 | 10.5 | 10 |
| TOTAL | 100 | 100 | 100 | 100 | 100 | 100 |

Example 2

An exemplary abuse deterrent controlled release matrix composition as described herein comprises one or more liquid lipophilic vehicles, one or more organogelators, one or more hydrophilic polymers, one or more hydrophilic vehicles, one or more active pharmaceutical ingredients, optionally one or more semi-solid lipophilic vehicles, and optionally one or more disintegrants, and optionally one or more anti-oxidants as described in any one of Tables 7-27. An exemplary process for preparing an abuse deterrent controlled release matrix includes preparing a mixture comprising one or more liquid lipophilic vehicles, one or more organogelators, one or more hydrophilic polymers, one or more hydrophilic vehicles, one or more active pharmaceutical ingredients, optionally one or more semi-solid lipophilic vehicles, optionally one or more disintegrants, and optionally one or more anti-oxidants by heating the mixture from between 45° C. and 80° C. with stirring or agitation in a suitable vessel. The process further comprises decreasing the matrix mixture temperature to between about 25° C. and about 45° C. followed by a homogenization step, wherein the matrix is homogenized to be substantially flowable. Prior to encapsulation in a soft gel capsule described herein, the matrix is deaerated at a temperature of about 25° C. to about 45° C. Prior to encapsulation in a soft gel capsule comprising carrageenan as described herein, the matrix is deaerated at a temperature of about 25° C. to about 75° C.

The abuse deterrent matrices as described are multi-component and have a viscous yet flowable aspect as shown in FIG. 1 A-C. FIG. 1 A is the hydrophilic phase, B is a gelled phase, and C is the final mixture prior to encapsulation.

Matrix compositions containing one or more semi-solid lipophilic vehicles, such as a wax, may be further annealed by heating a soft capsule encapsulating the abuse deterrent controlled release matrix to a temperature of about 70° C. for about 0.25 hours to about one hour.

The process for manufacturing a soft capsule comprising the abuse deterrent matrices as described herein includes preparing a gel mass for a soft capsule; casting the gel mass into films or ribbons using heat-controlled drums or surfaces; and manufacturing a soft capsule comprising a matrix fill using rotary die technology. During this process, the abuse deterrent controlled release matrix is injected in to the lumen as the soft capsule is formed by rotary die encapsulation. The soft capsule can be a typical soft capsule ("soft gel") or an enteric soft capsule.

Example 3

The dissolution and release profiles under different dissolution conditions for pharmaceutical compositions comprising the abuse deterrent matrix formulations described in Tables 7-16 and Tables 18-19 are shown in FIGS. 1-17.

Figure 2:
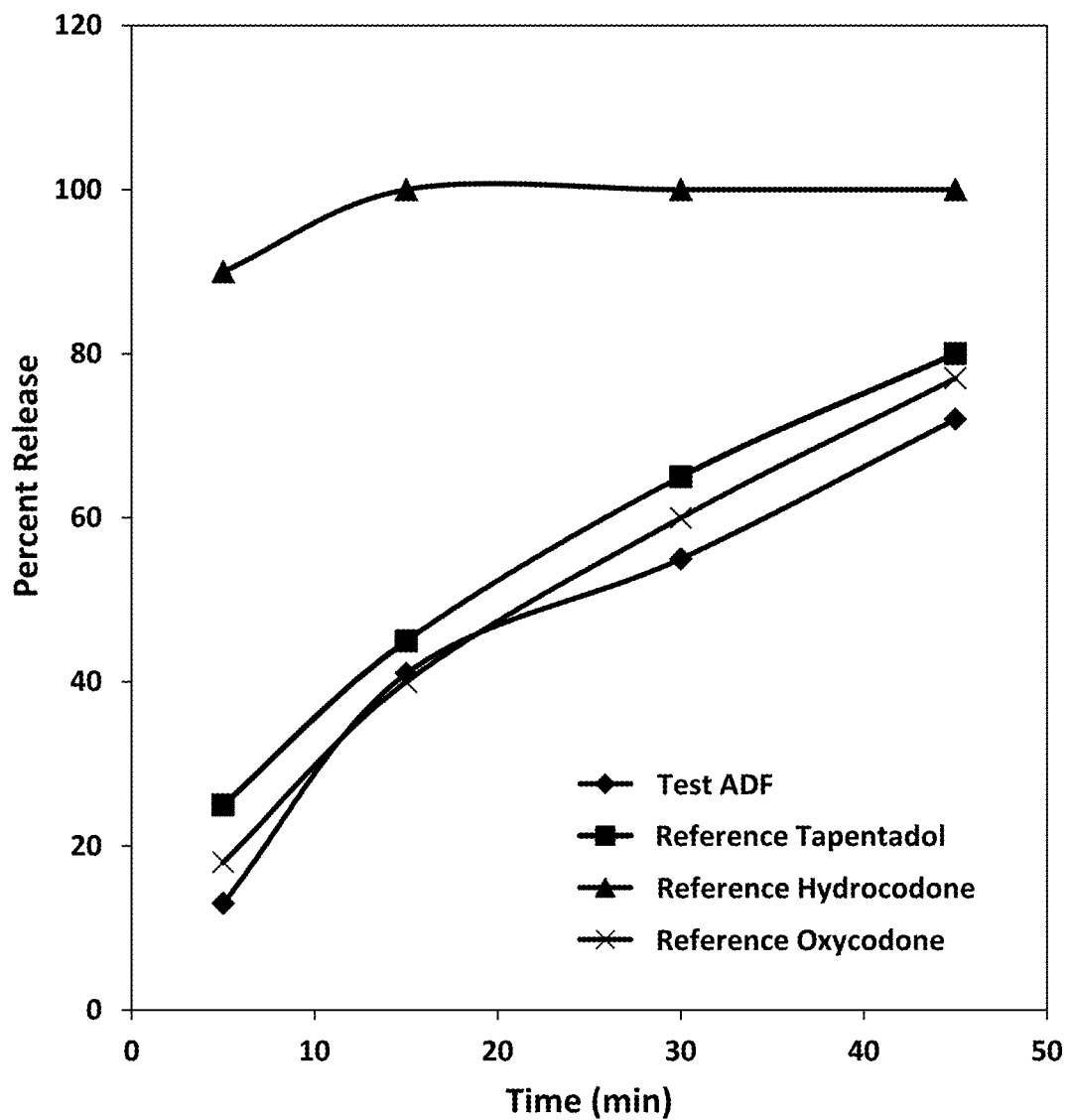
FIG. 2. Release profile of hydrocodone and oxycodone from the abuse deterrent matrix shown in Table 7 under boiling conditions compared to a reference abuse deterrent matrix.

The abuse deterrent controlled release matrix composition shown in Table 7, generated by the methods described herein and encapsulated in a soft gel capsule as described herein, was tested for its release rate under boiling conditions. As shown in FIG. 2, a test pharmaceutical composition comprising the abuse deterrent matrix of Table 7 comprising hydrocodone demonstrated a much lower release rate compared to a reference abuse deterrent pharmaceutical composition comprising either tapentadol or hydrocodone and was on par with reference abuse deterrent pharmaceutical compositions comprising either tapentadol or hydrocodone.

Figure 3:
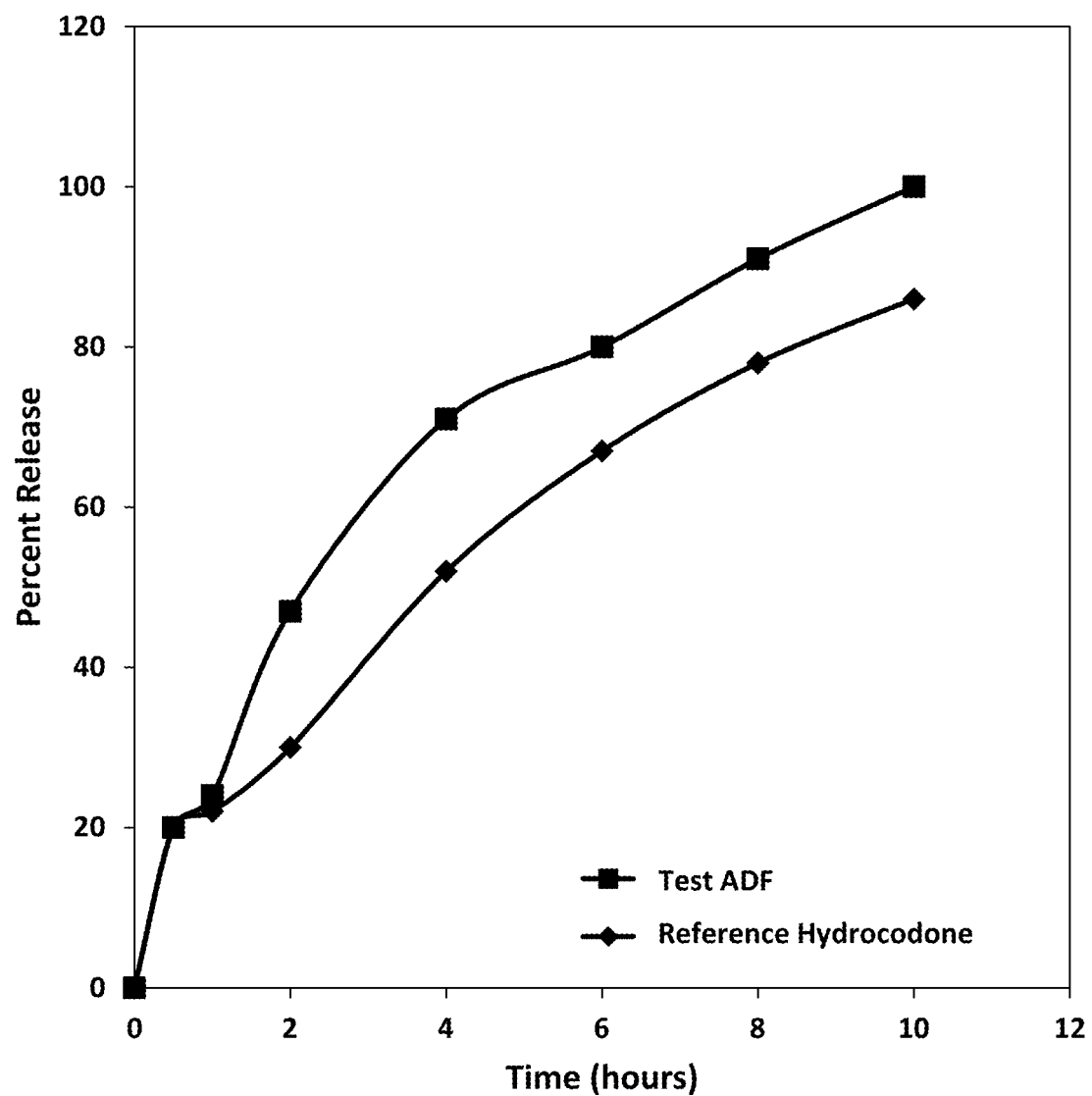
FIG. 3. Release profile of hydrocodone from the abuse deterrent matrix shown in Table 7 compared to a reference abuse deterrent matrix in a dissolution test using Apparatus III at 10 dips/min in a pH 6.8 buffer.

As shown in FIG. 3, the test pharmaceutical composition comprising the abuse deterrent matrix of Table 7 demonstrated a better release rate of hydrocodone in a dissolution test (Apparatus III at 10 dips/min) in 250 mL of a pH 6.8 buffer when compared to a reference abuse deterrent pharmaceutical composition comprising hydrocodone.

Figure 4:
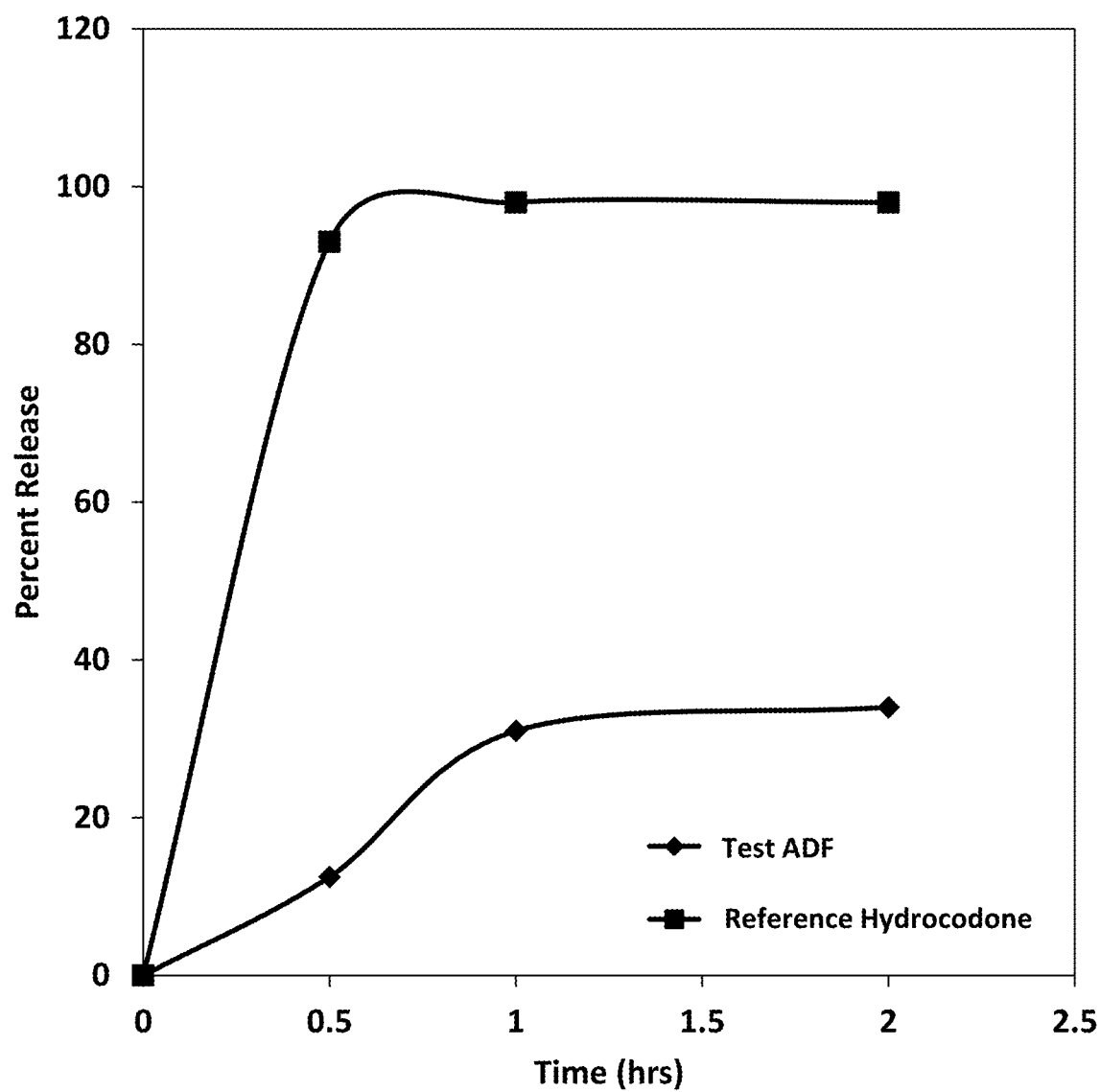
FIG. 4. Release profile of hydrocodone from the abuse deterrent matrix shown in Table 7 compared to a reference abuse deterrent matrix in a dissolution test using Apparatus I at 100 RPM in 500 mL of a 40% solution of ethanol in 0.1 NHCl (pH 1.2).

The test pharmaceutical composition comprising the abuse deterrent matrix of Table 7 demonstrated a lower release rate of hydrocodone in a dissolution test using Apparatus I at 100 RPM in 500 mL of a 40% solution of ethanol in 0.1 N HCl (pH 1.2) compared to a reference abuse deterrent pharmaceutical composition (FIG. 4).

Figure 5:
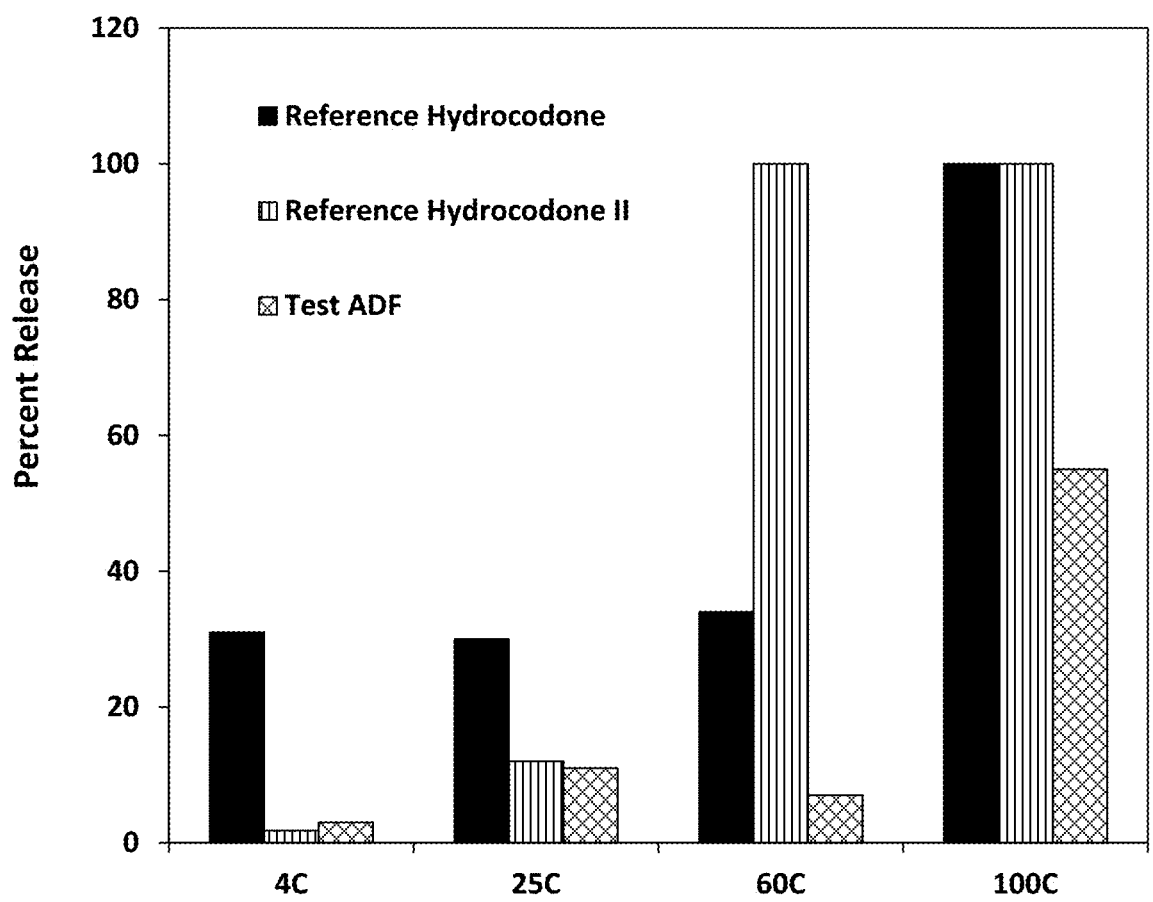
FIG. 5. Comparison of release profiles of hydrocodone from the abuse deterrent matrix shown in Table 7 with two different reference abuse deterrent matrices in distilled water at different temperatures and under agitation at 300 RPM.
Figure 6:
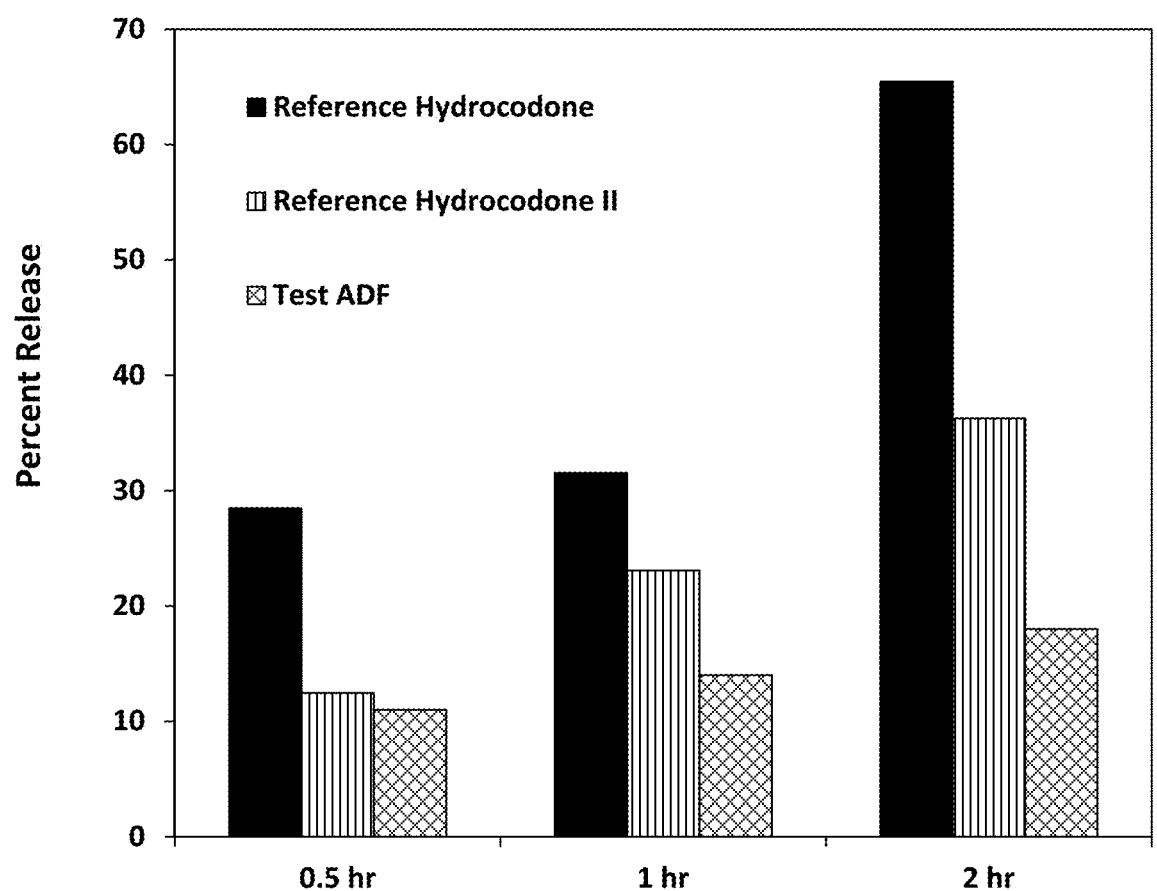
FIG. 6. Comparison of release profiles of hydrocodone from the abuse deterrent matrix shown in Table 7 to two different reference abuse deterrent matrices in distilled water at different times under agitation at 300 RPM.

The test pharmaceutical composition comprising the abuse deterrent matrix of Table 7 demonstrated a similar or lower release rate of hydrocodone in distilled water under agitation at 300 RPM at low temperatures of 4° C. and 25° C. when compared to two different reference abuse deterrent pharmaceutical compositions as shown in FIG. 5. Even lower release rates were observed at temperatures of 60° C. and 100° C. (FIG. 5). In addition, the test pharmaceutical composition demonstrated lower release rates in distilled water under agitation at 300 RPM from 0.5 hrs to 2 hrs (FIG. 6).

Figure 7:
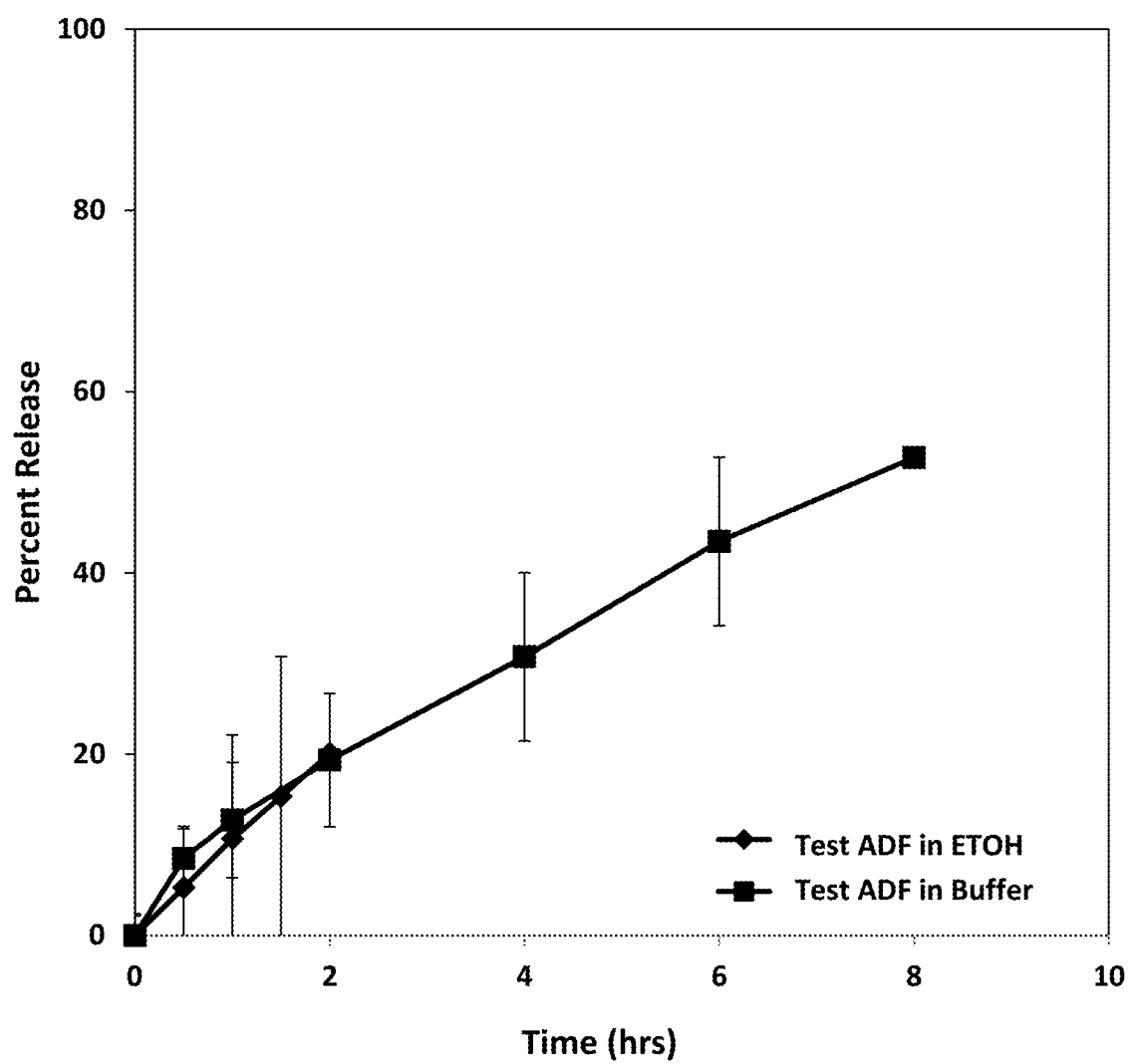
FIG. 7. Release profile of hydrocodone from the abuse deterrent matrix shown in Table 8 in a dissolution test using Apparatus III at 10 dips/min in a 40% solution of ethanol in 0.1 N HCl (pH 1.2) and a pH 6.8 buffer.

A test pharmaceutical composition comprising the abuse deterrent matrix of Table 8 hydrocodone had a similar release rate up to two hours in a dissolution test (Apparatus III at 10 dips/min) in a 40% solution of ethanol in 0.1 N HCl (pH 1.2) compared to a pH 6.8 buffer (FIG. 7).

Figure 8:
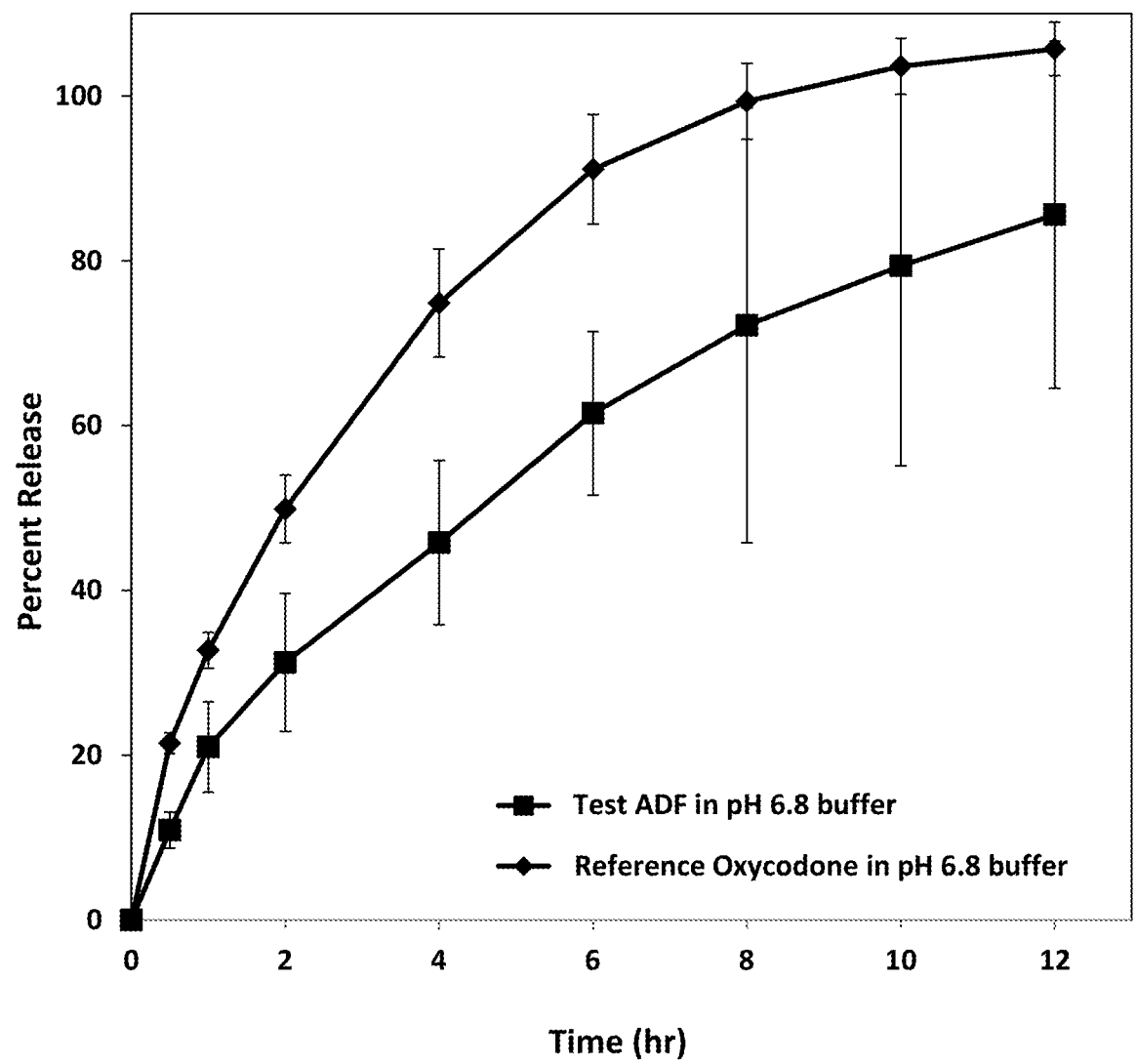
FIG. 8. Release profile of oxycodone from the abuse deterrent matrix labelled F8 shown in Table 16 compared to a reference abuse deterrent matrix in a dissolution test using Apparatus III at 10 dips/min RPM in 250 mL of a pH 6.8 buffer.
Figure 9:
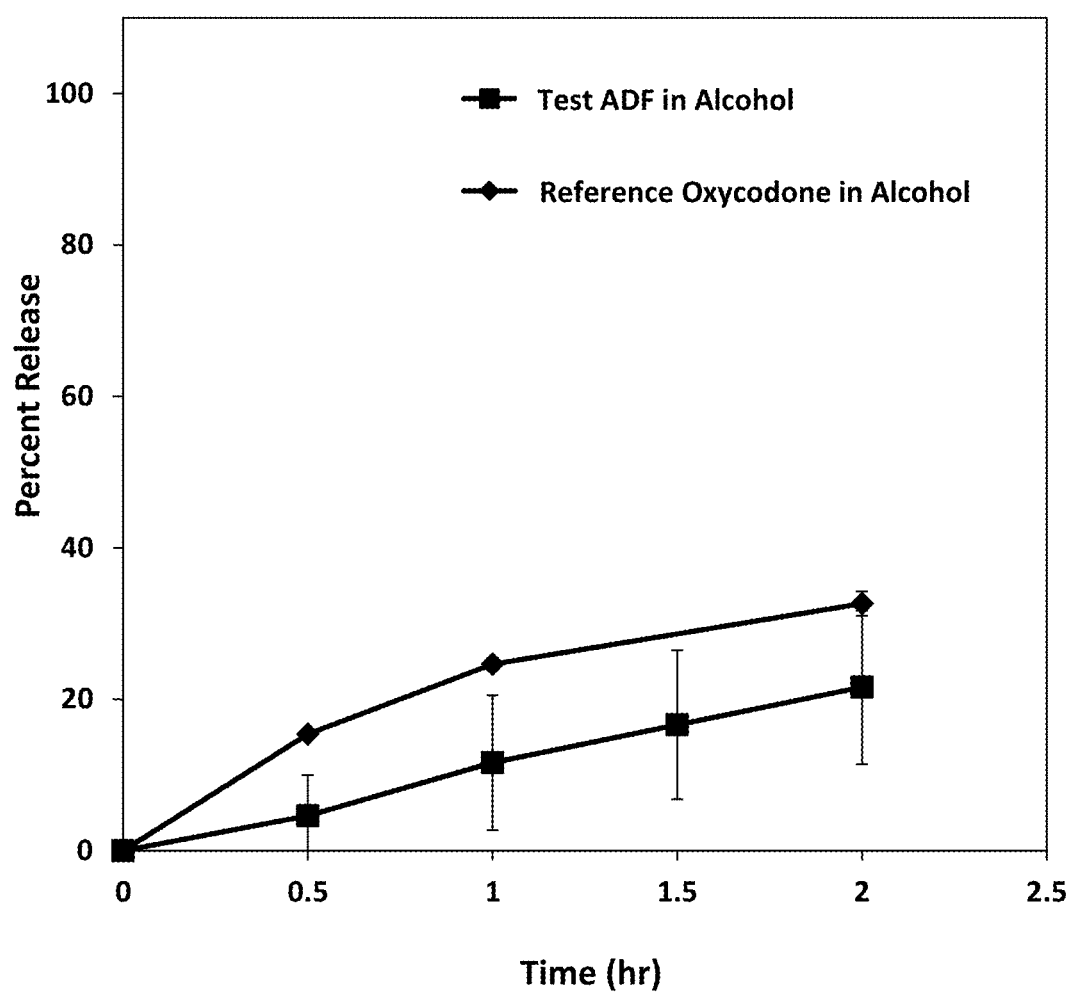
FIG. 9. Release profile of oxycodone from the abuse deterrent matrix labelled F8 shown in Table 16 compared to a reference abuse deterrent matrix in a dissolution test using Apparatus III at 10 dips/min RPM in a 40% solution of ethanol in 0.1 N HCl (pH 1.2).

The test pharmaceutical composition comprising the abuse deterrent matrix labelled F8 in Table 16 demonstrated a lower but comparable release rate of oxycodone in a dissolution test (Apparatus III at 10 dips/min) in a simulated intestinal fluid (SIF) buffer comprising 250 mL of a pH 6.8 buffer when compared to a reference abuse deterrent pharmaceutical composition comprising oxycodone (FIG. 8). However, as shown in FIG. 9, the test pharmaceutical composition demonstrated a lower release rate when compared to a reference abuse deterrent pharmaceutical composition comprising oxycodone (Apparatus III at 10 dips/min) in a 40% solution of ethanol in 0.1 N HCl (pH 1.2).

Figure 10:
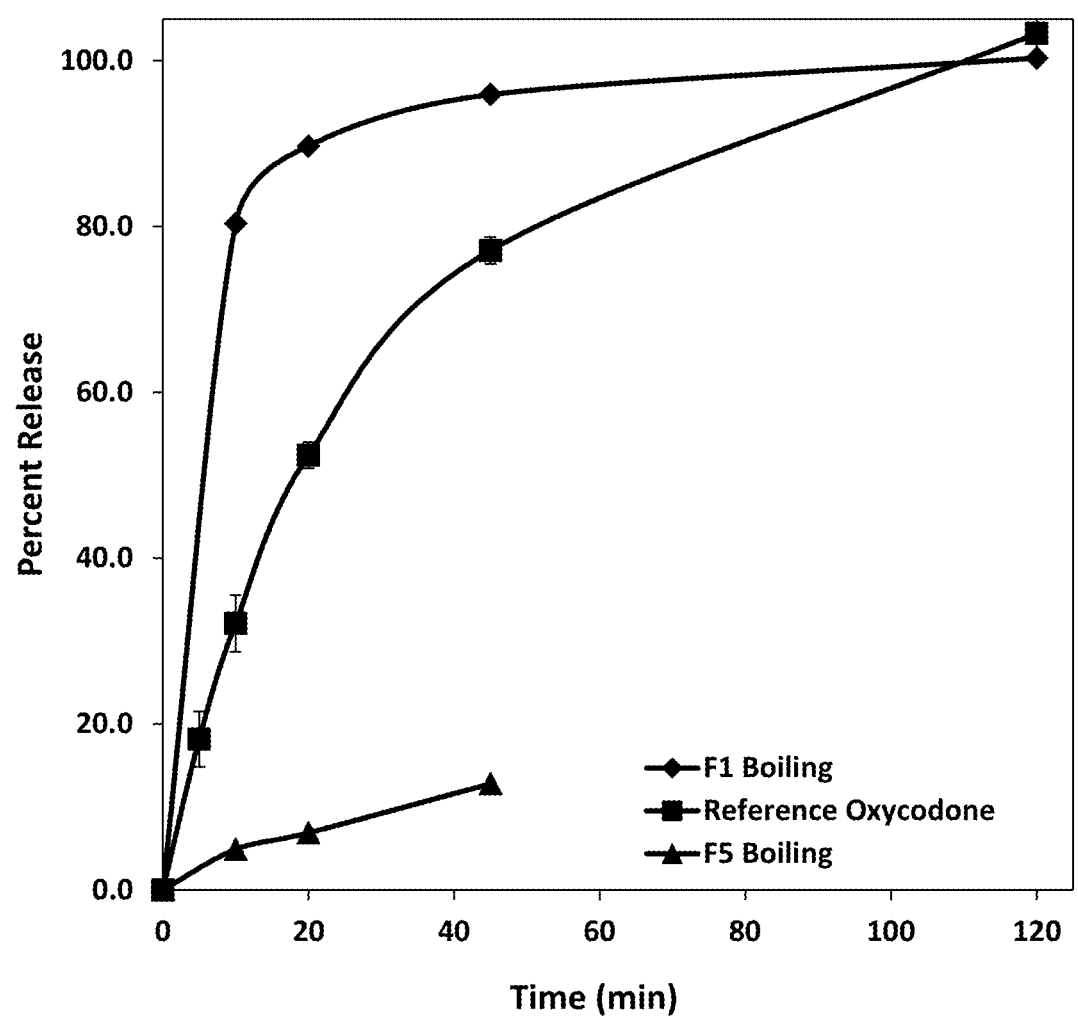
FIG. 10. Release profile of oxycodone from the abuse deterrent matrices labelled F12 and F13 shown in Table 16 under boiling conditions compared to a reference abuse deterrent matrix.

As further shown in FIG. 10, increasing the amount of Ethocel™ between formulations F12 and F13 of Table 16 at a higher viscosity (i.e., 20 cP) dramatically decreased the release rate of oxycodone under boiling conditions.

Figure 11:
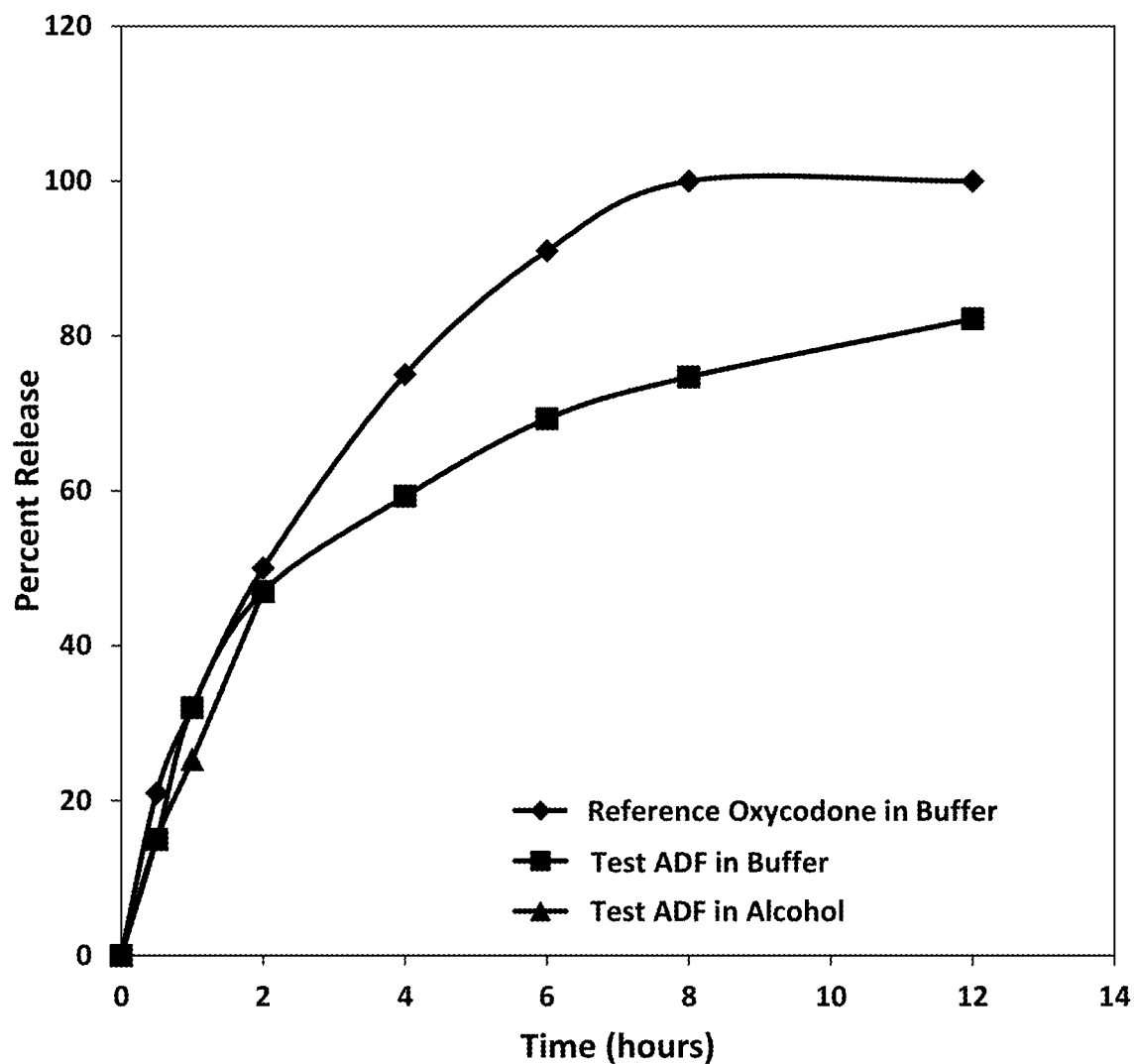
FIG. 11. Release profile of oxycodone from a test abuse deterrent matrix shown in Table 9 in a dissolution test using Apparatus III at 10 dips/min in a 40% solution of ethanol in 0.1 N HCl (pH 1.2) and a pH 6.8 buffer compared to the release rate of a reference abuse deterrent abuse deterrent matrix in a dissolution test using Apparatus III at 10 dips/min in a pH 6.8 buffer.
Figure 12:
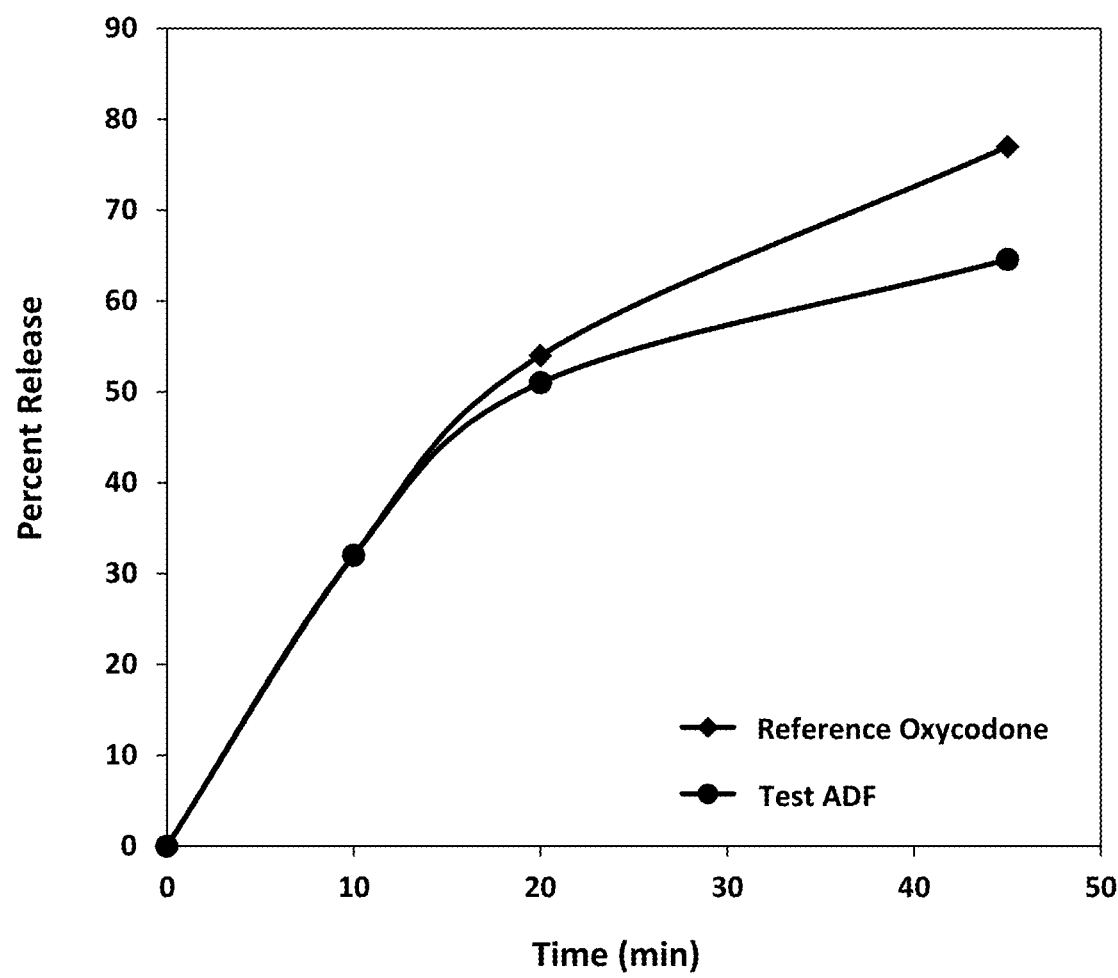
FIG. 12. Release profile of oxycodone from the abuse deterrent matrix shown in Table 9 under boiling conditions compared to a reference abuse deterrent matrix.

The test pharmaceutical composition comprising the abuse deterrent matrix of Table 9 comprising oxycodone had a similar release rate up to two hours in a dissolution test (Apparatus III at 10 dips/min) in a 40% solution of ethanol in 0.1 N HCl (pH 1.2) compared to a pH 6.8 buffer (FIG. 11). As further shown in FIG. 11, the test pharmaceutical composition demonstrated a comparable release rate in a pH 6.8 buffer compared to a reference pharmaceutical composition comprising oxycodone. The test pharmaceutical composition further displayed a lower release rate after about 15 minutes under boiling conditions in distilled water compared to a reference pharmaceutical composition comprising oxycodone (FIG. 12).

Figure 13:
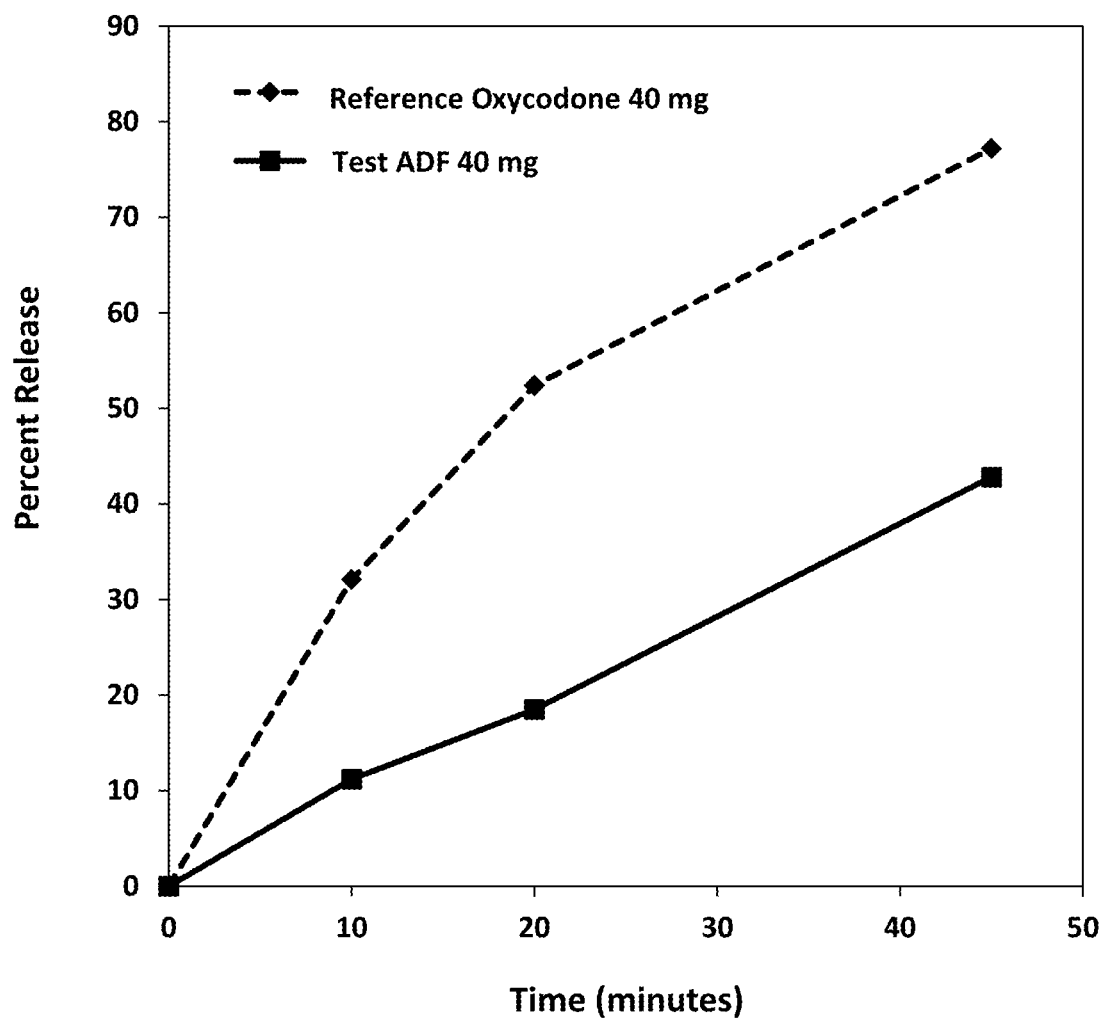
FIG. 13. Release profile of oxycodone from the abuse deterrent matrix shown in Table 10 under boiling conditions compared to a reference abuse deterrent matrix.

The test pharmaceutical composition comprising the abuse deterrent matrix of Table 10 comprising oxycodone demonstrated a lower release rate under boiling conditions compared to a reference pharmaceutical composition comprising oxycodone (FIG. 13).

Figure 16:
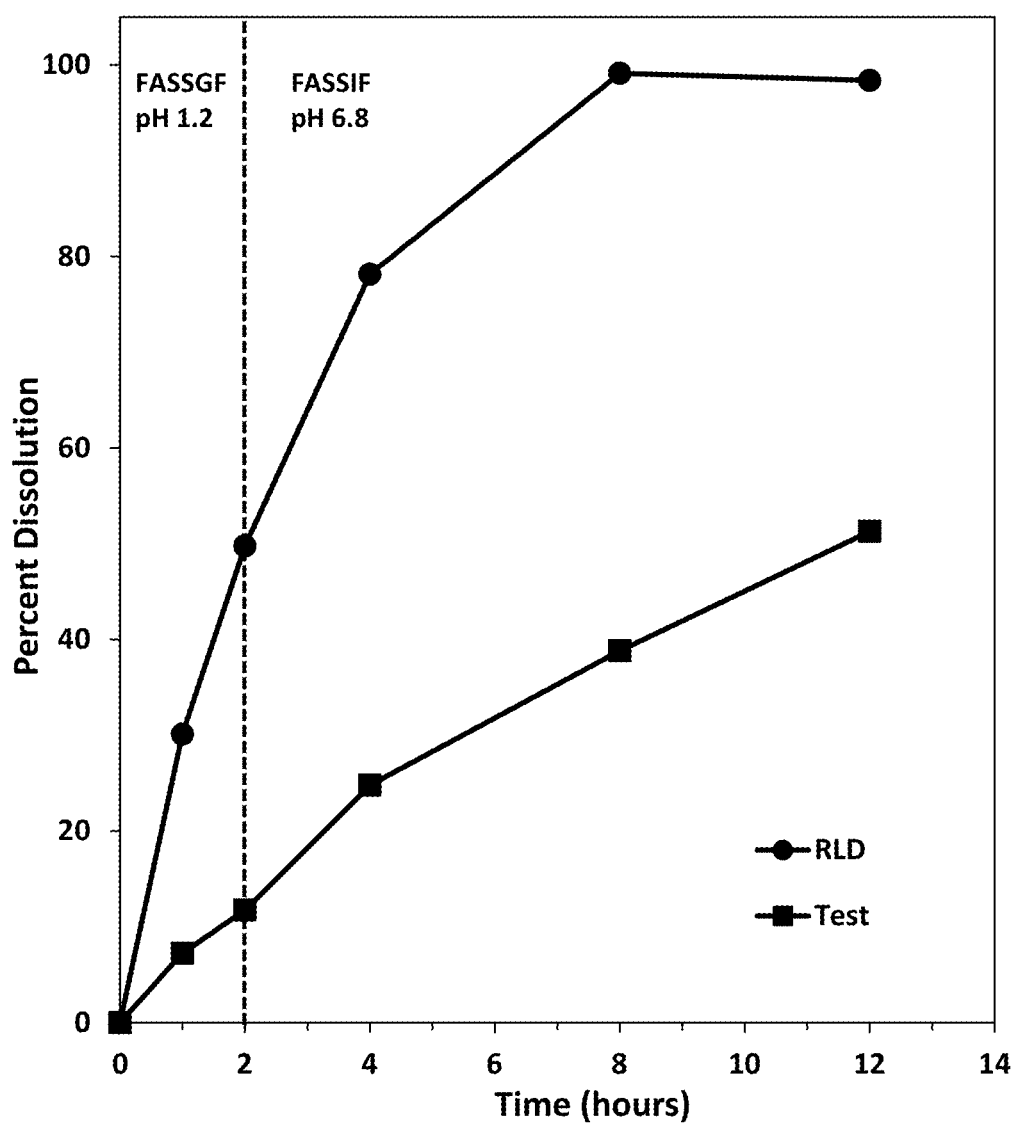
FIG. 16. Release profile of oxycodone from the abuse deterrent matrix shown in Table 17 (F 14) compared to a reference abuse deterrent matrix.
Figure 17:
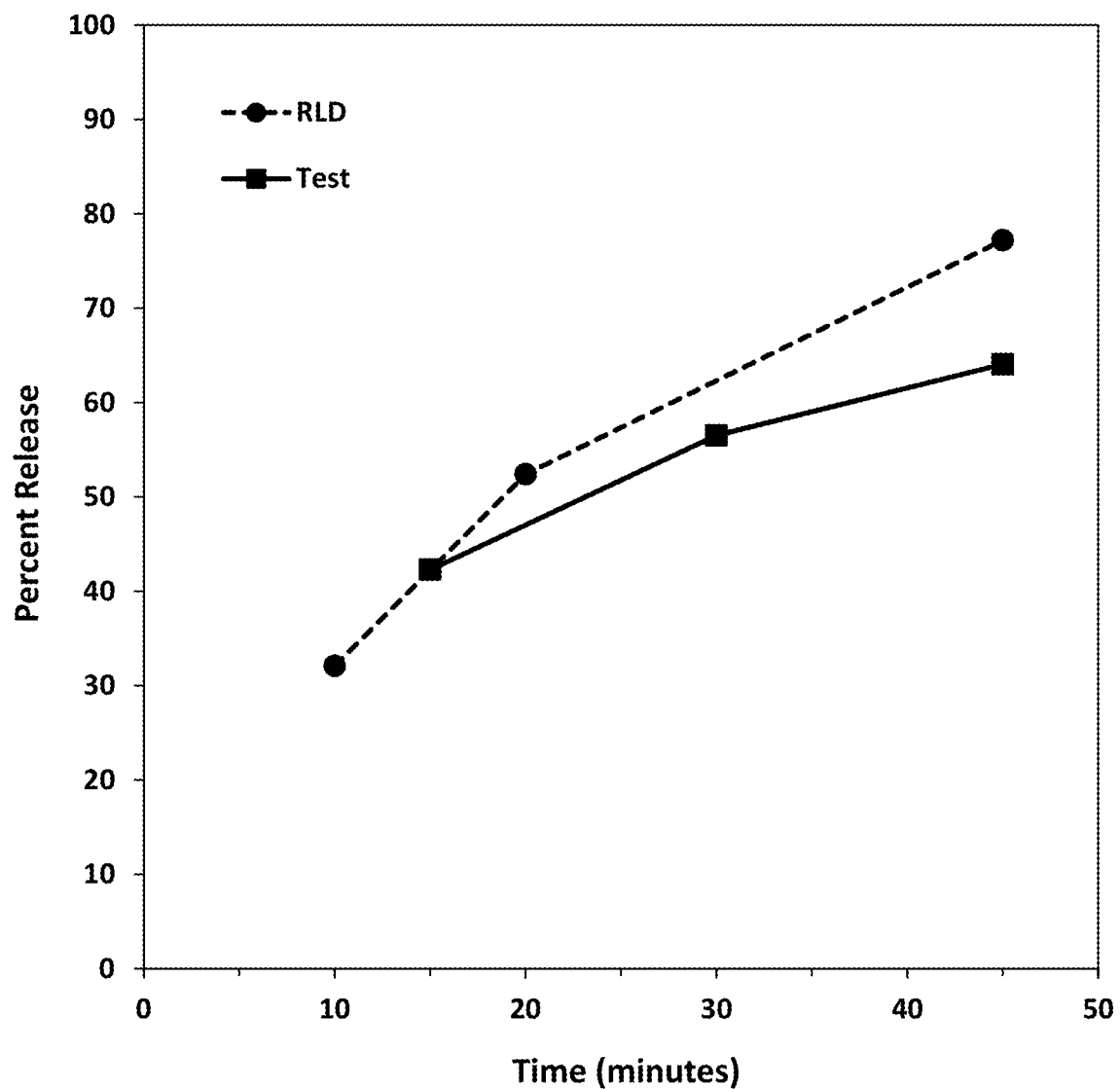
FIG. 17. Release profile of oxycodone under boiling conditions from the abuse deterrent matrix shown in Table 17 (F 14) compared to a reference abuse deterrent matrix.

The percent release of oxycodone was determined by measuring the amount of oxycodone released from the test and the reference abuse deterrent composition according to F14 of Table 19 in fasted-state simulated gastric fluid (FASSGF) at pH 1.2 for two hours and in fasted-state simulated intestinal fluid (FASSIF) at pH 6.8 for two hours according to USP specifications using Apparatus III at 30 dpm. As shown in FIG. 16 the test composition and reference abuse deterrent formulation demonstrated a similar percent release in FASSGF/FASSIF buffer. The composition F14 of Table 19 was further tested under boiling conditions and demonstrated a lower percent release after about 30 minutes compared to a reference abuse deterrent formulation (FIG. 17).

It was determined that increasing the amount of soybean oil of composition F14 of Table 19 and concomitantly decreasing the amount of polyethylene glycol, such as composition F15 improved the flowability of the composition for encapsulation feasibility. This composition, exemplified by F15 of Table 19 was tested and demonstrated a comparable release profile both in FASSGF/FASSIF buffers as well as under boiling conditions when compared to composition F14 (data not shown).

Example 4

Figure 14:
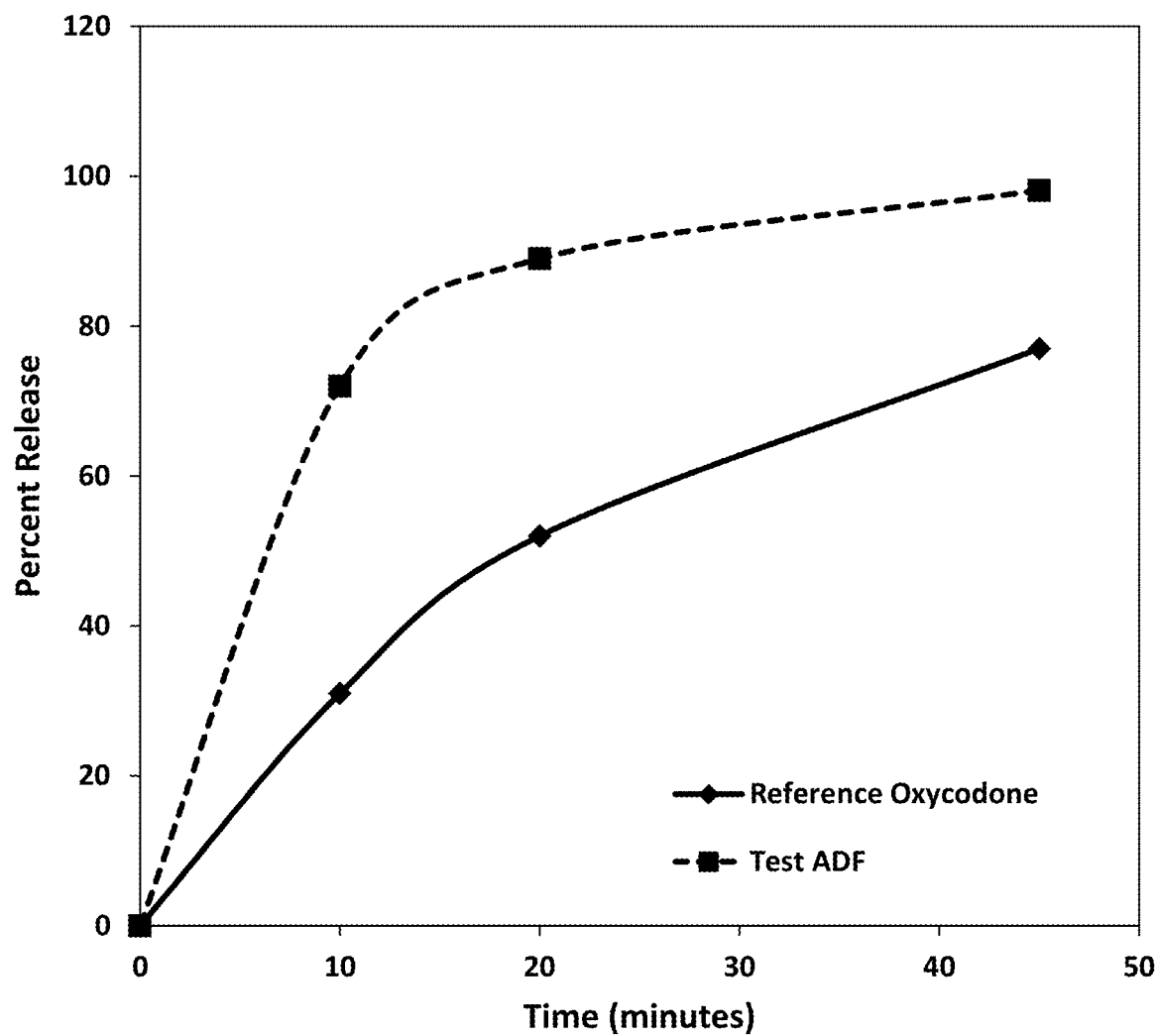
FIG. 14. Release profile of oxycodone from the abuse deterrent matrix shown in Table 12 without carnauba wax compared to a reference abuse deterrent matrix.

Differing compositions of wax were determined to affect the release rate of oxycodone from the test pharmaceutical composition comprising the abuse deterrent matrices shown in Tables 12-13. As shown in FIG. 14, the test pharmaceutical composition of Table 13, wherein carnauba wax was removed, demonstrated an increased release rate of 40 mg of oxycodone from the matrix when compared to a reference pharmaceutical composition comprising oxycodone. This, for example, is in contrast to the composition of Table 9, which comprises both carnauba wax and bee's wax and demonstrates a lower release rate compared to the same reference pharmaceutical composition comprising oxycodone (FIG. 13).

Figure 15:
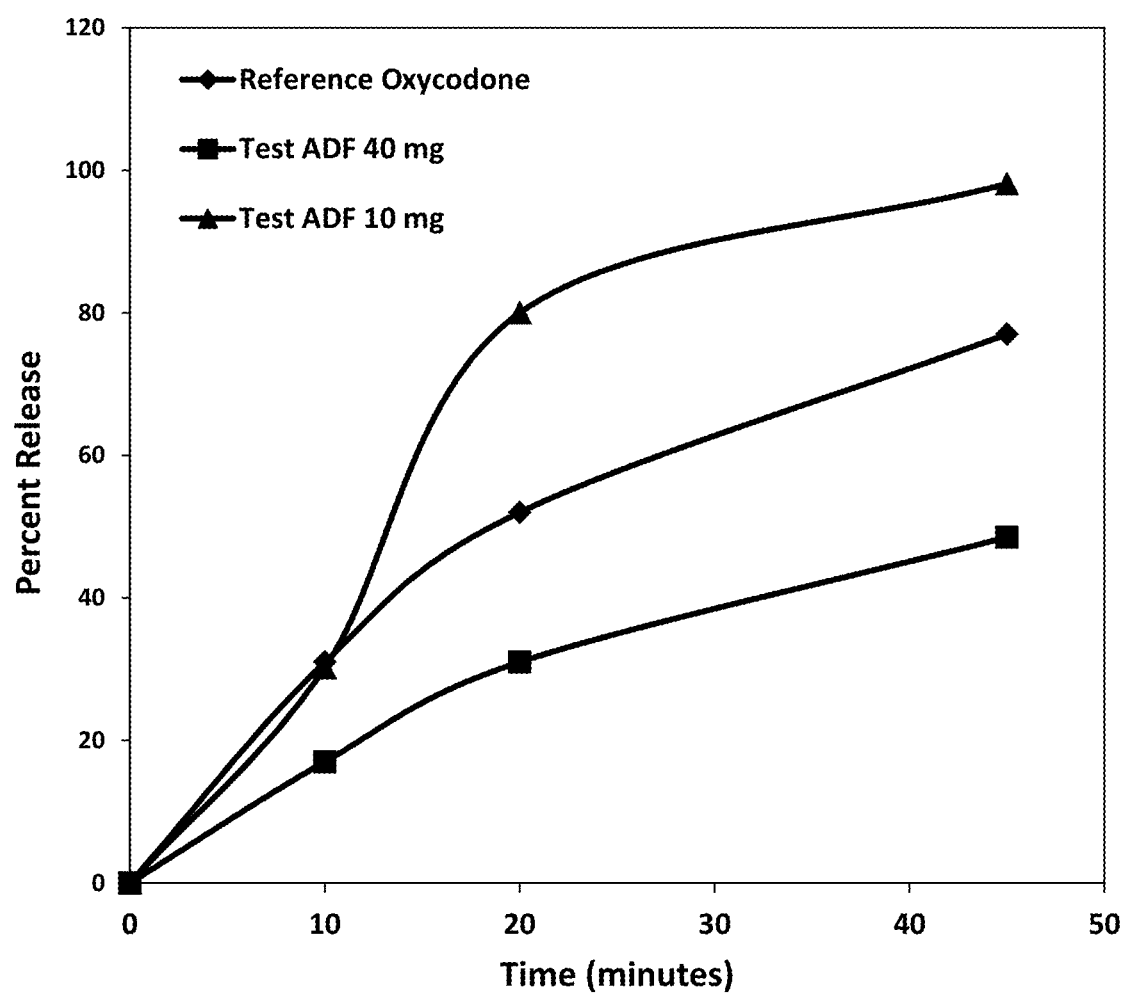
FIG. 15. Release profile of oxycodone from the abuse deterrent matrix shown in Table 13 with two different amounts of oxycodone compared to a reference abuse deterrent matrix.

As shown in FIG. 15, the test pharmaceutical composition of Table 13, wherein the amount of bee's wax was increased, led to a decreased release rate of oxycodone compared to the reference pharmaceutical composition comprising oxycodone only at a 40 mg dose and not at the 10 mg dose, suggesting higher concentrations of bee's wax or the addition of carnauba wax is also stabilizing to the abuse deterrent matrix under higher boiling temperatures.

Example 5

Additional abuse deterrent matrices may comprise a range of components as shown in Table 17. Additional abuse deterrent matrices having the composition shown in Tables 18-19 were prepared.

The compositions in Tables 18-19 were prepared by first heating the specified amount of soybean oil to about 60° C. and adding ethyl cellulose (e.g., Ethocel™) until it was completely dissolved and formed a first clear gel mixture. Next, the specified amounts of hydroxypropyl methylcellulose (e.g., Methocel™ K100M) was hydrated in the specified amount of polyethylene glycol (e.g., PEG 400) for at least about an hour. The active pharmaceutical ingredient oxycodone was then mixed with the hydrated hydroxypropylmethyl cellulose mixture to form a uniform blended mixture. Then the mixture containing oxycodone, hydroxypropyl methylcellulose and polyethylene glycol was added to the first mixture containing soybean oil and dissolved ethyl cellulose. The matrix compositions generated by the method described above was encapsulated in a soft capsule shell following standard rotary die encapsulation techniques. The matrices generated by the method described above are also suitable for other capsule shells, such as enteric soft capsule shells, hard capsule shells, and enteric hard capsule shells.

Further annealing processing steps may be needed for compositions comprising one or more waxes. For example, a composition comprising a soft capsule shell encapsulating the composition F16 of Table 19 was annealed by heating the capsule and matrix to about 70° C. for about 1 hour. The example method described above may be used to encapsulate any of the matrix compositions described herein (e.g., Tables 7-27) with suitable modification.

TABLE 17

Exemplary Abuse Deterrent Controlled Release Matrix Composition

| Components | Weight Percentage (%) |
| --- | --- |
| Soybean Oil | 30-65 |
| Ethocel ™ | 1-7 |
| Hydroxypropylmethyl cellulose | 8-22 |
| Wax 1 | 0-10 |
| Wax 2 | 0-10 |
| Polyethylene glycol | 8-40 |
| Oxycodone; Hydrocodone | 1-20 |
| TOTAL | 100 |

TABLE 18

Exemplary Abuse Deterrent Controlled Release Matrix Composition

| Components | Weight Percentage (%) |
| --- | --- |
| Soybean Oil | 52 |
| Ethocel ™ (20 cP) | 3.0 |
| Methocel ™ K100M | 15 |
| Polyethylene Glycol 400 | 20 |
| Oxycodone | 10 |
| TOTAL | 100 |

TABLE 19

Exemplary Abuse Deterrent Controlled Release Matrix Composition

| Components | Weight Percentage (%) | | |
|---|---|---|---|
| | F14 | F15 | F16 |
| Soybean Oil | 36.0 | 51 | 51 |
| Ethocel ™ (20 cP) | 3.0 | 2.7 | 0.8 |
| Carnauba Wax | 0.0 | 0.0 | 1.6 |
| Bee's Wax | 0.0 | 0.0 | 1.6 |
| Methocel ™ K100M | 15.0 | 13.8 | 12.0 |
| Polyethylene Glycol 400 | 36.0 | 23.0 | 24.0 |
| BHT | 0.1 | 0.1 | 0.1 |
| BHA | 0.1 | 0.1 | 0.1 |
| Oxycodone | 10.0 | 9.25 | 8.0 |
| TOTAL | 100 | 100 | 100 |

Example 6

Additional exemplary abuse deterrent matrix compositions useful for producing abuse deterrent controlled release soft gel capsules as described herein are shown in Tables 20-27. Composition components are set forth by weight percentage of the total weight of the matrix composition. Such compositions may be encapsulated in soft capsules, enteric soft capsules, hard capsules or enteric hard capsules.

TABLE 20

Exemplary Abuse Deterrent Controlled Release Matrix Compositions

| Components | EX 1 | EX 2 | EX 3 | EX 4 | EX 5 | EX 6 |
|---|---|---|---|---|---|---|
| | Weight Percentage (%) | | | | | |
| Total Hydrophobic Matrix (HBM) | 79.7 | 63.6 | 61.6 | 68.6 | 54.6 | 63.6 |
| Total Hydrophilic Matrix (HPM) | 19.4 | 16.4 | 16.4 | 16.4 | 44.4 | 16.4 |
| Total Polymer (tP) | 13.0 | 8.5 | 8.5 | 8.5 | 50.0 | 8.5 |
| Total Hydrophilic Vehicle (tHV) | 11.0 | 11.0 | 11.0 | 11.0 | 19.0 | 11.0 |
| Active Pharmaceut. Ingredient (API) | 1 | 10 | 10 | 15 | 1 | 20 |
| Components and Relational Ratios | | | | | | |
| Ratio of HBM to HPM | 4.1 | 3.9 | 3.8 | 4.2 | 1.2 | 3.9 |
| Ratio of Lipophilic Vehicle to tP | 5.4 | 6.7 | 6.4 | 7.2 | 0.4 | 6.7 |
| Ratio of Organogelator to Hydrophilic Polymer | 0.6 | 0.7 | 0.7 | 0.7 | 1.0 | 0.7 |
| Ratio of tHV to tP | 0.8 | 1.3 | 1.3 | 1.3 | 0.4 | 1.3 |
| Ratio of API to HBM | 0.01 | 0.2 | 0.2 | 0.2 | 0.02 | 0.3 |
| Ratio of API to HPM | 0.1 | 0.6 | 0.6 | 0.9 | 0.02 | 1.2 |
| Ratio of API to Total Matrix | 0.01 | 0.1 | 0.1 | 0.2 | 0.01 | 0.3 |

TABLE 21

Exemplary Abuse Deterrent Controlled Release Matrix Compositions

| Components | EX 7 | EX 8 | EX 9 | EX 10 | EX 11 | EX 12 |
|---|---|---|---|---|---|---|
| | Weight Percentage (%) | | | | | |
| Total Hydrophobic Matrix (HBM) | 66.1 | 39.6 | 58.6 | 72.9 | 67.4 | 51.6 |
| Total Hydrophilic Matrix (HPM) | 23.9 | 50.4 | 16.4 | 17.1 | 22.6 | 24.4 |
| Total Polymer (tP) | 22.0 | 33.0 | 8.5 | 9.0 | 9.5 | 8.5 |
| Total Hydrophilic Vehicle (tHV) | 3.5 | 25.0 | 11.0 | 13.7 | 16.7 | 11.0 |
| Active Pharmaceut. Ingredient (API) | 10 | 10 | 25 | 10 | 10 | 10 |
| Components and Relational Ratios | | | | | | |
| Ratio of HBM to HPM | 2.8 | 0.8 | 3.6 | 4.3 | 3.0 | 2.1 |
| Ratio of Lipophilic Vehicle to CRP | 2.4 | 0.6 | 6.1 | 6.7 | 6.0 | 5.2 |
| Ratio of Organogelator to Hydrophilic Polymer | 0.1 | 0.3 | 0.7 | 2.0 | 0.7 | 0.7 |
| Ratio of tHV to tP | 0.2 | 0.8 | 1.3 | 1.5 | 1.8 | 1.3 |
| Ratio of API to HBM | 0.2 | 0.3 | 0.4 | 0.1 | 0.1 | 0.2 |
| Ratio of API to HPM | 0.4 | 0.2 | 1.5 | 0.6 | 0.4 | 0.4 |
| Ratio of API to Total Matrix | 0.1 | 0.1 | 0.3 | 0.1 | 0.1 | 0.1 |

TABLE 22

Exemplary Abuse Deterrent Controlled Release Matrix Compositions

| Components | EX 13 | EX 14 | EX 15 | EX 16 | EX 17 | EX 18 |
|---|---|---|---|---|---|---|
| | Weight Percentage (%) | | | | | |
| Oil | 70 | 56.6 | 54.6 | 61.6 | 20.1 | 56.6 |
| Ethocel ™ | 5 | 3.5 | 3.5 | 3.5 | 25 | 3.5 |
| Wax 1 | 1 | 1 | 1 | 1 | 7 | 1 |
| Wax 2 | 3.7 | 2.5 | 2.5 | 2.5 | 2.5 | 2.5 |
| Methocel ™ | 8 | 5 | 5 | 5 | 25 | 5 |
| Polyethylene Glycol | 10 | 10 | 10 | 10 | 18 | 10 |
| Microcrystalline Cellulose | 1 | 1 | 1 | 1 | 1 | 1 |
| Plasticizer | — | — | 12 | — | — | — |
| Surfactant | — | 10 | — | — | — | — |
| BHT | 0.1 | 0.1 | 0.1 | 0.1 | 0.1 | 0.1 |
| BHA | 0.25 | 0.25 | 0.25 | 0.25 | 0.25 | 0.25 |
| Active Pharmaceut. Ingredient(s); (e.g., hydrocodone, oxycodone, naloxone, methylnaltrexone, naltrexone) | 1 | 10 | 10 | 15 | 1 | 20 |
| TOTAL | 100 | 100 | 100 | 100 | 100 | 100 |

TABLE 23

Exemplary Abuse Deterrent Controlled Release Matrix Compositions

| Components | EX 19 | EX 20 | EX 21 | EX 22 | EX 23 | EX 24 |
|---|---|---|---|---|---|---|
| | Weight Percentage (%) | | | | | |
| Oil | 10 | 10 | 25 | 10 | 10 | 10 |
| Ethocel ™ | 52.6 | 19.6 | 51.6 | 60.4 | 56.9 | 44.6 |
| Wax 1 | 2 | 8 | 3.5 | 6 | 4 | 3.5 |
| Wax 2 | 4.5 | 5 | 1 | 2 | 2 | 1 |
| Methocel ™ | 7 | 7 | 2.5 | 4.5 | 4.5 | 2.5 |
| Polyethylene Glycol | 20 | 25 | 5 | 3 | 5.5 | 5 |
| Microcrystalline Cellulose | 2 | 20 | 10 | 12 | 15 | 10 |
| Plasticizer | 1.5 | 5 | 1 | 1.7 | 1.7 | 1 |

TABLE 23-continued

Exemplary Abuse Deterrent Controlled Release Matrix Compositions

| Components | Weight Percentage (%) | | | | | |
|---|---|---|---|---|---|---|
| | EX 19 | EX 20 | EX 21 | EX 22 | EX 23 | EX 24 |
| Surfactant | — | — | — | — | — | 14 |
| BHT | — | — | — | — | — | 8 |
| BHA | 0.1 | 0.1 | 0.1 | 0.1 | 0.1 | 0.1 |
| Active Pharmaceut. Ingredient(s); (e.g., hydrocodone, oxycodone, naloxone, methylnaltrexone, naltrexone) | 0.25 | 0.25 | 0.25 | 0.25 | 0.25 | 0.25 |
| TOTAL | 100 | 100 | 100 | 100 | 100 | 100 |

TABLE 24

Exemplary Abuse Deterrent Controlled Release Matrix Compositions

| | EX 25 | EX 26 | EX 27 | EX 28 | EX 29 | EX 30 |
|---|---|---|---|---|---|---|
| Components | Weight Percentage (%) | | | | | |
| Total Hydrophobic Matrix (HBM) | 55 | 55 | 57 | 59.5 | 62 | 62.5 |
| Total Hydrophilic Matrix (HPM) | 35.4 | 25.4 | 33.4 | 30.9 | 28.4 | 27.9 |
| Total Polymer (tP) | 18.0 | 15.5 | 19.0 | 19.5 | 20.0 | 20.5 |
| Total Hydrophilic Vehicle (tHV) | 20.0 | 12.5 | 16.0 | 12.5 | 13.0 | 9.5 |
| Active Pharmaceut. Ingredient (API) | 10.0 | 20.0 | 10.0 | 10.0 | 10.0 | 10.0 |
| Components and Relational Ratios | | | | | | |
| Ratio of HBM to HPM | 1.6 | 2.2 | 1.7 | 1.9 | 2.2 | 2.2 |
| Ratio of Lipophilic Vehicle to CRP | 2.9 | 3.4 | 2.9 | 3.0 | 2.6 | 2.9 |
| Ratio of Organogelator to Hydrophilic Polymer | 0.2 | 0.2 | 0.1 | 0.1 | 0.3 | 0.1 |
| Ratio of tHV to tP | 1.1 | 0.8 | 0.8 | 0.6 | 0.7 | 0.5 |
| Ratio of API to HBM | 0.2 | 0.4 | 0.2 | 0.2 | 0.2 | 0.2 |
| Ratio of API to HPM | 0.3 | 0.8 | 0.3 | 0.3 | 0.4 | 0.4 |
| Ratio of API to Total Matrix | 0.1 | 0.2 | 0.1 | 0.1 | 0.1 | 0.1 |

TABLE 25

Exemplary Abuse Deterrent Controlled Release Matrix Compositions

| | EX 31 | EX 32 | EX 33 | EX 34 | EX 35 | EX 36 |
|---|---|---|---|---|---|---|
| Components | Weight Percentage (%) | | | | | |
| Total Hydrophobic Matrix (HBM) | 56.5 | 55 | 68.5 | 63 | 56.5 | 56 |
| Total Hydrophilic Matrix (HPM) | 33.9 | 30.4 | 30.9 | 32.4 | 33.9 | 34.4 |
| Total Polymer (tP) | 16.5 | 18.0 | 19.5 | 22.0 | 19.0 | 15.0 |
| Total Hydrophilic Vehicle (tHV) | 18.5 | 15.0 | 14.5 | 15.0 | 17.0 | 23.0 |
| Active Pharmaceut. Ingredient (API) | 10.0 | 15.0 | 1.0 | 5.0 | 10.0 | 10.0 |
| Components and Relational Ratios | | | | | | |
| Ratio of HBM to HPM | 1.7 | 1.8 | 2.2 | 1.9 | 1.7 | 1.6 |
| Ratio of Lipophilic Vehicle to CRP | 2.7 | 2.9 | 3.3 | 2.6 | 2.8 | 3.5 |
| Ratio of Organogelator to Hydrophilic Polymer | 0.1 | 0.2 | 0.2 | 0.3 | 0.2 | 0.4 |
| Ratio of tHV to tP | 1.1 | 0.8 | 0.7 | 0.7 | 0.9 | 1.5 |
| Ratio of API to HBM | 0.2 | 0.3 | 0.0 | 0.1 | 0.2 | 0.2 |
| Ratio of API to HPM | 0.3 | 0.5 | 0.0 | 0.2 | 0.3 | 0.3 |
| Ratio of API to Total Matrix | 0.1 | 0.2 | 0.0 | 0.1 | 0.1 | 0.1 |

TABLE 26

Exemplary Abuse Deterrent Controlled Release Matrix Compositions

| | Weight Percentage (%) | | | | | |
|---|---|---|---|---|---|---|
| Components | EX 37 | EX 38 | EX 39 | EX 40 | EX 41 | EX 42 |
| Oil | 52 | 52 | 55 | 58 | 52 | 60 |
| Ethocel ™ | 3 | 3 | 2 | 1.5 | 5 | 2.5 |
| Wax 1 | 0 | 0 | 0 | 0 | 5 | 0 |
| Wax 2 | 0 | 0 | 0 | 0 | 0 | 0 |
| Hydroxy-propylmethyl cellulose | 15 | 12.5 | 17 | 18 | 15 | 18 |
| Polyethylene Glycol | 20 | 12.5 | 16 | 12.5 | 13 | 9.5 |
| Opt. BHT | 0.1 | 0.1 | 0.1 | 0.1 | 0.1 | 0.1 |
| Opt. BHA | 0.25 | 0.25 | 0.25 | 0.25 | 0.25 | 0.25 |
| Active Pharmaceut. Ingredient(s); (e.g., hydrocodone, oxycodone, naloxone, methylnaltrexone, naltrexone) | 10 | 20 | 10 | 10 | 10 | 10 |
| TOTAL | 100 | 100 | 100 | 100 | 100 | 100 |

TABLE 27

Exemplary Abuse Deterrent Controlled Release Matrix Compositions

| | Weight Percentage (%) | | | | | |
|---|---|---|---|---|---|---|
| Components | EX 43 | EX 44 | EX 45 | EX 46 | EX 47 | EX 48 |
| Oil | 45 | 52 | 65 | 58 | 54 | 52 |
| Ethocel ™ | 1.5 | 3 | 3.5 | 5 | 2.5 | 4 |
| Wax 1 | 5 | 0 | 0 | 0 | 0 | 0 |
| Wax 2 | 5 | 0 | 0 | 0 | 0 | 0 |
| Hydroxy-propylmethyl cellulose | 15 | 15 | 16 | 17 | 16.5 | 11 |

TABLE 27-continued

Exemplary Abuse Deterrent Controlled Release Matrix Compositions

| | Weight Percentage (%) | | | | | |
|---|---|---|---|---|---|---|
| Components | EX 43 | EX 44 | EX 45 | EX 46 | EX 47 | EX 48 |
| Polyethylene Glycol | 18.5 | 15 | 14.5 | 15 | 17 | 23 |
| Opt. BHT | 0.1 | 0.1 | 0.1 | 0.1 | 0.1 | 0.1 |
| Opt. BHA | 0.25 | 0.25 | 0.25 | 0.25 | 0.25 | 0.25 |
| Active Pharmaceut. Ingredient(s); (e.g., hydrocodone, oxycodone, naloxone, methylnaltrexone, naltrexone) | 10 | 15 | 1 | 5 | 10 | 10 |
| TOTAL | 100 | 100 | 100 | 100 | 100 | 100 |

What is claimed is:

1. An abuse deterrent oral pharmaceutical composition comprising a soft gelatin capsule shell encapsulating a tamper resistant, homogenous viscous, yet flowable matrix consisting essentially of:
 (a) about 50% to about 70% by mass olive oil, soybean oil, or a combination thereof;
 (b) about 3% to about 10% by mass ethylcellulose;
 (d) about 2% to about 30% by mass hydroxypropyl methylcellulose;
 (e) about 4% to about 11% by mass polyethylene glycol having a molecular weight of about 200 to about 8000;
 (f) about 1% to about 35% by mass of one or more active pharmaceutical ingredients that is dissolved in the flowable matrix; and
 (g) optionally one or more antioxidants.

2. The composition of claim 1, wherein the anti-oxidant comprises about 0.05% to about 0.5% by mass.

3. The composition of claim 1, wherein the composition comprises a mass ratio of active pharmaceutical ingredient to the combined mass of the other components of about 1:100 to about 1:3.

4. The composition of claim 1, wherein the ethylcellulose is capable of forming a gel at a temperature of about 90° C. to about 120° C.

5. The composition of claim 1, wherein the ethylcellulose comprises a viscosity value of about 3 cP to about 20 cP.

6. The composition of claim 1, wherein the hydroxypropylmethylcellulose has a viscosity value of about 50 cP to about 100,000 cP.

7. The composition of claim 1, wherein the anti-oxidant comprises butylated hydroxytoluene (BHT), butylated hydroxyanisole (BHA), or a combination thereof.

8. The composition of claim 1, wherein the active pharmaceutical ingredient comprises at least one of: hydrocodone, morphine, morphine analogues, or morphine antagonists, tapentadol, codeine, morphine, methadone, fentanyl and analogs, hydrocodone hydrochloride, hydrocodone bitartrate, hydromorphone, oxymorphone, oxycodone, meperidine, propoxyphene, flunitrazepam, barbiturates, amytal, nembutal, seconal, phenobarbital; benzodiazepines, zolpidem, zaleplon, eszopiclone, amphetamines, methylphenidate, or a combination thereof.

9. The composition of claim 1, wherein the active pharmaceutical ingredient comprises hydrocodone or oxycodone.

10. The composition of claim 1, wherein the tamper resistant, homogenous viscous, yet flowable matrix consists essentially of:
 (a) about 50% to about 70% by mass soybean oil;
 (b) about 2% to about 7% by mass ethylcellulose;
 (c) about 2% to about 15% by mass hydroxypropylmethylcellulose;
 (d) about 4% to about 11% by mass polyethylene glycol 400; and
 (e) about 10.5% by mass of hydrocodone or oxycodone; and optionally
 (f) about 0.25% by mass BHT; and
 (g) about 0.1% by mass BHA.

11. The composition of claim 1, wherein the soft gelatin capsule shell consists essentially of a film forming polymer, a plasticizer, and a solvent, and optionally, an opacifying agent, a coloring agent, or a pharmaceutical excipient.

12. A method for making a tamper resistant homogenous viscous yet flowable semisolid dosage form comprising:
 (i) heating soybean oil to about 60° C. and adding ethylcellulose until completely dissolved to form a first clear mixture;
 (ii) hydrating hydroxypropylmethylcellulose with polyethylene glycol;
 (iii) mixing hydrocodone or oxycodone with the mixture of step (ii) to form a second uniform mixture; and
 (iv) adding the second uniform mixture of step (iii) to the first clear mixture of (i) to form a final uniform matrix composition, and
 (v) encapsulating the matrix composition of (iv) in a soft gel capsule using rotary die encapsulation.

13. A tamper resistant oral pharmaceutical composition comprising a soft gelatin capsule shell encapsulating a tamper resistant, homogenous viscous, yet flowable matrix consisting essentially of:
 (a) about 50% to about 70% by mass soybean oil;
 (b) about 2% to about 7% by mass ethylcellulose;
 (c) about 2% to about 15% by mass hydroxypropylmethylcellulose;
 (d) about 4% to about 11% by mass polyethylene glycol 400; and
 (e) about 10.5% by mass of hydrocodone or oxycodone; and optionally
 (f) about 0.25% by mass BHT; and
 (g) about 0.1% by mass BHA.

14. A method for treating pain in a subject in need thereof, the method comprising administering the composition of claim 13 to the subject.

15. The composition of claim 1, wherein the soft gelatin capsule shell consist essentially of:
 (a) about 25% to about 50% by mass gelatin;
 (b) about 15% to about 25% by mass glycerol; and
 (c) about 20% to about 40% by mass water.

16. A pharmaceutical dosage form made by the method of claim 12.

17. The composition of claim 13, wherein the soft gelatin capsule shell consists essentially of:
 (a) about 25% to about 50% by mass gelatin;
 (b) about 15% to about 25% by mass glycerol; and
 (c) about 20% to about 40% by mass water.

* * * * *